(12) United States Patent
Pietsch et al.

(10) Patent No.: US 10,864,268 B2
(45) Date of Patent: Dec. 15, 2020

(54) CD47 ANTIBODIES, METHODS, AND USES

(71) Applicant: Janssen Pharmaceutica NV, Beerse (BE)

(72) Inventors: Christine Pietsch, Elkins Park, PA (US); Jianying Dong, San Diego, CA (US); Rosa Cardoso, North Wales, PA (US); Hong Zhou, Sand Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 224 days.

(21) Appl. No.: 15/527,551

(22) PCT Filed: Nov. 17, 2015

(86) PCT No.: PCT/US2015/061014
§ 371 (c)(1),
(2) Date: May 17, 2017

(87) PCT Pub. No.: WO2016/081423
PCT Pub. Date: May 26, 2016

(65) Prior Publication Data
US 2018/0250395 A1 Sep. 6, 2018

Related U.S. Application Data

(60) Provisional application No. 62/081,134, filed on Nov. 18, 2014.

(51) Int. Cl.
| | | |
|---|---|---|
| *C07K 16/00* | (2006.01) | |
| *A61K 39/395* | (2006.01) | |
| *C07K 16/28* | (2006.01) | |
| *A61K 39/00* | (2006.01) | |
| *A61P 35/00* | (2006.01) | |

(52) U.S. Cl.
CPC .... *A61K 39/39558* (2013.01); *C07K 16/2803* (2013.01); *C07K 16/2896* (2013.01); *A61K 2039/505* (2013.01); *A61P 35/00* (2018.01); *C07K 2317/34* (2013.01); *C07K 2317/52* (2013.01); *C07K 2317/55* (2013.01); *C07K 2317/565* (2013.01); *C07K 2317/567* (2013.01); *C07K 2317/71* (2013.01); *C07K 2317/73* (2013.01); *C07K 2317/734* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,068,506 A | 12/1962 | Oishei |
| 3,068,507 A | 12/1962 | Evans |
| 3,773,919 A | 11/1973 | Boswell et al. |
| 4,522,811 A | 6/1985 | Eppstein et al. |
| 4,683,195 A | 7/1987 | Mullis et al. |
| 4,683,202 A | 7/1987 | Mullis |
| 4,816,567 A | 3/1989 | Cabilly et al. |
| 4,946,778 A | 8/1990 | Ladner et al. |
| 5,233,409 A | 8/1993 | Schwab |
| 5,530,101 A | 6/1996 | Queen et al. |
| 5,585,089 A | 12/1996 | Queen et al. |
| 5,693,761 A | 12/1997 | Queen et al. |
| 5,693,792 A | 12/1997 | Torii et al. |
| 5,703,057 A | 12/1997 | Johnston et al. |
| 5,714,350 A | 2/1998 | Co et al. |
| 5,733,743 A | 3/1998 | Johnson et al. |
| 5,777,085 A | 7/1998 | Co et al. |
| 5,939,598 A | 8/1999 | Kucherlapati et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,472,147 B1 | 10/2002 | Janda et al. |
| 6,521,404 B1 | 2/2003 | Griffiths et al. |

FOREIGN PATENT DOCUMENTS

| | | |
|---|---|---|
| EP | 0463151 B1 | 6/1996 |
| EP | 2351838 A1 | 8/2011 |
| JP | 3068180 B2 | 10/1991 |
| JP | 3068506 B2 | 10/1991 |
| JP | 3068507 B2 | 10/1991 |
| WO | 1992/01047 A1 | 1/1992 |
| WO | 1994/02602 A1 | 2/1994 |
| WO | 1995/22618 A1 | 8/1995 |
| WO | 1996/34096 A1 | 10/1996 |
| WO | 1998/24893 A2 | 6/1998 |
| WO | 2000/76310 | 12/2000 |
| WO | 200233073 A1 | 4/2002 |

(Continued)

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Bobo, et al., Convection-enhanced delivery of macromolecules in the brain, Proc. Natd. Acad. Sci., Oct. 25, 1993, pp. 2076-2080, vol. 91.
Bowie, et al., A Method to Identify Protien Sequences That Fold into a Known Three-Dimensional Structure, Science, Jul. 12, 1991, pp. 164-170, vol. 253.

(Continued)

*Primary Examiner* — Meera Naragajan

(57) ABSTRACT

The present disclosure relates generally to monoclonal antibodies that specifically bind to CD47, more specifically to CD47 antibodies that do not have significant platelet aggregation activity and do not have significant hemagglutination activity. Methods of generating these antibodies and methods of using these monoclonal antibodies as therapeutics are also provided.

17 Claims, 21 Drawing Sheets

Specification includes a Sequence Listing.

(56) References Cited

FOREIGN PATENT DOCUMENTS

| WO | 2009/085462 | A1 | | 7/2009 |
|---|---|---|---|---|
| WO | 2011/066501 | A1 | | 6/2011 |
| WO | 2011/143624 | A2 | | 11/2011 |
| WO | 2013119714 | A1 | | 8/2013 |
| WO | 2014/093678 | A2 | * | 6/2014 |
| WO | WO2014/123580 | | * | 8/2014 |

OTHER PUBLICATIONS

Brodeur, et al., Mouse-Human Myeloma Partners for the Production of Heterohybridomas, Production of Heterohybridomas, 1987, pp. 51-63, Chapter 4.
Carell, et al., A Solution-Phase Screening Procedure for the Isolation of Active Compounds from a Library of molecules**, Angew. Chem. Int .Ed. Engl., 1994, pp. 2061-2064, vol. 33 Issue 20.
Castagnoli, et al., Selection of Antibody Ligands from a Large Library of Oligopeptides Expressed on a Multivalent Exposition Vector, J. Mol. Biol., Jul. 26, 1991, pp. 301-310, vol. 222.
Chan, et al., Cancer stem cells in bladder cancer: a revisited and evolving concept, Current Opinion in Urology, 2010, pp. 393-397, vol. 20.
Chan, et al., Identification, molecular characterization, clinical prognosis, and therapeutic targeting of human bladder tumor-initiating cells, PNAS, Aug. 18, 2009, pp. 14016-14021, vol. 106 Issue 33.
Chao, et al., The CD47—SIRPa pathway in cancer immune evasion and potential therapeutic implications, Current Opinion in Immunology, Feb. 4, 2012, pp. 225-232, vol. 24.
Chiswell, et al., Phage antibodies: will new 'coliclonar' antibodies replace monoclonal antibodies?, TIBTECH, 1992, pp. 80-84, vol. 10.
Cho, et al., An Unnatural Biopolymer, Science, Sep. 3, 1993, pp. 1303-1305, vol. 261.
Chothia, et al., Canonical Structures for the Hypervariable Regions of Immunoglobulins, J. Mol. Biol . . . , Apr. 23, 1987, pp. 901-917, vol. 196.
Chothia, et al., Conformations of immunoglobulin hypervariable regions, Nature, 1989, pp. 877-883, vol. 342.
Cole, et al., HuM291, a Humanized Anti-CD3 Antibody, Is Immunosuppressive to T Cells While Exhibiting Reduced Mitogenicity in Vitro1, Immunogenetics, Aug. 27, 1999, pp. 563-571, vol. 68 Issue 4.
Cole, et al., The EBV-Hybridoma Technique and Its Application to Human Lung Cancer., Monoclonal Antibodies and cancer Therapy., 1985, pp. 77-96, Page Number.
Cote, et al., Generation of human monoclonal antibodies reactive with cellular antigens, Immunology, Apr. 1983, pp. 2026-2030, vol. 80.
Crell, et al., A Novel Procedure for the Synthesis of Libaries Containing Small Organic Molecules**, Angew. Int. Ed. Engl., 1994, pp. 2059-2061, vol. 33 Issue 20.
Crowther, et al., ELISA: Theory and Practice. Methods in Molecular Biology, vol. 42., TEM, 1996, pp. 352-353, vol. 7 Issue 9.
Cull, et al., Screening for Receptor Ligands Using Large Libraries of Peptides Linked to the C Terminus of the las Repressor, Proc. Natl. Acad. Sci., 1992, pp. 1865-1869, vol. 89.
Cwirla, et al., Peptides on phage: A vast library of peptides for identifying ligands, Proc. Nati. Acad., May 3, 1990, pp. 6378-6382, vol. 87.
Davidson, et al., A mode; system for in vivo gene transfer into the central nervous system using an adenoviral vector, Nature Genetics, 1993, pp. 219-223, vol. 3.
Davies, et al., Antibody-Antigen COMPLEXEX1, Annu.Rev. Biochem., 1990, pp. 439-473, vol. 59.
Deborah Wilkinson., Immunochemical techniques inspire development of new antibody purification methods, LabConsumer, Apr. 17, 2000, pp. 25-28, Page Number.

Dennis R. Burton, Commentary Phage display, Immunotechnology, Jul. 3, 1995, pp. 87-94, vol. 1.
Devlin, et al., Random Peptide Libraries: A Source of Specific Protein Binding Molecules, Science, Jul. 27, 1990, pp. 404-406, vol. 249 Issue 4967.
DeWitt, et al., "Diversomers": An approach to nonpeptide, nonoligomeric chemical diversity, Proc. Natl. Acad. Sci., Apr. 8, 1993, pp. 6909-6913, vol. 90.
Dorahy, et al., Stimulation of Platelet Activation and Aggregation by a Carboxyl-terminal Peptide from Thrombospondin Binding to the Integrin-associated Protein Receptor*, The Journal of Biological Chemistry, Aug. 31, 1996, pp. 1323-1330, vol. 272 Issue 2.
Erb, et al., Recursive deconvolution of combinatorial chemical libraries, Proc. Nati. Acad. Sci. USA, Aug. 3, 1994, pp. 11422-11426, vol. 91.
Fodor, et al., Multiplexed Biochemical Assays with Biological Chips, Nature, 1993, pp. 555-556, vol. 364, Nature Publishing Group.
Gallop, et al., Applications of Combinatorial Technologies to Drug Discovery. 1, Background and Peptide Combinatorial Libraries, Journal of Medicinal Chemistry, Apr. 29, 1994, pp. 1233-1251, vol. 37, No. 9.
Geller, et al., An HSV-1 Vector Expressing Tyrosine Hydroxylase Causes Production and Release of L-DOPA from Cultured Rat Striatal Cells, J. Neurochem., 1995, pp. 487-496, vol. 64 Issue 2.
Geller, et al., Infection of cultured central nervous system neurons with a defective herpes simplex virus 1 vector results in stable expression of *Escherichia coli* fi-galactosidase, Proc. Natl. Acad, Sci., Nov. 15, 1989, pp. 1149-1153, vol. 87.
Geller, et al., Long-term increases in neurotransmitter release from neuronal cells expressing a constitutively active adenylate cyclase from a herpes simplex virus type 1 vector, Proc. Natl. Acad. Sci., Apr. 28, 1993, pp. 7603-7607, vol. 90.
Goding, Production of Monoclonal Antibodies, Monoclonal Antibodies: Principles and Practice, 1986, pp. 59-103, Chapter 3.
Gorman, et al., The Rous sarcoma virus long terminal repeat is a strong promoter when introduced into a variety of eukaryotic cells by DNA-mediated transfection, Proc. Natl. Acad. Sci, Nov. 1982, pp. 6777-6781, vol. 79.
Green, et al., Antigen-specific human monoclonal antibodies from mice engineered with human Ig heavy and light chain YACs, Nature Genetics, 1994, pp. 13-21, vol. 7.
Grosschedl,et al., Cell-Type Specificity of Immunoglobulin Gene Expression is Regulated by at Least Three DNA Sequence Elements, Cell, Jul. 1985, pp. 885-897, vol. 41.
Hanes, et al., In vitro selection and evolution of functional proteins by using ribosome display, Proc. Natl. Acad. Sci., Nov. 7, 1996, pp. 4937-4942, vol. 94.
Hinz, et al., Thermodynamic Data for Biochemistry and Biotechnology, Analytical Biochemistry, 1987, pp. 309-310, vol. 162.
Hoogenboom, et al., Buliding Antibodies from their Genes, Immunological Reviews, 1992, pp. 41-68, Issue 130.
Houghten, et al., The Use of Synthetic Peptide Combinatorial Libraries for the Identification of Bioactive Peptides, Biotechniques, 1992, pp. 412-421, vol. 13, No. 3.
Huse, et al., Generation of a Large Combinatorial of the Immunoglobulin Repertoire in Phage Lambda, Research Article, 1989, pp. 1275-1281, vol. 246.
Jaiswal, et al., CD47 Is Upregulated on Circulating Hematopoietic Stem Cells and Leukemia Cells to Avoid Phagocytosis, Cell, 2009, pp. 271-285, vol. 138.
Jaiswal, et al., Macrophages as mediators of tumor immunosurveillance, Trends in Immunology, 2010, pp. 212-219, vol. 31.
Jamie K.Scott, Discovering peptide ligands using epitope libraries, TIBS, 1992, pp. 241-245, Page Number.
Kabat, et al., Sequences of Protiens of Immunological Intrest, Breifly Noted, 1963, pp. 323-323, page number.
Kaplitt, et al., Long-term gene expression and phenotypic correction using adeno-associated virus vectors in the mammalian brain, Nature Genetics, 1994, pp. 148-154, vol. 8.
Kit S. Lam, Application of Combinatorial Library Methods in Cancer Research and Drug Discovery, Anti-Cancer Drug Design, 1997, pp. 145-167, vol. 12.

(56) References Cited

OTHER PUBLICATIONS

Kiyoshi Ichihara, MD., Immunoassay, Jpn J Clin Pathol, 1993, pp. 737-742, vol. 41.
Kohler, et al., Continuous cultures of fused cells secreting antibody of predefined specificity, Nature, Aug. 7, 1975, pp. 495-497, vol. 256.
Kozbor, et al., A Human Hybrid Myeloma for Production of Human Monoclonal Antibodies, the Journal of Immunology, 1984, pp. 3001-3005, vol. 133, No. 6.
Kozbor, et al., A Human Hybrid Myeloma for Production of Human Monoclonal Antibodies, the Journal of Immunology, Dec. 1984, pp. 3001-3005, vol. 133, No. 6.
Kozbor, et al., The production of monoclonal antibodies from human lymphocytes, Immunology Today, 1983, pp. 72-79, vol. 4, No. 3.
Lam, et al., A New Type of Synthetic Peptide Library for Identifying Ligand-Binding Activity, Nature, Nov. 7, 1991, pp. 82-84, vol. 354.
Lim, et al., Expression using a defective herpes simplex virus (HSV-1) vector system, Supplied by the British Library, Apr. 13, 2018, pp. 263-283, Chapter 8.
Liu, et al., Production of a mouse-human chimeric monoclonal antibody to CD20 with potent Fc-dependent biologic activity., The Journal of Immunology, Aug. 18, 1987, pp. 3521-3526, vol. 139.
Liu,et al, Chimeric mouse-human IgGi antibody that can mediate lysis of cancer cells, Medical Sciences, May 1987, pp. 3439-3443, vol. 84.
Magnus Malmqvist., Biospecific interaction analysis using biosensor technology, Nature, 1993, pp. 186-187, vol. 361.
Marasco, et al., Design, intracellular expression, and activity of a human anti-human immunodeficiency virus type 1 gp120 single-chain antibody, Proc. Natl. Acad. Sci., Feb. 23, 1993, pp. 7869-7893, vol. 90.
Morrison, et al., High-flow microinfusion: tissue penetration and pharmacodynamics, Modeling in physiology, 1994, pp. R292-R305, vol. 266.
Munson, et al., Ligand: A Versatile Computerized Approach for Characterization of Ligand-Binding Systems, Anal. Biochem, Mar. 4, 1980, pp. 220-239, vol. 107.
Okayama, et al., A cDNA Cloning Vector That Permits Expression of cDNA Inserts in Mammalian Cells, Molecular and Cellular Biology, 1983, pp. 280-289, vol. 3, No. 2.
R Majeti., Monoclonal antibody therapy directed against human acute myeloid leukemia stem cells, Oncogene, Nov. 15, 2010, pp. 1009-1019, vol. 30.
Russell, et al., Retroviral Vectors displaying functional antibody fragments, Nucleic Acids Research, Feb. 5, 1993, pp. 1081-1085, vol. 21 Issue 5.
Salle, et al., An Adenovirus Vector for Gene Transfer into Neurons and Gila in the Brain, Science, Feb. 12, 1993, pp. 988-990, vol. 259.
Scott, et al., Searching for Peptide Ligands with an Epitope Library, Science, 1990, pp. 386-390, vol. 249.
Sherie L. Morrison, Success in specification, Nature, Apr. 28, 1994, pp. 812-813, vol. 368.
Shi, et al., De Novo Selection of High-Affinity Antibodies from Synthetic Fab Libraries Displayed on Phage as pIX Fusion Proteins, J. Mol. Biol., Jan. 28, 2010, pp. 385-396, vol. 397 Issue 2.
Thornton, et al., Prediction of progress at last, Nature, Nov. 14, 1991, pp. 105-106, vol. 354.
UniProtKB, RecName: Full=Leukocyte surface antigen CD47; AltName: Full=Antigenic surface determinant protein OA3; AltName: Full=Integrin-associated protein; Short=IAP; AltName: Full= Protein MER6; AltName: CD_antigen=CD47; Flags: Precursor, UniProtKB, Feb. 28, 2018, pp. 1-9, Q08722.1.
Uno, et al,, Antitumor activity of a monoclonal antibody aganist CD47 in xenograft models of human leukemia, Oncology Reports, Jan. 23, 2007, pp. 1189-1194, vol. 17.
Winter, et al., Humanized antibodies, tmmunolo~ Today, 1993, pp. 243-246, vol. 14 Issue 6.
Wright, et al., Genetically Engineered Antibodies: Progress and Prospects, Critical Reviews in Immunology, 1992, pp. 125-168, vol. 2 Issue 3,4.
Yang, et al., Cellular and Humoral Immune Responses to Viral Antigens Create Barriers to Lung-Directed Gene Therapy with Recombinant Adenoviruses, Journal of Virology, Dec. 16, 1994, pp. 2004-2015, vol. 69 Issue 4.
Zuckermann, et al., Discovery of Nanomolar Ligands for 7-Transmembrane G-Protein-Coupled Receptors for a Diverse N-(Substituted)Glycine Peptoid Library, J. Med. Chem., 1994, pp. 2678-2685, vol. 37.

* cited by examiner

Figure 6

Epitopes

```
                    .  .               . ...  ..  .           . .
C47B161_epitope   1 QLLFNKTKSVEFTFGNDTVVIPCFVTNMEAQNTTEVYVKWKFKGRDIYTFDGALNKSTVPTDFSS  65
C47B167_epitope   1 QLLFNKTKSVEFTFGNDTVVIPCFVTNMEAQNTTEVYVKWKFKGRDIYTFDGALNKSTVPTDFSS  65
C47B222_epitope   1 QLLFNKTKSVEFTFGNDTVVIPCFVTNMEAQNTTEVYVKWKFKGRDIYTFDGALNKSTVPTDFSS  65
C47B227_epitope   1 QLLFNKTKSVEFTFGNDTVVIPCFVTNMEAQNTTEVYVKWKFKGRDIYTFDGALNKSTVPTDFSS  65
B6H12.2_epitope   1 QLLFNKTKSVEFTFGNDTVVIPCFVTNMEAQNTTEVYVKWKFKGRDIYTFDGALNKSTVPTDFSS  65

.  . .......  .
C47B161_epitope  66 AKIEVSQLLKGDASLKMDKSDAVSHTGNYTCEVTELTREGETIIELKYRVVSWFSPNEHHHHHH  129
C47B167_epitope  66 AKIEVSQLLKGDASLKMDKSDAVSHTGNYTCEVTELTREGETIIELKYRVVSWFSPNEHHHHHH  129
C47B222_epitope  66 AKIEVSQLLKGDASLKMDKSDAVSHTGNYTCEVTELTREGETIIELKYRVVSWFSPNEHHHHHH  129
C47B227_epitope  66 AKIEVSQLLKGDASLKMDKSDAVSHTGNYTCEVTELTREGETIIELKYRVVSWFSPNEHHHHHH  129
B6H12.2_epitope  66 AKIEVSQLLKGDASLKMDKSDAVSHTGNYTCEVTELTREGETIIELKYRVVSWFSPNEHHHHHH  129
```

Paratopes

```
                                    CDR-L1              CDR-L2
C47B161_LC    1 DIVMTQSPLSLPVTPGEPASISCRSRQSIVHTNRYTYLAWYLQKPGQSPQLLIYKVSNRFSGVPDRFSGSGSG   73
C47B167_LC    1 EIVLTQSPATLSLSPGERATLSCRASSSVS------MHWYQQKPGQAPRLLIYDTSRLASGIPARFSGSGSG   67
C47B222_LC    1 EIVLTQSPATLSLSPGERATLSCRASQSVNN-----RLAWYQQKPGQAPRLLIHWASTRAIGIPARFSGSGSG  68
C47B227_LC    1 EIVLTQSPATLSLSPGERATLSCRASQSVGS-----RLAWYQQKPGQAPRLLIYWASTRATGIPARFSGSGSG  68
B6H12.2_LC    1 DIVMTQSPATLSVTPGDRVSLSCRASQTISS-----YLHWYQQKSHESPRLLIKFASQSISGIPSRFSGSGSG  68

CDR-L3
C47B161_LC   74 TDFTLKISRVEAEDVGVYYCFQGSHVPYTFGGGTKLEIKRTVAAPSVFIFPPSDEQLKSGTASVVCLLNNFYP  146
C47B167_LC   68 TDFTLTISSLEPEDFAVYYCQQWRSNPYTFGGGTKVEIKRTVAAPSVFIFPPSDEQLKSGTASVVCLLNNFYP  140
C47B222_LC   69 TDFTLTISSLEPEDFAVYYCQQGASWPFTFGQGTKVEIKRTVAAPSVFIFPPSDEQLKSGTASVVCLLNNFYP  141
C47B227_LC   69 TDFTLTISSLEPEDFAVYYCQQGAYWPFTFGQGTKVEIKRTVAAPSVFIFPPSDEQLKSGTASVVCLLNNFYP  141
B6H12.2_LC   69 SDFTLSINSVEPEDVGVYYCQNGHGFPRTFGGGTKLEIKRTVAAPSVFIFPPSDEQLKSGTASVVCLLNNFYP  141

C47B161_LC  147 REAKVQWKVDNALQSGNSQESVTEQDSKDSTYSLSSTLTLSKADYEKHKVYACEVTHQGLSSPVTKSFNRGEC  219
C47B167_LC  141 REAKVQWKVDNALQSGNSQESVTEQDSKDSTYSLSSTLTLSKADYEKHKVYACEVTHQGLSSPVTKSFNRGEC  213
C47B222_LC  142 REAKVQWKVDNALQSGNSQESVTEQDSKDSTYSLSSTLTLSKADYEKHKVYACEVTHQGLSSPVTKSFNRGEC  214
C47B227_LC  142 REAKVQWKVDNALQSGNSQESVTEQDSKDSTYSLSSTLTLSKADYEKHKVYACEVTHQGLSSPVTKSFNRGEC  214
B6H12.2_LC  142 REAKVQWKVDNALQSGNSQESVTEQDSKDSTYSLSSTLTLSKADYEKHKVYACEVTHQGLSSPVTKSFNRGEC  214

CDR-H1                CDR-H2
C47B161_HC    1 QVQLVQSGAEVKKPGASVKVSCKASGYTFTDYNMHWVRQAPGQRLEWMGDIYPYNGGTGYNQKFKGRVTITRDTSAST  78
C47B167_HC    1 EVQLVQSGAEVKKPGESLKISCKGSGYTFTSYWMQWVRQMPGKGLEWMGEINPSNGRTDYNEKFRGQVTISADKSIST  78
C47B222_HC    1 EVQLVQSGAEVKKPGESLKISCKGSGYSFTQYWIGWVRQMPGKGLEWMGIIYPGDSDTRYSPSFQGQVTISADKSIST  78
C47B227_HC    1 EVQLVQSGAEVKKPGESLKISCKGSGYSFDDYWIGWVRQMPGKGLEWMGIIYPGDSDTRYSPSFQGQVTISADKSIST  78
B6H12.2_HC    1 EVKLVESGGDLVKPGGSLKLSCAASGFTFSGFGMSWVRQTPDKRLEWVATITSGGTYTYYPDSVKGRFTISRDNAKNT  78

CDR-H3
C47B161_HC   79 AYMELSSLRSEDTAVYYCARGG-------WHEMDSWGQGTLVTVSSASTKGPSVFPLAPSSKSTSGGTAALGCLVKDY  149
C47B167_HC   79 AYLQWSSLKASDTAMYYCARQGGSGYGNSYGFFDVWGQGTTVTVSSASTKGPSVFPLAPSSKSTSGGTAALGCLVKDY  156
C47B222_HC   79 AYLQWSSLKASDTAVYYCARVG----RFASHQLDYWGQGTLVTVSSASTKGPSVFPLAPSSKSTSGGTAALGCLVKDY  152
C47B227_HC   79 AYLQWSSLKASDTAVYYCARVG----RFASHQLDYWGQGTLVTVSSASTKGPSVFPLAPSSKSTSGGTAALGCLVKDY  152
B6H12.2_HC   79 LYLQIDSLKSEDTAIYFCARSLAG------NAMDYWGQGTSVTVSSASTKGPSVFPLAPSSKSTSGGTAALGCLVKDY  150

C47B161_HC  150 FPEPVTVSWNSGALTSGVHTFPAVLQSSGLYSLSSVVTVPSSSLGTQTYICNVNHKPSNTKVDKKVEPKSCHHHHHH  226
C47B167_HC  157 FPEPVTVSWNSGALTSGVHTFPAVLQSSGLYSLSSVVTVPSSSLGTQTYICNVNHKPSNTKVDKKVEPKSCHHHHHH  233
C47B222_HC  153 FPEPVTVSWNSGALTSGVHTFPAVLQSSGLYSLSSVVTVPSSSLGTQTYICNVNHKPSNTKVDKKVEPKSCHHHHHH  229
C47B227_HC  153 FPEPVTVSWNSGALTSGVHTFPAVLQSSGLYSLSSVVTVPSSSLGTQTYICNVNHKPSNTKVDKKVEPKSCHHHHHH  229
B6H12.2_HC  151 FPEPVTVSWNSGALTSGVHTFPAVLQSSGLYSLSSVVTVPSSSLGTQTYICNVNHKPSNTKVDKKVEPKSCHHHHHH  227
```

Figure 7A
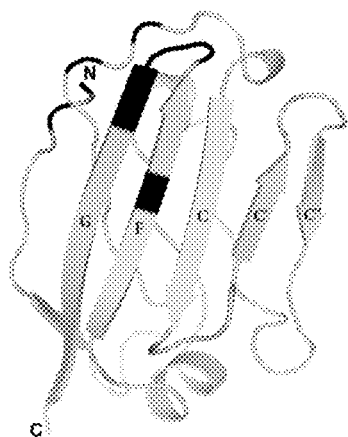
Figure 7B
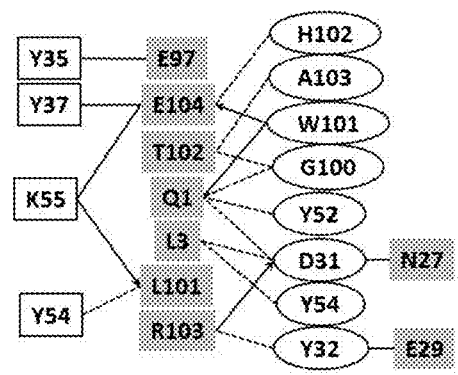
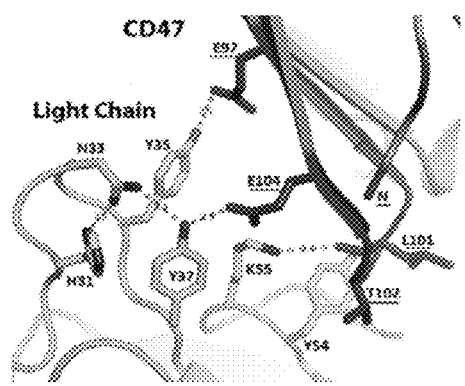
Figure 7C
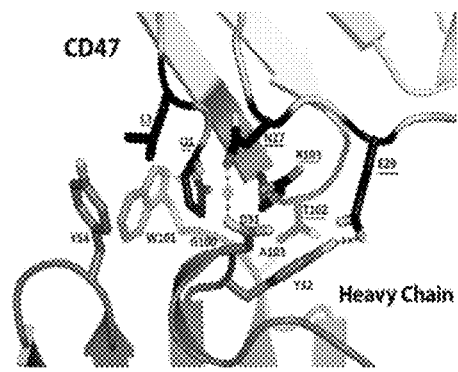
Figure 7D Figure 10A
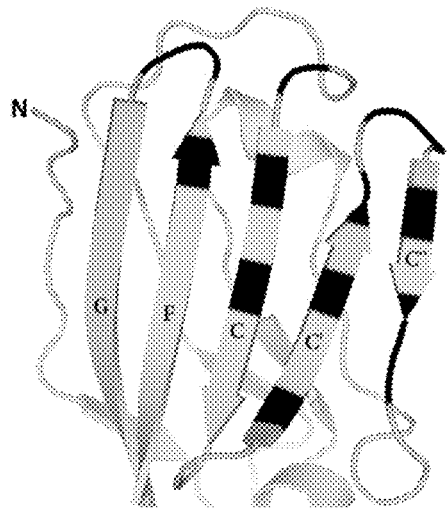
Figure 10B
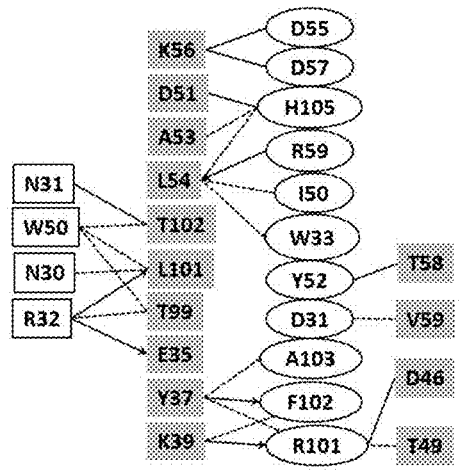
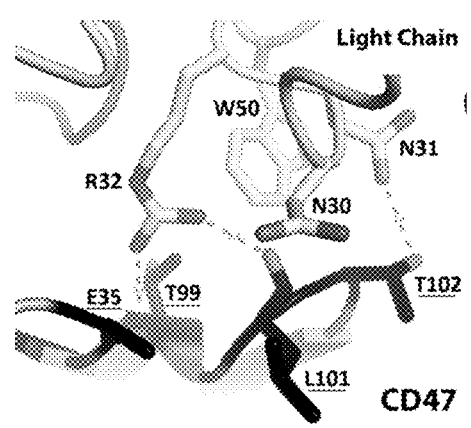
Figure 10C
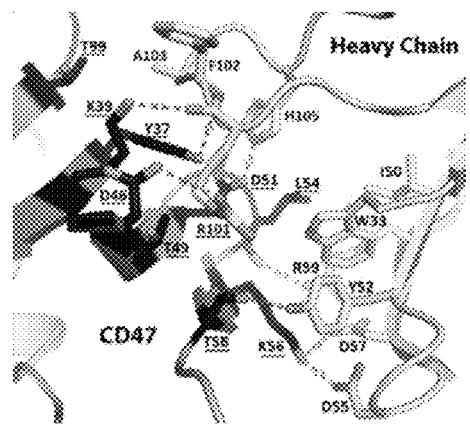
Figure 10D Figure 11A
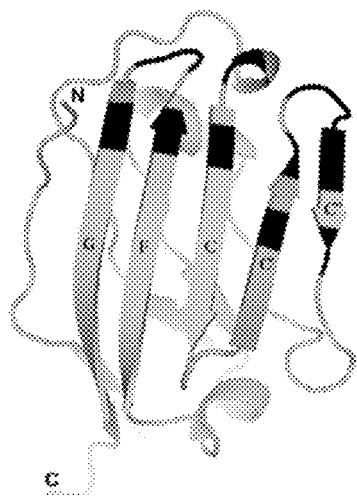
Figure 11B
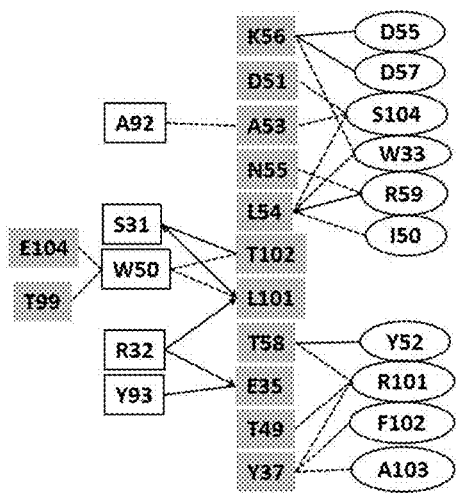
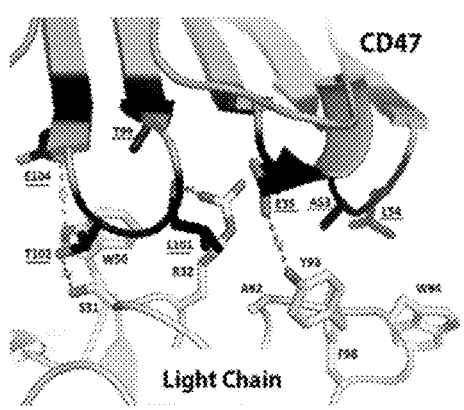
Figure 11C
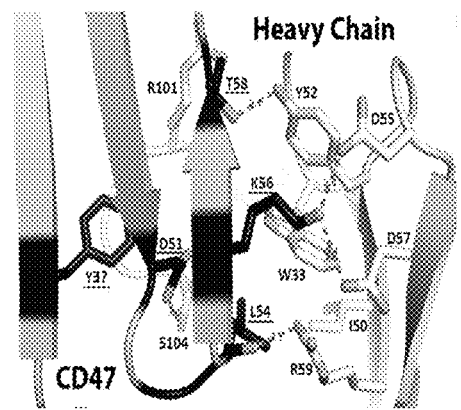
Figure 11D

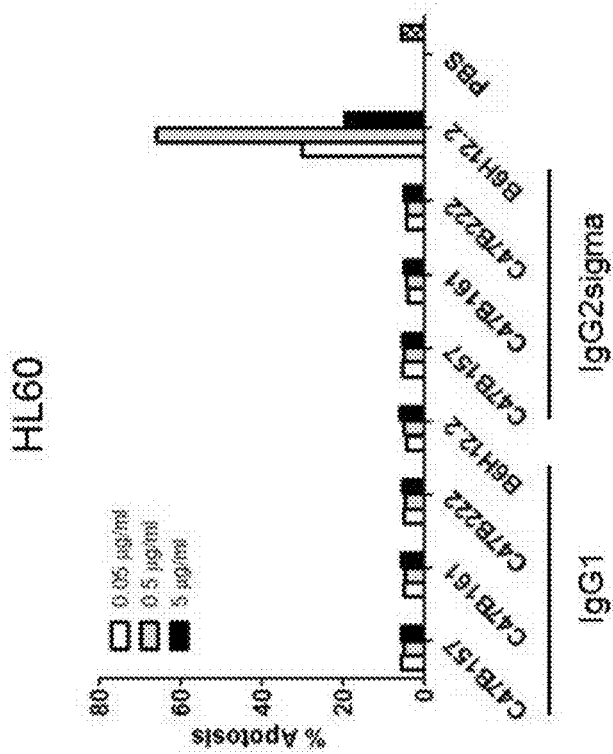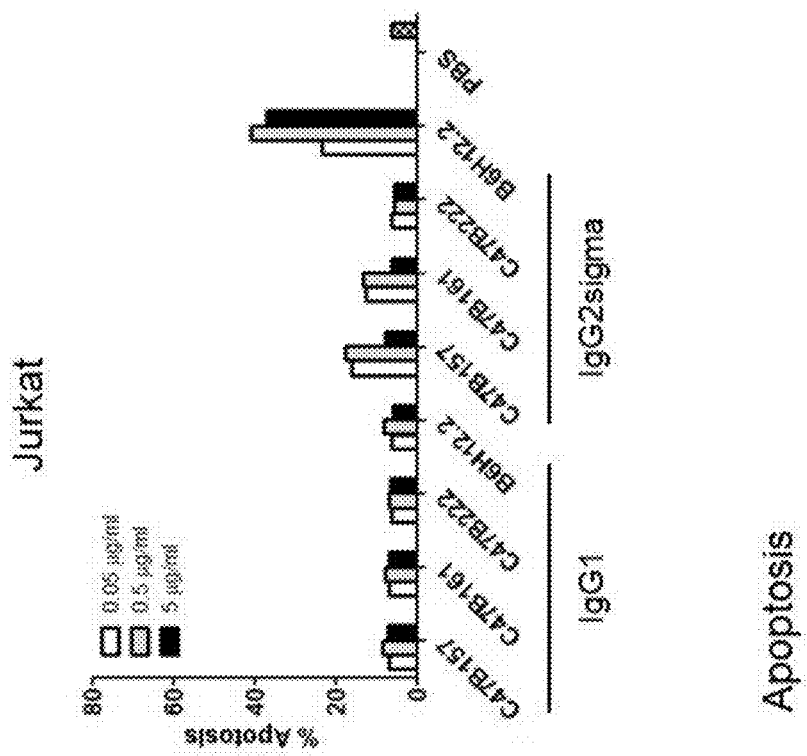
Figure 15B
Figure 15A
Apoptosis

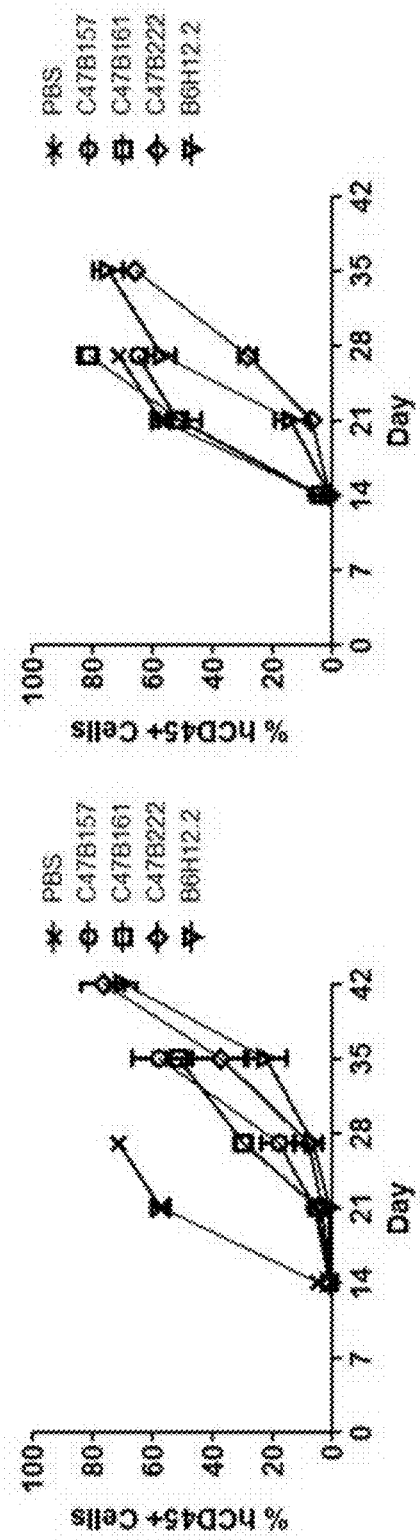
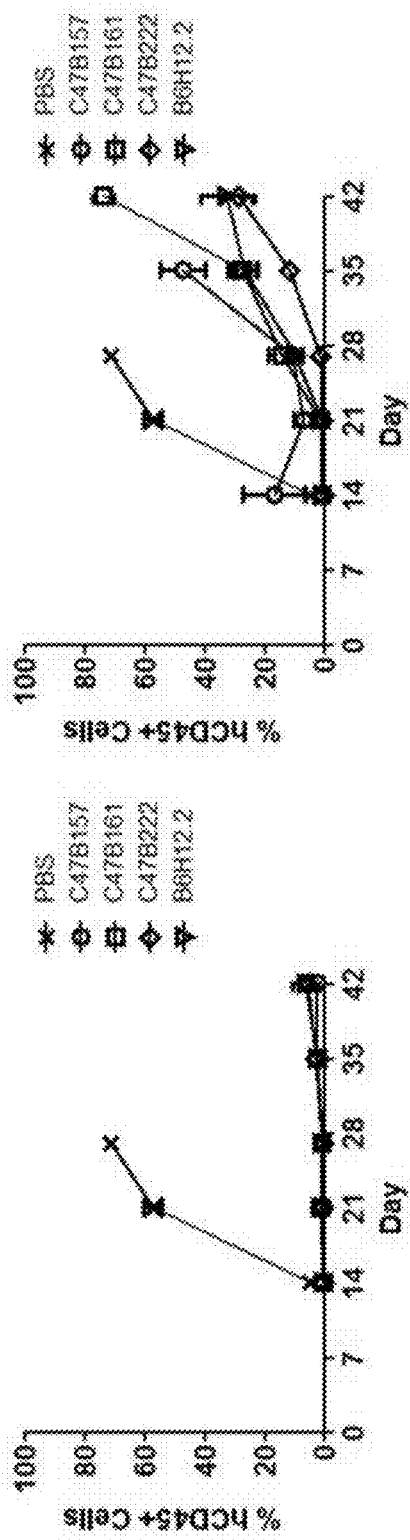
Figure 18A, Figure 18B, Figure 18C, Figure 18D

In vivo Kasumi-3/NSG mice

SEQUENCE LISTING

<160> NUMBER OF SEQ ID NOS: 68

<210> SEQ ID NO 1
<211> LENGTH: 330
<212> TYPE: PRT

<213> ORGANISM: Homo sapiens

<400> SEQUENCE: 1

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 2
<211> LENGTH: 326
<212> TYPE: PRT
<213> ORGANISM: Homo sapiens

<400> SEQUENCE: 2

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
```

-continued

```
                20                  25                  30
Phe Pro Glu Pro Val Thr Val Ser Trp Asn Ser Gly Ala Leu Thr Ser
             35                  40                  45
Gly Val His Thr Phe Pro Ala Val Leu Gln Ser Ser Gly Leu Tyr Ser
         50                  55                  60
Leu Ser Ser Val Val Thr Val Pro Ser Ser Asn Phe Gly Thr Gln Thr
 65                  70                  75                  80
Tyr Thr Cys Asn Val Asp His Lys Pro Ser Asn Thr Lys Val Asp Lys
                 85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
        115                 120                 125
Thr Leu Met Ile Ser Arg Thr Pro Glu Val Thr Cys Val Val Val Asp
    130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
            325

<210> SEQ ID NO 3
<211> LENGTH: 326
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
 1               5                  10                  15
Ser Thr Ser Glu Ser Thr Ala Ala Leu Gly Cys Leu Val Lys Asp Tyr
             20                  25                  30
Phe Pro Glu Pro Val Thr Val Ser Trp Asn Ser Gly Ala Leu Thr Ser
         35                  40                  45
Gly Val His Thr Phe Pro Ala Val Leu Gln Ser Ser Gly Leu Tyr Ser
     50                  55                  60
```

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Ala Ala Ala Ser Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Ala Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 4
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Gly Leu Glu Trp Met
        35                  40                  45

Gly Asp Ile Tyr Pro Tyr Asn Gly Gly Thr Gly Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
                    85                  90                  95

Ala Arg Gly Gly Trp His Ala Met Asp Ser Trp Gly Gln Gly Thr Leu
                100                 105                 110

Val Thr Val Ser Ser
        115

<210> SEQ ID NO 5
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Arg Leu Glu Trp Met
            35                  40                  45

Gly Asp Ile Tyr Pro Tyr Asn Gly Gly Thr Gly Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp His Ala Met Asp Ser Trp Gly Gln Gly Thr Leu
                100                 105                 110

Val Thr Val Ser Ser
        115

<210> SEQ ID NO 6
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Val Gly Arg Phe Ala Ser His Gln Leu Asp Tyr Trp Gly Gln
                100                 105                 110

Gly Thr Leu Val Thr Val Ser Ser
        115                 120
```

<210> SEQ ID NO 7
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Asp Ile Val Met Thr Gln Ser Pro Leu Ser Leu Pro Val Thr Pro Gly
1               5                   10                  15
Glu Pro Ala Ser Ile Ser Cys Arg Ser Arg Gln Ser Ile Val His Thr
            20                  25                  30
Asn Arg Tyr Thr Tyr Leu Ala Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Val Pro Tyr Thr Phe Gly Gly Gly Thr Lys Leu Glu Ile Lys
            100                 105                 110
```

<210> SEQ ID NO 8
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 8

```
Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Val Asn Asn Arg
            20                  25                  30
Leu Ala Trp Tyr Gln Gln Lys Pro Gly Gln Ala Pro Arg Leu Leu Ile
        35                  40                  45
His Trp Ala Ser Thr Arg Ala Ile Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Gly Ala Ser Trp Pro Phe
                85                  90                  95
Thr Phe Gly Gln Gly Thr Lys Val Glu Ile Lys
            100                 105
```

<210> SEQ ID NO 9
<211> LENGTH: 5
<212> TYPE: PRT
<213> ORGANISM: Mus sp.

<400> SEQUENCE: 9

```
Asp Tyr Asn Met His
1               5
```

```
<210> SEQ ID NO 10
<211> LENGTH: 5
<212> TYPE: PRT
<213> ORGANISM: Mus sp.

<400> SEQUENCE: 10

Asp Tyr Trp Ile Gly
1               5

<210> SEQ ID NO 11
<211> LENGTH: 17
<212> TYPE: PRT
<213> ORGANISM: Mus sp.

<400> SEQUENCE: 11

Asp Ile Tyr Pro Tyr Asn Gly Gly Thr Gly Tyr Asn Gln Lys Phe Lys
1               5                   10                  15

Gly

<210> SEQ ID NO 12
<211> LENGTH: 17
<212> TYPE: PRT
<213> ORGANISM: Mus sp.

<400> SEQUENCE: 12

Ile Ile Tyr Pro Gly Asp Ser Asp Thr Arg Tyr Ser Pro Ser Phe Gln
1               5                   10                  15

Gly

<210> SEQ ID NO 13
<211> LENGTH: 8
<212> TYPE: PRT
<213> ORGANISM: Mus sp.

<400> SEQUENCE: 13

Gly Gly Trp His Ala Met Asp Ser
1               5

<210> SEQ ID NO 14
<211> LENGTH: 11
<212> TYPE: PRT
<213> ORGANISM: Mus sp.

<400> SEQUENCE: 14

Val Gly Arg Phe Ala Ser His Gln Leu Asp Tyr
1               5                   10

<210> SEQ ID NO 15
<211> LENGTH: 16
<212> TYPE: PRT
<213> ORGANISM: Mus sp.

<400> SEQUENCE: 15

Arg Ser Arg Gln Ser Ile Val His Thr Asn Arg Tyr Thr Tyr Leu Ala
1               5                   10                  15

<210> SEQ ID NO 16
<211> LENGTH: 11
<212> TYPE: PRT
<213> ORGANISM: Mus sp.

<400> SEQUENCE: 16

Arg Ala Ser Gln Ser Val Asn Asn Arg Leu Ala
1               5                   10
```

<210> SEQ ID NO 17
<211> LENGTH: 7
<212> TYPE: PRT
<213> ORGANISM: Mus sp.

<400> SEQUENCE: 17

Lys Val Ser Asn Arg Phe Ser
1               5

<210> SEQ ID NO 18
<211> LENGTH: 7
<212> TYPE: PRT
<213> ORGANISM: Mus sp.

<400> SEQUENCE: 18

Trp Ala Ser Thr Arg Ala Ile
1               5

<210> SEQ ID NO 19
<211> LENGTH: 9
<212> TYPE: PRT
<213> ORGANISM: Mus sp.

<400> SEQUENCE: 19

Phe Gln Gly Ser His Val Pro Tyr Thr
1               5

<210> SEQ ID NO 20
<211> LENGTH: 9
<212> TYPE: PRT
<213> ORGANISM: Mus sp.

<400> SEQUENCE: 20

Gln Gln Gly Ala Ser Trp Pro Phe Thr
1               5

<210> SEQ ID NO 21
<211> LENGTH: 323
<212> TYPE: PRT
<213> ORGANISM: Homo sapiens

<400> SEQUENCE: 21

Met Trp Pro Leu Val Ala Ala Leu Leu Leu Gly Ser Ala Cys Cys Gly
1               5                   10                  15

Ser Ala Gln Leu Leu Phe Asn Lys Thr Lys Ser Val Glu Phe Thr Phe
                20                  25                  30

Cys Asn Asp Thr Val Val Ile Pro Cys Phe Val Thr Asn Met Glu Ala
            35                  40                  45

Gln Asn Thr Thr Glu Val Tyr Val Lys Trp Lys Phe Lys Gly Arg Asp
        50                  55                  60

Ile Tyr Thr Phe Asp Gly Ala Leu Asn Lys Ser Thr Val Pro Thr Asp
65                  70                  75                  80

Phe Ser Ser Ala Lys Ile Glu Val Ser Gln Leu Leu Lys Gly Asp Ala
                85                  90                  95

Ser Leu Lys Met Asp Lys Ser Asp Ala Val Ser His Thr Gly Asn Tyr
            100                 105                 110

Thr Cys Glu Val Thr Glu Leu Thr Arg Glu Gly Glu Thr Ile Ile Glu
        115                 120                 125

Leu Lys Tyr Arg Val Val Ser Trp Phe Ser Pro Asn Glu Asn Ile Leu
    130                 135                 140

```
Ile Val Ile Phe Pro Ile Phe Ala Ile Leu Leu Phe Trp Gly Gln Phe
145                 150                 155                 160

Gly Ile Lys Thr Leu Lys Tyr Arg Ser Gly Met Asp Glu Lys Thr
                165                 170                 175

Ile Ala Leu Leu Val Ala Gly Leu Val Ile Thr Val Ile Val Ile Val
            180                 185                 190

Gly Ala Ile Leu Phe Val Pro Gly Glu Tyr Ser Leu Lys Asn Ala Thr
            195                 200                 205

Gly Leu Gly Leu Ile Val Thr Ser Thr Gly Ile Leu Ile Leu Leu His
        210                 215                 220

Tyr Tyr Val Phe Ser Thr Ala Ile Gly Leu Thr Ser Phe Val Ile Ala
225                 230                 235                 240

Ile Leu Val Ile Gln Val Ile Ala Tyr Ile Leu Ala Val Val Gly Leu
                245                 250                 255

Ser Leu Cys Ile Ala Ala Cys Ile Pro Met His Gly Pro Leu Leu Ile
            260                 265                 270

Ser Gly Leu Ser Ile Leu Ala Leu Ala Gln Leu Leu Gly Leu Val Tyr
        275                 280                 285

Met Lys Phe Val Ala Ser Asn Gln Lys Thr Ile Gln Pro Pro Arg Lys
        290                 295                 300

Ala Val Glu Glu Pro Leu Asn Ala Phe Lys Glu Ser Lys Gly Met Met
305                 310                 315                 320

Asn Asp Glu

<210> SEQ ID NO 22
<211> LENGTH: 123
<212> TYPE: PRT
<213> ORGANISM: Homo sapiens

<400> SEQUENCE: 22

Gln Leu Leu Phe Asn Lys Thr Lys Ser Val Glu Phe Thr Phe Cys Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu
        115                 120

<210> SEQ ID NO 23
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
```
caaagtatac aggcccaggt gcagctggtg cagag                    35

<210> SEQ ID NO 24
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
caaagtatac aggccgaagt gcagctgctg gaaag                    35

<210> SEQ ID NO 25
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
caaagtatac aggccgaagt gcagctggtg cagagc                   36

<210> SEQ ID NO 26
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
gcccttggtg gaggcgctgc tcacggtcac cag                      33

<210> SEQ ID NO 27
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
caaagtatcc aagcagaaat tgtgctgacc cagag                    35

<210> SEQ ID NO 28
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
caaagtatcc aagcagatat tcagatgacc cagagc                   36

<210> SEQ ID NO 29
<211> LENGTH: 36
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 29
tgcagccacc gtacgtttaa tttccacttt ggtgcc                                   36

<210> SEQ ID NO 30
<211> LENGTH: 117
<212> TYPE: PRT
<213> ORGANISM: Mus sp.

<400> SEQUENCE: 30

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30

Asn Met His Trp Val Lys Gln Ser His Gly Lys Ser Leu Glu Trp Ile
            35                  40                  45

Gly Asp Ile Tyr Pro Tyr Asn Gly Gly Thr Gly Tyr Asn Gln Lys Phe
        50                  55                  60

Lys Ser Lys Ala Thr Leu Thr Val Asp Asn Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Gly Trp His Ala Met Asp Ser Trp Gly Gln Gly Thr Ser
            100                 105                 110

Val Thr Val Ser Ser
        115

<210> SEQ ID NO 31
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
                20                  25                  30

Asn Met His Trp Val Arg Gln Ala Pro Gly Gln Gly Leu Glu Trp Met
            35                  40                  45

Gly Asp Ile Tyr Pro Tyr Asn Gly Gly Thr Gly Tyr Asn Gln Lys Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp His Ala Met Asp Ser Trp Gly Gln Gly Thr Leu
            100                 105                 110

Val Thr Val Ser Ser
        115

<210> SEQ ID NO 32
<211> LENGTH: 117
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Glu Val Gln Leu Val Gln Ser Gly Ala Glu Val Lys Pro Gly Glu
1               5                   10                  15

Ser Leu Lys Ile Ser Cys Lys Gly Ser Gly Tyr Thr Phe Thr Asp Tyr
            20                  25                  30

Asn Met His Trp Val Arg Gln Met Pro Gly Lys Gly Leu Glu Trp Met
        35                  40                  45

Gly Asp Ile Tyr Pro Tyr Asn Gly Gly Thr Gly Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Gly Trp His Ala Met Asp Ser Trp Gly Gln Gly Thr Leu
            100                 105                 110

Val Thr Val Ser Ser
        115

<210> SEQ ID NO 33
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Ile Val Met Thr Gln Ser Pro Asp Ser Leu Ala Val Ser Leu Gly
1               5                   10                  15

Glu Arg Ala Thr Ile Asn Cys Arg Ser Arg Gln Ser Ile Val His Thr
            20                  25                  30

Asn Arg Tyr Thr Tyr Leu Ala Trp Tyr Gln Gln Lys Pro Gly Gln Pro
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 34
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Glu Ile Val Leu Thr Gln Ser Pro Ala Thr Leu Ser Leu Ser Pro Gly
```

```
1               5                   10                  15
Glu Arg Ala Thr Leu Ser Cys Arg Ser Arg Gln Ser Ile Val His Thr
            20                  25                  30

Asn Arg Tyr Thr Tyr Leu Ala Trp Tyr Gln Gln Lys Pro Gly Gln Ala
            35                  40                  45

Pro Arg Leu Leu Ile Tyr Lys Val Ser Asn Arg Phe Ser Gly Ile Pro
            50                  55                  60

Ala Arg Phe Ser Gly Ser Gly Ser Gly Thr Asp Phe Thr Leu Thr Ile
65                  70                  75                  80

Ser Ser Leu Glu Pro Glu Asp Phe Ala Val Tyr Tyr Cys Phe Gln Gly
                85                  90                  95

Ser His Val Pro Tyr Thr Phe Gly Gly Gly Thr Lys Leu Glu Ile Lys
                100                 105                 110
```

<210> SEQ ID NO 35
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
            50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Gly Arg Phe Ala Ser His Gln Leu Asp Tyr Trp Gly Gln
                100                 105                 110

Gly Thr Leu Val Thr Val Ser Ser
            115                 120
```

<210> SEQ ID NO 36
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Lys Ala
            20                  25                  30

Leu Ala Trp Tyr Gln Gln Lys Pro Gly Gln Ala Pro Arg Leu Leu Ile
            35                  40                  45

Tyr Gly Ala Ser Asn Arg Ala Thr Gly Ile Pro Ala Arg Phe Ser Gly
            50                  55                  60
```

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Lys Gly Trp Pro Phe
                85                  90                  95

Thr Phe Gly Gln Gly Thr Lys Val Glu Ile Lys
            100                 105

<210> SEQ ID NO 37
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 37

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Asp Ser
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Val Gly Arg Phe Ala Ser His Gln Leu Asp Tyr Trp Gly Gln
            100                 105                 110

Gly Thr Leu Val Thr Val Ser Ser
        115                 120

<210> SEQ ID NO 38
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 38

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Ser
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Val Gly Arg Phe Ala Ser His Gln Leu Asp Tyr Trp Gly Gln
            100                 105                 110

```
Gly Thr Leu Val Thr Val Ser Ser
        115                 120
```

<210> SEQ ID NO 39
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Asp Ala
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Val Gly Arg Phe Ala Ser His Gln Leu Asp Tyr Trp Gly Gln
            100                 105                 110

Gly Thr Leu Val Thr Val Ser Ser
        115                 120
```

<210> SEQ ID NO 40
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 40

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asp Asp
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Val Gly Arg Phe Ala Ser His Gln Leu Asp Tyr Trp Gly Gln
            100                 105                 110

Gly Thr Leu Val Thr Val Ser Ser
        115                 120
```

<210> SEQ ID NO 41
<211> LENGTH: 120
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 41

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Asp Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Val Gly Arg Phe Ala Ser His Gln Leu Asp Tyr Trp Gly Gln
            100                 105                 110

Gly Thr Leu Val Thr Val Ser Ser
        115                 120
```

<210> SEQ ID NO 42
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Val Gly Arg Phe Ala Ser His Gln Leu Asp Tyr Trp Gly Gln
            100                 105                 110

Gly Thr Leu Val Thr Val Ser Ser
        115                 120
```

<210> SEQ ID NO 43
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Val Gly Arg Phe Ala Ser His Gln Leu Asp Tyr Trp Gly Gln
                100                 105                 110

Gly Thr Leu Val Thr Val Ser Ser
            115                 120

<210> SEQ ID NO 44
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Asp Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Val Gly Arg Phe Ala Ser His Gln Leu Asp Tyr Trp Gly Gln
                100                 105                 110

Gly Thr Leu Val Thr Val Ser Ser
            115                 120

<210> SEQ ID NO 45
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Lys Asp Asp
            20                  25                  30

```
Trp Ile Gly Trp Val Arg Gln Met Pro Gly Lys Gly Leu Glu Trp Met
                35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Val Gly Arg Phe Ala Ser His Gln Leu Asp Tyr Trp Gly Gln
                100                 105                 110

Gly Thr Leu Val Thr Val Ser Ser
        115                 120

<210> SEQ ID NO 46
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Arg
                20                  25                  30

Leu Ala Trp Tyr Gln Gln Lys Pro Gly Gln Ala Pro Arg Leu Leu Ile
                35                  40                  45

Tyr Trp Ala Ser Thr Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Ala Tyr Trp Pro Phe
                85                  90                  95

Thr Phe Gly Gln Gly Thr Lys Val Glu Ile Lys
                100                 105

<210> SEQ ID NO 47
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Arg
                20                  25                  30

Leu Ala Trp Tyr Gln Gln Lys Pro Gly Gln Ala Pro Arg Leu Leu Ile
                35                  40                  45

Tyr Gly Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Arg Ser Trp Pro Phe
```

85                  90                  95

Thr Phe Gly Gln Gly Thr Lys Val Glu Ile Lys
                100                 105

<210> SEQ ID NO 48
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asn Arg
            20                  25                  30

Gln Ala Trp Tyr Gln Gln Lys Pro Gly Gln Ala Pro Arg Leu Leu Ile
        35                  40                  45

His Ser Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Arg Ser Trp Pro Phe
                85                  90                  95

Thr Phe Gly Gln Gly Thr Lys Val Glu Ile Lys
                100                 105

<210> SEQ ID NO 49
<211> LENGTH: 123
<212> TYPE: PRT
<213> ORGANISM: Homo sapiens

<400> SEQUENCE: 49

Gln Leu Leu Phe Asn Lys Thr Lys Ser Val Glu Phe Thr Phe Gly Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
                100                 105                 110

Tyr Arg Val Val Ser Trp Phe Ser Pro Asn Glu
            115                 120

<210> SEQ ID NO 50
<211> LENGTH: 124
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Trp Met Gln Trp Val Arg Gln Met Pro Gly Lys Gly Leu Glu Trp Met
        35                  40                  45

Gly Glu Ile Asn Pro Ser Asn Gly Arg Thr Asp Tyr Asn Glu Lys Phe
    50                  55                  60

Arg Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Gly Ser Gly Tyr Gly Asn Ser Tyr Gly Phe Phe Asp
            100                 105                 110

Val Trp Gly Gln Gly Thr Thr Val Thr Val Ser Ser
            115                 120

<210> SEQ ID NO 51
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Arg Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ser Asn Pro Tyr Thr
                85                  90                  95

Phe Gly Gly Gly Thr Lys Val Glu Ile Lys
            100                 105

<210> SEQ ID NO 52
<211> LENGTH: 118
<212> TYPE: PRT
<213> ORGANISM: Mus sp.

<400> SEQUENCE: 52

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Ser Val Thr Val Ser Ser
            115

<210> SEQ ID NO 53
<211> LENGTH: 107
<212> TYPE: PRT
<213> ORGANISM: Mus sp.

<400> SEQUENCE: 53

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Gly Phe Pro Arg
                85                  90                  95

Thr Phe Gly Gly Gly Thr Lys Leu Glu Ile Lys
            100                 105

<210> SEQ ID NO 54
<211> LENGTH: 112
<212> TYPE: PRT
<213> ORGANISM: Mus sp.

<400> SEQUENCE: 54

Asp Val Val Met Thr Gln Thr Pro Leu Ser Leu Pro Val Ser Leu Gly
1               5                   10                  15

Asp Gln Ala Ser Ile Ser Cys Arg Ser Arg Gln Ser Ile Val His Thr
            20                  25                  30

Asn Arg Tyr Thr Tyr Leu Ala Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

<210> SEQ ID NO 55
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic 6xHis tag"

<400> SEQUENCE: 55

His His His His His His
1               5

<210> SEQ ID NO 56
<211> LENGTH: 129
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Gln Leu Leu Phe Asn Lys Thr Lys Ser Val Glu Phe Thr Phe Gly Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
        35                  40                  45

Thr Phe Asp Gly Ala Leu Asn Lys Ser Thr Val Pro Thr Asp Phe Ser
    50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
            100                 105                 110

Tyr Arg Val Val Ser Trp Phe Ser Pro Asn Glu His His His His His
        115                 120                 125

His

<210> SEQ ID NO 57
<211> LENGTH: 219
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Asp Ile Val Met Thr Gln Ser Pro Leu Ser Leu Pro Val Thr Pro Gly
1               5                   10                  15

Glu Pro Ala Ser Ile Ser Cys Arg Ser Arg Gln Ser Ile Val His Thr
            20                  25                  30

Asn Arg Tyr Thr Tyr Leu Ala Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Thr Val Ala Ala Pro Ser Val Phe Ile Phe Pro Pro Ser Asp Glu

```
            115                 120                 125
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
        210                 215
```

<210> SEQ ID NO 58
<211> LENGTH: 213
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 58

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Arg Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Arg Ser Asn Pro Tyr Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 59
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 59

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Asn Asn Arg
            20                  25                  30

Leu Ala Trp Tyr Gln Gln Lys Pro Gly Gln Ala Pro Arg Leu Leu Ile
        35                  40                  45

His Trp Ala Ser Thr Arg Ala Ile Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Ala Ser Trp Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 60
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 60

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Ser Arg
            20                  25                  30

Leu Ala Trp Tyr Gln Gln Lys Pro Gly Gln Ala Pro Arg Leu Leu Ile
        35                  40                  45

Tyr Trp Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Ala Tyr Trp Pro Phe
                85                  90                  95
```

```
Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 61
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 61

Asp Ile Val Met Thr Gln Ser Pro Ala Thr Leu Ser Val Thr Pro Gly
1               5                   10                  15

Asp Arg Val Ser Leu Ser Cys Arg Ala Ser Gln Thr Ile Ser Asp Tyr
            20                  25                  30

Leu His Trp Tyr Gln Gln Lys Ser His Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Gly Phe Pro Arg
                85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

-continued

```
<210> SEQ ID NO 62
<211> LENGTH: 226
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met His Trp Val Arg Gln Ala Pro Gly Gln Arg Leu Glu Trp Met
        35                  40                  45

Gly Asp Ile Tyr Pro Tyr Asn Gly Gly Thr Gly Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Trp His Ala Met Asp Ser Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys His His His His
    210                 215                 220

His His
225

<210> SEQ ID NO 63
<211> LENGTH: 233
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Thr Phe Thr Ser Tyr
            20                  25                  30

Trp Met Gln Trp Val Arg Gln Met Pro Gly Lys Gly Leu Glu Trp Met
        35                  40                  45

Gly Glu Ile Asn Pro Ser Asn Gly Arg Thr Asp Tyr Asn Glu Lys Phe
    50                  55                  60
```

```
Arg Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Gln Gly Gly Ser Gly Tyr Gly Asn Ser Tyr Gly Phe Phe Asp
             100                 105                 110

Val Trp Gly Gln Gly Thr Thr Val Thr Val Ser Ser Ala Ser Thr Lys
         115                 120                 125

Gly Pro Ser Val Phe Pro Leu Ala Pro Ser Ser Lys Ser Thr Ser Gly
     130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                 165                 170                 175

Phe Pro Ala Val Leu Gln Ser Ser Gly Leu Tyr Ser Leu Ser Ser Val
             180                 185                 190

Val Thr Val Pro Ser Ser Ser Leu Gly Thr Gln Thr Tyr Ile Cys Asn
         195                 200                 205

Val Asn His Lys Pro Ser Asn Thr Lys Val Asp Lys Lys Val Glu Pro
     210                 215                 220

Lys Ser Cys His His His His His His
225                 230
```

<210> SEQ ID NO 64
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 64

```
Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Asp Tyr
                 20                  25                  30

Trp Ile Gly Trp Val Arg Gln Met Pro Gly Lys Gly Leu Glu Trp Met
             35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Val Tyr Tyr Cys
                 85                  90                  95

Ala Arg Val Gly Arg Phe Ala Ser His Gln Leu Asp Tyr Trp Gly Gln
             100                 105                 110

Gly Thr Leu Val Thr Val Ser Ser Ala Ser Thr Lys Gly Pro Ser Val
         115                 120                 125

Phe Pro Leu Ala Pro Ser Ser Lys Ser Thr Ser Gly Gly Thr Ala Ala
     130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                 165                 170                 175
```

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys His
        210                 215                 220

His His His His His
225

<210> SEQ ID NO 65
<211> LENGTH: 229
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Asp Asp Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Val Tyr Tyr Cys
                85                  90                  95

Ala Arg Val Gly Arg Phe Ala Ser His Gln Leu Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys His
        210                 215                 220

His His His His His
225

<210> SEQ ID NO 66
<211> LENGTH: 227
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

```
<400> SEQUENCE: 66

Glu Val Lys Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Asp Lys Arg Leu Glu Trp Val
        35                  40                  45

Ala Thr Ile Thr Ser Gly Gly Thr Tyr Thr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Ile Asp Ser Leu Lys Ser Glu Asp Thr Ala Ile Tyr Phe Cys
                85                  90                  95

Ala Arg Ser Leu Ala Gly Asn Ala Met Asp Tyr Trp Gly Gln Gly Thr
            100                 105                 110

Ser Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys His His His
        210                 215                 220

His His His
225

<210> SEQ ID NO 67
<211> LENGTH: 7
<212> TYPE: PRT
<213> ORGANISM: Homo sapiens

<400> SEQUENCE: 67

Thr Val Pro Thr Asp Phe Ser
1               5

<210> SEQ ID NO 68
<211> LENGTH: 7
<212> TYPE: PRT
<213> ORGANISM: Macaca fascicularis

<400> SEQUENCE: 68

Thr Ala Pro Ala Asn Phe Ser
1               5
```

CD47 ANTIBODIES, METHODS, AND USES

This application is a national stage application of PCT/US2015/061014, filed Nov. 17, 2015, which claims priority benefit of U.S. Application No. 62/081,134 filed Nov. 18, 2014. The complete disclosures of the aforementioned related patent applications are hereby incorporated herein by reference for all purposes.

SEQUENCE LISTING

The instant application contains a Sequence Listing which has been submitted electronically in ASCII format and is hereby incorporated by reference in its entirety. Said ASCII copy, created on Nov. 5, 2015, is named PRD3361WOPCT_SL.txt and is 72,842 bytes in size.

FIELD

The subject matter herein relates generally to antibodies binding to CD47. The described anti-CD47 antibodies are useful as therapeutic agents for hematological disorders such as leukemias.

BACKGROUND

The protein cluster of differentiation 47 (CD47), also known as integrin associated protein (IAP), ovarian cancer antigen OA3, and Rh-related antigen, is a ubiquitously expressed cell surface pentaspan transmembrane Ig superfamily member. CD47 interacts with SIRP alpha (signal-regulatory protein alpha) on macrophages and thereby dampens phagocytosis. Cancer cells that co-opt this pathway evade phagocytosis and thereby promote cancer cell survival (Jaiswal, S., et al., Trends in Immunol 31: 212-219, 2010). This is a newly discovered mechanism of tumor immune avoidance; thus therapeutically targeting CD47 has widespread application in numerous cancers.

The expression of CD47 correlates with worse clinical outcomes in many distinct malignancies including Non-Hodgkin lymphoma (NHL), acute lymphocytic leukemia (ALL), acute myelogenous leukemia (AML), ovarian cancer, glioma, glioblastoma, etc. In addition, CD47 has been identified as a cancer stem cell marker in both leukemias and solid tumors (Jaiswal, et al., 2009 Cell, 138(2): 271-85; Chan, et al., 2009 Proc Natl Acad Sci USA, 106(33): 14016-21; Chan et al., 2010 Curr Opin Urol, 20(5): 393-7; Majeti R, et al., 2011 Oncogene, 30(9): 1009-19).

CD47-blocking antibodies have demonstrated anti-tumor activity for multiple in vivo tumor models. Blocking the interaction of CD47 with SIRP alpha is capable of promoting phagocytosis of CD47-expressing cells by macrophages (reviewed in Chao, et al., 2012 Curr Opin Immunol, 24(2): 225-32). Furthermore, these CD47-blocking antibodies have been shown to synergize with other therapeutic antibodies including Rituxan® and Herceptin® in tumor models.

However, CD47 antibodies have been reported to cause platelet aggregation and hemagglutination of red blood cells. Platelet aggregation and hemagglutination are examples of homotypic interactions, wherein two CD47-expressing cells are caused to aggregate or clump when treated with a bivalent CD47 binding entity. For example, the CD47 antibody, MABL, as a full IgG or F(ab')$_2$, has been reported to cause hemagglutination of erythrocytes and only when MABL was altered into an scFv or bivalent scFv was this effect mitigated. (See e.g., Uno S, Kinoshita Y, Azuma Y, et al., 2007 Oncol Rep, 17(5):1189-94). Similarly, the CD47 antibody, B6H12, has been reported to induce direct aggregation of the platelets of certain subjects that have certain polymormisphms of the Fc receptor, FcγRII (Dorahy D J, Thorne R F, Fecondo J V and Burns G F, 1997 Journal of Biol. Chem. 272:1323-1330). Thus, platelet aggregation and hemagglutination of RBCs represent a major limitation of therapeutically targeting CD47 with existing CD47 antibodies.

SUMMARY

Described herein are antibodies that specifically bind to CD47, inhibit CD47 from interacting with SIRP alpha, and do not have significant platelet aggregation activity.

In some embodiments, the antibody specifically binds to CD47 by interacting with CD47 (SEQ ID NO: 21 excluding the signal sequence) amino acid residues: Q1, L3, N27, E29, E97, L101, T102, R103, and E104. In some embodiments, the antibody interacts with CD47 (SEQ ID NO: 21 excluding the signal sequence) amino acid residues Y37, K39, R45, D46, T49, A53, L54, N55, K56, S57, T58, V59, P60, T61, S64, A66, and K67. In some embodiments, the antibody interacts with CD47 (SEQ ID NO: 21 excluding the signal sequence) amino acid residues E35, K39, Y37, D46, 49, D51, A53, L54, K56, T58, V59, T99, L101, and T102. In some embodiments, the antibody interact with CD47 (SEQ ID NO: 21 excluding the signal sequence) amino acid residues E29, Q31, N32, T34, E35, V36, Y37, K39, N41, D46, D51, A53, E97, T99, E100, L101, T102, R103, and E104.

Another aspect of some described embodiments feature an antibody that specifically binds to human or cyno CD47 comprising a variable heavy chain selected from SEQ ID NOs: 4-6. The antibody optionally comprises a variable light (VL) chain region selected from SEQ ID NOs: 7 and 8. In some cases, the antibody comprises a VH chain region selected from SEQ ID NOs: 4-6 and a VL chain region selected from SEQ ID NOs: 7 and 8. In other aspects, the antibody has a VH chain region comprising SEQ ID NO: 4 or SEQ ID NO: 5 paired with a VL chain region comprising SEQ ID NO: 7. In yet another aspect, the antibody has a VH chain region comprising SEQ ID NO: 6 paired with a VL chain region comprising SEQ ID NO: 8.

In some embodiments, the CD47 antibody comprises a VH complementarity determining region 1 (CDR1) sequence set forth in SEQ ID NO: 9 or SEQ ID NO: 10, a VH CDR2 sequence set forth in SEQ ID NO: 11 or SEQ ID NO: 12, a VH CDR3 sequence set forth in SEQ ID NO: 13 or SEQ ID NO: 14, a VL CDR1 sequence set forth in SEQ ID NO: 15 or SEQ ID NO: 16, a VL CDR2 sequence set forth in SEQ ID NO: 17 or SEQ ID NO: 18 and a VL CDR3 sequence set forth in SEQ ID NO: 19 or SEQ ID NO: 20. For example, the CD47 antibody comprises a VH CDR1 sequence set forth in SEQ ID NO: 9, a VH CDR2 sequence set forth in SEQ ID NO: 11, a VH CDR3 sequence set forth in SEQ ID NO: 13, a VL CDR1 sequence set forth in SEQ ID NO: 15, a VL CDR2 sequence set forth in SEQ ID NO: 17, and a VL CDR3 sequence set forth in SEQ ID NO: 19. In another example, the CD47 antibody comprises a VH CDR1 sequence set forth in SEQ ID NO: 10, a VH CDR2 sequence set forth in SEQ ID NO: 12, a VH CDR3 sequence set forth in SEQ ID NO: 14, a VL CDR1 set forth in SEQ ID NO: 16, a VL CDR2 sequence set forth in SEQ ID NO: 18, and a VL CDR3 sequence set forth in SEQ ID NO: 20.

In some embodiments, the antibodies bind to CD47 in a position wherein a VH chain has more extensive contacts with CD47 than a VL chain, wherein the VH chain of the antibody is positioned near the membrane of a CD47 expressing cell, and wherein a VL chain of the antibody occludes a SIRP alpha binding site on CD47.

In some embodiments, the antibodies do not have significant hemagglutination activity. In some embodiments, the platelet-aggregation activity of the antibodies is no more than 10% greater than the degree of platelet-aggregation observed in the absence of the antibody. In some embodiments, the antibody is chimeric, humanized, or fully human. In some embodiments, the antibody binds to human CD47 or cynomolgus (cyno) CD47. In some embodiments, the antibody promotes macrophage-mediated phagocytosis of a CD47-expressing cell. In some embodiments, the antibody or antigen binding fragment thereof comprises an IgG isotype selected from IgG1 isotype and IgG2 isotype.

Described herein are also pharmaceutical compositions that include an antibody described herein and a pharmaceutical acceptable carrier. The described antibodies can be included in kits. Polynucleotides encoding the described antibodies as well as vectors and cells suitable for expressing the described polynucleotides are also described.

Another embodiment comprises methods of alleviating a symptom of a cancer or other neoplastic condition by administering to a subject in need thereof one or more antibodies described herein, wherein the antibody does not have significant platelet aggregation activity after administration. The antibody is administered in an amount sufficient to alleviate the symptom of the cancer or other neoplastic condition in the subject. In some embodiments, the subject is a human. In some embodiments, the antibody is chimeric, humanized, or fully human. In some embodiments, the antibody inhibits CD47 from interacting with SIRP alpha. In some embodiments, the antibody comprises an IgG isotype selected from the group consisting of IgG1 isotype and IgG2 isotype. In some embodiments, chemotherapy is administered along with the described antibodies.

BRIEF DESCRIPTION OF THE DRAWINGS

(FIG. 1B). Shown are the SIRP alpha-blocking and CD47-binding activities of ten phage-derived mAbs in comparison to a positive control anti-CD47 mAb B6H12.2 and a human IgG2 Fc-silent (IgG2sigma) isotype control as determined by MSD (A) and FACS (B) assays respectively.

FIG. 6. Epitope and paratope regions of C47B161 (SEQ ID NOS 56, 57 and 62, respectively, in order of appearance), C47B167 (SEQ ID NOS 56, 58 and 63, respectively, in order of appearance), C47B222 (SEQ ID NOS 56, 59 and 64, respectively, in order of appearance), C47B227 (SEQ ID NOS 56, 60 and 65, respectively, in order of appearance), and B6H12.2 (SEQ ID NOS 56, 61 and 66, respectively, in order of appearance). The epitope residues from the CD47 ECD-C15G mutant (SEQ ID NO 49) and paratope residues from the VH and VL of each C47B161 (SEQ ID NOs: 5 and 7), C47B167 (SEQ ID NOs: 50 and 51), C47B222 (SEQ ID NOs: 6 and 8), C47B227 (SEQ ID NOs: 41 and 46) and B6H12.2 (SEQ ID NOs: 52 and 53) are shaded, the CDR regions are underlined and labeled (Kabat definition), and SIRP alpha binding residues are marked with a dot above the CD47 sequence.

FIGS. 7A-7D. Epitope location and interactions between CD47 and C47B161. C47B161 binds to the epitope bin 2 shown in black (FIG. 7A). 2D Interaction map between CD47 and C47B161. CDRs L1 and L2 are engaged in contacts with the antigen, while CDR L3 does not interact with CD47. Residues from all heavy chain CDRs contact CD47. Van der Waals interactions are shown as dashed lines, H bonds are solid lines with arrows indicating backbone H bonds and pointing to the backbone atoms. CD47, VL and VH residues are in gray boxes, white boxes and ovals, respectively. A distance cut-off of 4 Å was used to define the contacting residues (FIG. 7B). CD47 main interactions with the Fab light (FIG. 7C) and heavy (FIG. 7D) chains. The long CDR-L1 is represented by residues H31, N33, Y35 and Y37. H-bonds are shown as dashed lines. CD47 residues are underlined.

FIGS. 10A-10D. Epitope location and interactions between CD47 and C47B222. Epitope overall location: C47B161 binds to the epitope bin 1 region shown in black (FIG. 10A). 2D Interaction map between CD47 and C47B222: there is segregation between the CD47 residues recognize by the LC and HC. Van der Waals interactions are shown as dashed lines, H bonds are solid lines with arrows indicating backbone H bonds and pointing to the backbone atoms. CD47, VL and VH residues are in gray boxes, white boxes and ovals, respectively (FIG. 10B). A distance cut-off of 4 Å was used to define the contacting residues. CD47 main interactions with the Fab light (FIG. 10C) and heavy (FIG. 10D) chains. CDR-L3 does not bind CD47. H-bonds are shown as dashed lines. CD47 residues are underlined.

FIG. 11A-11D. Epitope location and interactions between CD47 and C47B227. Epitope overall location: C47B227 binds to the epitope bin 1 region shown in black (FIG. 11A). 2D Interaction map between CD47 and C47B227: there is epitope segregation with regions recognized either by the LC or HC. Van der Waals interactions are shown as dashed lines, H bonds are solid lines with arrows indicating backbone H bonds and pointing to the backbone atoms. CD47, VL and VH residues are in gray boxes, white boxes and ovals, respectively. A distance cut-off of 4 Å was used to define the contacting residues (FIG. 11B). Main interactions of CD47 with the Fab light (FIG. 11C) and heavy (FIG. 11D) chains. H-bonds are shown as dashed lines. CD47 residues are underlined.

FIGS. 15A and 15B. Induction of apoptosis in (FIG. 15A) Jurkat cells and (FIG. 15B) HL60 cells in response to 24 hour treatment with varying concentrations of anti-human CD47 IgG1/IgG2 Fc-silent C47B157, C47B161, C47B222, and B6H12.2.

(FIG. 17B) PBS, 200 µg/ml IgG1/IgG2 Fc-silent C47B157, and IgG1 B6H12.2; (FIG. 17C) PBS, 200 µg/ml IgG1/IgG2sigma C47B161, and IgG1 B6H12.2; and (FIG. 17D) PBS, 200 µg/ml IgG1/IgG2sigma C47B222, and IgG1 B6H12.2.

FIGS. 18A-18D. In vivo activity of IgG1/IgG2 Fc-silent C47B157, C47B161, C47B222, and B6H12.2 in the HL60/NSG mice model. NSG mice were implanted with 10 million HL60 cells intravenously and antibody treatment was initiated on day 6 following tumor cell implant. Each group consisted of five mice. Animals received a total of six doses, twice weekly (final dose day 23). Peripheral blood from the mice was collected weekly and analyzed via FACS to assess tumor cell outgrowth and treatment effects starting on day 14 (final collection on day 42).

DETAILED DESCRIPTION

Figure 1A:
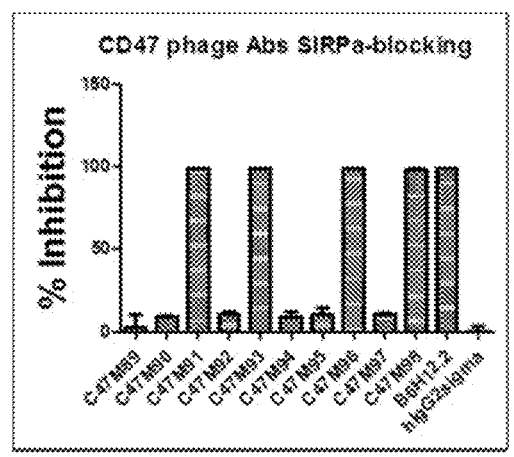
FIGS. 1A and 1B. Inhibition of SIRP alpha-Fc binding to Jurkat cells by phage-derived human IgG2 Fc-silent mAbs (FIG. 1A). Binding to Jurkat cells by phage-derived human IgG2 Fc-silent mAbs.

Some characteristics of antibodies described herein include:
specific binding to human CD47 and cyno CD47,
blocking CD47 interaction with SIRP alpha,
do not have significant human platelet aggregation activity,
do not have significant hemagglutination activity,
are capable of promoting phagocytosis of tumor cells by macrophages,
display potent anti-tumor activity in a mouse model of human cancers.
Accordingly, the antibodies described herein stand to be of great importance in the treatment of a multitude of cancers.

Many existing CD47 antibodies block SIRP alpha. However, prior to the subject matter described herein, existing full IgG CD47 antibodies that blocked SIRP alpha caused the side effect of platelet aggregation and/or hemagglutination, which, as described above, is an undesirable characteristic. Other existing antibodies, such as 2D3, do not cause hemagglutination, however, these antibodies also do not block SIRP alpha. Thus, there were previously no known CD47 antibodies in a full IgG format that blocked SIRP alpha without causing platelet and red blood cell clumping.

In some embodiments the IgG CD47 antibodies described herein do not exhibit significant platelet aggregation and hemagglutination, thereby increasing the efficacy of therapeutically targeting CD47, and maintain the ability to block the interaction of CD47 with SIRP alpha, which promotes phagocytosis of CD47-expressing cells. Specifically, the full IgG CD47 antibodies of the present disclosure (e.g., C47B157, C47B161 and C47B222) do not have significant cell agglutination activity. For example, the CD47 antibodies described herein do not have significant platelet aggregation and hemagglutination activity. Thus, taken together, the antibodies described herein (e.g., C47B157, C47B161 and C47B222 and derivatives thereof) are unique among existing CD47 antibodies in their ability to block SIRP alpha, without significant platelet aggregation and hemagglutination activity.

General

Those skilled in the art will appreciate that the disclosure herein is susceptible to variations and modifications other than those specifically described. It is to be understood that the present disclosure encompasses all such variations and modifications. The present disclosure also includes all of the steps, features, compositions and compounds referred to or indicated in this specification, individually or collectively, and any and all combinations or any two or more of said steps or features.

The present disclosure is not to be limited in scope by the specific embodiments described herein, which are intended for the purpose of exemplification only. Functionally-equivalent products, compositions, and methods are clearly within the scope of the present disclosure.

The compositions of matter and methods described herein are produced or performed without undue experimentation using, unless otherwise indicated, conventional techniques of molecular biology, microbiology, virology, recombinant DNA technology, peptide synthesis in solution, solid phase peptide synthesis, pharmaceutical chemistry, medicinal chemistry and immunology. Standard techniques are used for pharmaceutical preparation, formulation, and delivery, and treatment of patients.

Definitions

Unless otherwise defined, scientific and technical terms used in connection with the present disclosure shall have the meanings that are commonly understood by those of ordinary skill in the art.

As utilized in accordance with the present disclosure, the following terms, unless otherwise indicated, shall be understood to have the following meanings:

The term "and/or", e.g., "X and/or Y" shall be understood to mean either "X and Y" or "X or Y" and shall be taken to provide explicit support for both meanings or for either meaning.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

As used herein, the terms "CD47", "integrin-associated protein (IAP)", "ovarian cancer antigen OA3", and "Rh-related antigen" are synonymous and may be used interchangeably.

The terms "red blood cell(s)" and "erythrocyte(s)" are synonymous and used interchangeably herein.

As used herein, the term "platelet aggregation" refers to the adhesion of activated platelets to one another that results in the formation of aggregates or clumps of activated platelets. Platelet aggregation is measured, as described in the Examples, using an aggregometer, which measures the increase in the transmittance of light as platelet aggregation occurs. "Significant platelet aggregation activity" occurs if there is an increase in light transmittance of at least 25% by 6 minutes after the addition of an antibody described herein relative to light transmittance prior to antibody addition.

The term "agglutination" refers to cellular clumping, while the term "hemagglutination" refers to clumping of a specific subset of cells, i.e., red blood cells. Thus, hemagglutination is a type of agglutination.

In the hemagglutination assay described herein, patterns in a given well are formed by erythrocytes which can be either "buttons," "halos," or intermediate between the two. The term "significant hemagglutination activity" refers to the presence of any halo pattern in a well upon the addition of an antibody described herein.

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "directed against" is meant that the antibody reacts with one or more antigenic determinants of the desired antigen and does not react with, or binds at much lower affinity ($K_d > 10^6$), to other polypeptides. Antibodies include, but are not limited to monoclonal, chimeric, dAb (domain antibody), single chain, Fab, Fab- and F(ab')$_2$ fragments, F$_v$, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as IgG1, IgG$_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen.

In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk, J. Mol. Biol. 196:901-917 (1987), Chothia et al. Nature 342:878-883 (1989).

As used herein, the term "epitope" includes any protein determinant capable of specific binding to an immunoglobulin or fragment thereof, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 µM.

As used herein, the terms "specifically binds," refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity.

Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($k_{on}$) and the "off rate constant" ($k_{off}$) can be determined by calculation of the concentrations and the actual rates of association and dissociation. (See Nature 361:186-87 (1993)). The ratio of $k_{off}/k_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to CD47, when the equilibrium binding constant ($K_d$) is ≤1 µM, as measured by assays such as radioligand binding assays, surface plasmon resonance (SPR), flow cytometry binding assay, or similar assays known to those skilled in the art.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "polypeptide" is used herein as a generic term to refer to native protein, fragments, or analogs of a polypeptide sequence. Hence, native protein fragments, and analogs are species of the polypeptide genus.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides described herein are either sense or antisense oligonucleotides.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland? Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences". As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

"Conservative" amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present disclosure, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known (Bowie et al. Science 253:164 (1991)). Thus, the foregoing examples demonstrate that those of skill in the art can recognize sequence motifs and structural conformations that may be used to define structural and functional domains in accordance with the present disclosure.

Preferred amino acid substitutions are those which: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991).

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

Other chemistry terms herein are used according to conventional usage in the art, as exemplified by The McGraw-Hill Dictionary of Chemical Terms (Parker, S., Ed., McGraw-Hill, San Francisco (1985)).

CD47 Antibodies

Monoclonal antibodies described herein have the ability to bind CD47, to inhibit the binding of SIRP alpha to CD47, decrease CD47-SIRP alpha-mediated signaling, promote phagocytosis, and to inhibit tumor growth and/or migration. Inhibition is determined, for example, using the cellular assay described herein in the Examples.

Exemplary antibodies described herein include an antibody having a variable heavy (VH) chain selected from SEQ ID NOs: 4-6, and having a variable light (VL) chain selected from SEQ ID NOs: 7 and 8. Specifically, exemplary antibodies include those provided in Table 1.

TABLE 1

| Antibody | Variable heavy (VH) chain | Variable light (VL) chain |
| --- | --- | --- |
| C47B157 | SEQ ID NO: 4 | SEQ ID NO: 7 |
| C47B161 | SEQ ID NO: 5 | SEQ ID NO: 7 |
| C47B222 | SEQ ID NO: 6 | SEQ ID NO: 8 |

The complementarity determining regions (CDRs) of the VH chain of the CD47 antibodies are highlighted below. In some embodiments, the amino acid sequence of VH CDR1 is DYNMH (SEQ ID NO: 9) or DYWIG (SEQ ID NO: 10). In some embodiments, the amino acid sequence of VH CDR2 is DIYPYNGGTGYNQKFKG (SEQ ID NO: 11) or IIYPGDSDTRYSPSFQG (SEQ ID NO: 12). In some embodiments, the amino acid sequence of VH CDR3 is GGWHAMDS (SEQ ID NO: 13) or VGRFASHQLDY (SEQ ID NO: 14).

In some embodiments, the amino acid sequence of VL CDR1 is RSRQSIVHTNRYTYLA (SEQ ID NO: 15) or RASQSVNNRLA (SEQ ID NO: 16). In some embodiments, the amino acid sequence of VL CDR2 is KVSNRFS (SEQ ID NO: 17) or WASTRAI (SEQ ID NO: 18). In some embodiments, the amino acid sequence of VL CDR3 is FQGSHVPYT (SEQ ID NO: 19) or QQGASWPFT (SEQ ID NO: 20).

Also included in this disclosure are antibodies that bind to the same epitope as the CD47 antibodies described herein. For example, antibodies described in this application specifically bind to an epitope that includes one or more amino acid residues of an exemplary human CD47 that is provided below (GenBank Accession No. Q08722.1 (GI:1171879), incorporated herein by reference). The signal sequence (amino acids 1-18) is underlined.

SEQ ID NO: 21
MWPLVAALLLGSACCGSAQLLFNKTKSVEFTFCNDTVVIPCFVTNME

AQNTTEVYVKWKFKGRDIYTFDGALNKSTVPTDFSSAKIEVSQLLKG

DASLKMDKSDAVSHTGNYTCEVTELTREGETIIELKYRVVSWFSPNE

NILIVIFPIFAILLFWGQFGIKTLKYRSGGMDEKTIALLVAGLVITV

IVIVGAILFVPGEYSLKNATGLGLIVTSTGILILLHYYVFSTAIGLT

SFVIAILVIQVIAYILAVVGLSLCIAACIPMHGPLLISGLSILALAQ

LLGLVYMKFVASNQKTIQPPRKAVEEPLNAFKESKGMMNDE

In some embodiments the antibodies interact with Q1, L3, N27, E29, E97, L101, T102, R103, and E104 of SEQ ID NO: 21. In some embodiments the antibodies interact with Y37, K39, R45, D46, T49, A53, L54, N55, K56, S57, T58, V59, P60, T61, S64, A66, and K67 of SEQ ID NO:21. In some embodiments the antibodies interact with E35, K39, Y37, D46, 49, D51, A53, L54, K56, T58, V59, T99, L101, and T102 of SEQ ID NO: 21. In some embodiments the antibodies interact with E29, Q31, N32, T34, E35, V36, Y37, K39, N41, D46, D51, A53, E97, T99, E100, L101, T102, R103, and E104 of SEQ ID NO: 21.

Those skilled in the art will recognize that it is possible to determine, without undue experimentation, if an antibody has the same specificity as one of the antibodies described herein (e.g., C47B157, C47B161 and C47B222, or an antibody having a variable heavy chain selected from SEQ ID NOs: 4-6, and a variable light chain selected from SEQ ID NOs: 7 and 8) by ascertaining whether the former prevents the latter from binding to CD47. If the antibody being tested competes with the antibody of this disclosure, as shown by a decrease in binding by the antibody described herein, then the two antibodies likely bind to the same, or a nearby, epitope.

An alternative method for determining whether an antibody has the specificity of an antibody described herein is to pre-incubate the antibody described herein with soluble CD47 protein (with which it is normally reactive), and then add the antibody being tested to determine if the antibody being tested is inhibited in its ability to bind CD47. If binding of the antibody being tested is inhibited then, in all likelihood, it has the same, or functionally equivalent, epitope specificity as the antibody of this disclosure.

Antibodies of the Present Disclosure

The antibodies described herein, can be assessed for the ability to modulate, block, inhibit, reduce, antagonize, neutralize or otherwise interfere with CD47- and/or CD47/SIRP alpha-mediated signaling. For example, such assessments may include measuring CD47- and/or CD47/SIRP alpha-mediated signaling in the presence of one or more of the antibodies described herein. These assays can include competitive binding assays or can measure a biologic readout, for example the ability to promote phagocytosis of a CD47 expressing cell by a macrophage, as is described in Example 7.

Various procedures known within the art may be used for the production of monoclonal antibodies directed against CD47, or against derivatives, fragments, analogs homologs or orthologs thereof (See, for example, Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies" or "fully human antibodies" herein. Human monoclonal antibodies are prepared, for example, using the procedures described in the Examples provided below. Human monoclonal antibodies can be also prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The CD47 antibodies of this disclosure are monoclonal antibodies. Monoclonal antibodies that modulate, block, inhibit, reduce, antagonize, neutralize or otherwise interfere with CD47- and/or CD47/SIRP alpha-mediated cell signaling are generated, e.g., by immunizing an animal with membrane bound and/or soluble CD47, such as, for example, human CD47 or an immunogenic fragment, derivative or variant thereof. Alternatively, the animal is immunized with cells transfected with a vector containing a nucleic acid molecule encoding CD47 such that CD47 is expressed and associated with the surface of the transfected cells. Alternatively, the antibodies are obtained by screening a library that contains antibody or antigen binding domain sequences for binding to CD47. This library is prepared, e.g., in bacteriophage as protein or peptide fusions to a bacteriophage coat protein that is expressed on the surface of assembled phage particles and the encoding DNA sequences contained within the phage particles (i.e., "phage displayed library"). Hybridomas resulting from myeloma/B cell fusions are then screened for reactivity to CD47.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof, or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies described herein can be readily isolated and sequenced using conventional procedures (e.g., by using oligonucleotide probes that are capable of binding specifically to genes encoding the heavy and light chains of murine antibodies). The hybridoma cells described herein serve as a preferred source of such DNA. Once isolated, the DNA can be placed into expression vectors, which are then transfected into host cells such as Chinese hamster ovary (CHO) cells, Human Embryonic Kidney (HEK) 293 cells, simian COS cells, PER.C6®, NS0 cells, SP2/0, YB2/0, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody described herein, or can be substituted for the variable domains of one antigen-combining site of an antibody described herein to create a chimeric bivalent antibody.

Human Antibodies and Humanization of Antibodies

The antibodies described herein include fully human antibodies or humanized antibodies. These antibodies are suitable for administration to humans without engendering an immune response by the human against the administered immunoglobulin.

A CD47 antibody is generated, for example, by phage-display methods using antibodies containing only human sequences. Such approaches are well-known in the art, e.g., in WO92/01047 and U.S. Pat. No. 6,521,404, which are hereby incorporated by reference. In this approach, a combinatorial library of phage carrying random pairs of light and heavy chains are screened using natural or recombinant source of CD47 or fragments thereof. In another approach, a CD47 antibody can be produced by a process wherein at least one step of the process includes immunizing a transgenic, non-human animal with human CD47 protein. In this approach, some of the endogenous heavy and/or kappa light chain loci of this xenogenic non-human animal have been disabled and are incapable of the rearrangement required to generate genes encoding immunoglobulins in response to an antigen. In addition, at least one human heavy chain locus and at least one human light chain locus have been stably transfected into the animal. Thus, in response to an administered antigen, the human loci rearrange to provide genes encoding human variable regions immunospecific for the antigen. Upon immunization, therefore, the xenomouse produces B-cells that secrete fully human immunoglobulins.

A variety of techniques are well-known in the art for producing xenogenic non-human animals. For example, see U.S. Pat. Nos. 6,075,181 and 6,150,584, which is hereby incorporated by reference in its entirety. This general strategy was demonstrated in connection with generation of the first XenoMouse™ strains as published in 1994. See Green et al. Nature Genetics 7:13-21 (1994), which is hereby incorporated by reference in its entirety. See also, U.S. Pat. Nos. 6,162,963; 6,150,584; 6,114,598; 6,075,181; and 5,939,598 and Japanese Patent Nos. 3 068 180 B2, 3 068 506 B2, and 3 068 507 B2 and European Patent No., EP 0 463 151 B1 and International Patent Applications No. WO 94/02602, WO 96/34096, WO 98/24893, WO 00/76310 and related family members.

The production of antibodies with reduced immunogenicity is also accomplished via humanization, chimerization and display techniques using appropriate libraries. It will be appreciated that murine antibodies or antibodies from other species can be humanized or primatized using techniques well known in the art. See e.g., Winter and Harris Immunol Today 14:43 46 (1993) and Wright et al. Crit. Reviews in Immunol. 12125-168 (1992). The antibody of interest may be engineered by recombinant DNA techniques to substitute the CH1, CH2, CH3, hinge domains, and/or the framework domain with the corresponding human sequence (See WO 92102190 and U.S. Pat. Nos. 5,530,101; 5,585,089; 5,693, 761; 5,693,792; 5,714,350; and 5,777,085). Also, the use of Ig cDNA for construction of chimeric immunoglobulin genes is known in the art (Liu et al. P.N.A.S. 84:3439 (1987) and J. Immunol. 139:3521 (1987)). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) Sequences of Proteins of immunological Interest, N.I.H. publication no. 91-3242. Human C region genes are readily available from known clones. The choice of isotype will be guided by the desired effecter functions, such as complement fixation, or activity in antibody-dependent cellular cytotoxicity. Preferred isotypes are IgG1 and IgG2. Either of the human light chain constant regions, kappa or lambda, may be used. The chimeric, humanized antibody is then expressed by conventional methods.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, human antibodies or antibodies from other species can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright et al. Crit, Reviews in Immunol. 12125-168 (1992), Hanes and Plückthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743. If display technologies are utilized to produce antibodies that are not human, such antibodies can be humanized as described above.

Using these techniques, antibodies can be generated to CD47 expressing cells, soluble forms of CD47, epitopes or peptides thereof, and expression libraries thereto (See e.g., U.S. Pat. No. 5,703,057), which can thereafter be assessed as described previously for desired characteristics.

The CD47 antibodies described herein can be expressed by a vector containing a DNA segment encoding the single chain antibody described above. These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet. 3:219 (1993); Yang, et al., J. Virol. 69:2004 (1995) and Adeno-associated Virus Vectors (see Kaplitt, M. G., et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of CD47 in a sample. The antibody can also be used to try to bind to and disrupt CD47- and/or the CD47/SIRP alpha interaction and CD47/SIRP alpha-mediated signaling.

Techniques can be adapted for the production of single-chain antibodies specific to an antigenic protein described herein (see e.g., U.S. Pat. No. 4,946,778). In addition, methods can be adapted for the construction of Fab expression libraries (see e.g., Huse, et al., 1989 Science 246: 1275-1281) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an F(ab')$_2$ fragment produced by pepsin digestion of an antibody molecule; (ii) an Fab fragment generated by reducing the disulfide bridges of an F(ab')$_2$ fragment; (iii) an Fab fragment generated by the treatment of the antibody molecule with papain and a reducing agent and (iv) F$_v$ fragments. Thus variations of the described embodiments are contemplated which include F$_v$, Fab, Fab' and F(ab')$_2$ CD47 fragments, single chain CD47 antibodies, single domain antibodies (e.g., nanobodies or VHHs), bispecific CD47 antibodies, and heteroconjugate CD47 antibodies.

Fc Modifications

It can be desirable to modify the antibody described herein with respect to effector function, so as to enhance, e.g., the effectiveness of the antibody in treating diseases and disorders associated with aberrant CD47 signaling. For example, because CD47 is ubiquitously expressed, mutation(s) can be introduced into the Fc region of the antibody in order to silence effector function, thereby decreasing the likelihood of normal cell-killing.

In some embodiments, the antibody described herein is an IgG isotype. In some embodiments, the constant region of the antibody is of human IgG1 isotype, having the amino acid sequence of SEQ ID NO: 1.

In some embodiments, the constant region of the antibody is of human IgG2 isotype, having the amino acid sequence of SEQ ID NO: 2.

In some embodiments, the human IgG2 constant region is modified at amino acids Val234, Gly237, Pro238, His268, Val309, Ala329, and Pro330 (Kabat Numbering) to alter Fc receptor interactions (see WO11/066501 Al). For example, Val234Ala, Gly237Ala (G237A), Pro238Ser (P238S), His268Ala (H268A), Val309Leu (V309L), Ala329Ser (A329S), and Pro330Ser (P330S)). (EU index of Kabat et al 1991 Sequences of Proteins of Immunological Interest). In some embodiments, the constant region of the antibody of the modified human IgG2 has the amino acid sequence of SEQ ID NO: 3.

Use of Antibodies Against CD47

It will be appreciated that therapeutics in accordance with the described embodiments will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate for use in treatments and therapies in accordance with the present disclosure, provided that the active ingredient in the formulation is not inactivated by the formulation and the formulation is physiologically compatible and tolerable with the route of administration.

In one embodiment, the described antibodies may be used as therapeutic agents. Such agents will generally be employed to treat, alleviate, and/or prevent a disease or pathology associated with aberrant CD47 expression, activity and/or signaling in a subject. A therapeutic regimen is carried out by identifying a subject, e.g., a human patient suffering from (or at risk of developing) a disease or disorder associated with aberrant CD47 expression, activity and/or signaling, e.g., a cancer or other neoplastic disorder, using standard methods. An antibody preparation, preferably one having high specificity and high affinity for its target antigen, is administered to the subject and will generally have an effect due to its binding with the target. Administration of the antibody may abrogate or inhibit or interfere with the expression, activity and/or signaling function of the target (e.g., CD47). Administration of the antibody may abrogate or inhibit or interfere with the binding of the target (e.g., CD47) with an endogenous ligand (e.g., SIRP alpha) to which it naturally binds. For example, the antibody binds to the target and modulates, blocks, inhibits, reduces, antagonizes, neutralizes, or otherwise interferes with CD47 expression, activity and/or signaling. In some embodiments an antibody having heavy and light chain CDRs with the amino acid sequences described in Table 2 may be administered to a subject in order to treat a disease or disorder associated with aberrant CD47 expression. In one embodiment the disease or disorder associated with aberrant CD47 expression may be cancer.

TABLE 2

Selected Antibody Sequences

| CDR | C47B157 and C47B161 | C47B222 |
|---|---|---|
| HC CDR 1 | DYNMH (SEQ ID NO: 9) | DYWIG (SEQ ID NO: 10) |
| HC CDR 2 | DIYPYNGGTGYNQKFKG (SEQ ID NO: 11) | IIYPGDSDTRYSPSFQG (SEQ ID NO: 12) |
| HC CDR 3 | GGWHAMDS (SEQ ID NO: 13) | VGRFASHQLDY (SEQ ID NO: 14) |
| LC CDR 1 | RSRQSIVHTNRYTYLA (SEQ ID NO: 15) | RASQSVNNRLA (SEQ ID NO: 16) |
| LC CDR 2 | KVSNRFS (SEQ ID NO: 17) | WASTRAI (SEQ ID NO: 18) |
| LC CDR 3 | FQGSHVPYT (SEQ ID NO: 19) | QQGASWPFT (SEQ ID NO: 20) |

Diseases or disorders related to aberrant CD47 expression, activity and/or signaling include, by way of non-limiting example, hematological cancer and/or solid tumors. Hematological cancers include, e.g., leukemia, lymphoma and myeloma. Certain forms of leukemia include, by way of non-limiting example, acute lymphocytic leukemia (ALL); acute myeloid leukemia (AML); chronic lymphocytic leukemia (CLL); chronic myelogenous leukemia (CML); Myeloproliferative disorder/neoplasm (MPDS); and myelodysplasia syndrome. Certain forms of lymphoma include, by way of non-limiting example, Hodgkin's lymphoma, both indolent and aggressive non-Hodgkin's lymphoma, Burkitt's lymphoma, and follicular lymphoma (small cell and large cell). Certain forms of myeloma include, by way of non-limiting example, multiple myeloma (MM), giant cell myeloma, heavy-chain myeloma, and light chain or Bence-Jones myeloma. Solid tumors include, e.g., breast tumors, ovarian tumors, lung tumors, pancreatic tumors, prostate tumors, melanoma tumors, colorectal tumors, lung tumors, head and neck tumors, bladder tumors, esophageal tumors, liver tumors, and kidney tumors.

Symptoms associated with cancers and other neoplastic disorders include, for example, inflammation, fever, general malaise, fever, pain, often localized to the inflamed area, loss of appetite, weight loss, edema, headache, fatigue, rash, anemia, muscle weakness, muscle fatigue and abdominal symptoms such as, for example, abdominal pain, diarrhea or constipation.

A therapeutically effective amount of an antibody described herein relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody cleared from the body. Common ranges for therapeutically effective dosing of an antibody or antibody fragment described herein may be, by way of nonlimiting example, from about 0.1 mg/kg body weight to about 100 mg/kg body weight. In one embodiment the therapeutically effective does of an antibody described herein is from about 0.1 mg/kg body weight to about 0.3 mg/kg body weight. In one embodiment the therapeutically effective does of an antibody described herein is from about 0.4 mg/kg body weight to about 0.6 mg/kg body weight. In one embodiment the therapeutically effective does of an antibody described herein is from about 0.7 mg/kg body weight to about 0.9 mg/kg body weight. In one embodiment the therapeutically effective does of an antibody described herein is from about 1.0 mg/kg body weight to about 2.0 mg/kg body weight. In one embodiment the therapeutically effective does of an antibody described herein is from about 2.0 mg/kg body weight to about 3.0 mg/kg body weight. In one embodiment the therapeutically effective does of an antibody described herein is from about 3.0 mg/kg body weight to about 4.0 mg/kg body weight. In one embodiment the therapeutically effective does of an antibody described herein is from about 4.0 mg/kg body weight to about 5.0 mg/kg body weight. In one embodiment the therapeutically effective does of an antibody described herein is from about 5.0 mg/kg body weight to about 6.0 mg/kg body weight. In one embodiment the therapeutically effective does of an antibody described herein is from about 6.0 mg/kg body weight to about 7.0 mg/kg body weight. In one embodiment the therapeutically effective does of an antibody described herein is from about 7.0 mg/kg body weight to about 8.0 mg/kg body weight. In one embodiment the therapeutically effective does of an antibody described herein is from about 8.0 mg/kg body weight to about 9.0 mg/kg body weight. In one embodiment the therapeutically effective does of an antibody described herein is from about 9.0 mg/kg body weight to about 10.0 mg/kg body weight. In one embodiment the therapeutically effective does of an antibody described herein is from about 10.0 mg/kg body weight to about 15.0 mg/kg body weight. In one embodiment the therapeutically effective does of an antibody described herein is from about 15.0 mg/kg body weight to about 20.0 mg/kg body weight. Common dosing frequencies may range, for example, from once a day to twice daily to once every other day to once a week.

Efficaciousness of treatment is determined in association with any known method for diagnosing or treating the particular inflammatory-related disorder. Alleviation of one or more symptoms of the inflammatory-related disorder indicates that the antibody confers a clinical benefit.

In another embodiment, antibodies directed against CD47 may be used in methods known within the art relating to the localization and/or quantitation of CD47 (e.g., for use in measuring levels of CD47 and/or both CD47 and SIRP alpha within appropriate physiological samples, for use in diagnostic methods, for use in imaging the protein, and the like). In a given embodiment, antibodies specific to CD47, or derivative, fragment, analog or homolog thereof, that contain the antibody derived antigen binding domain, are utilized as pharmacologically active compounds (referred to hereinafter as "therapeutics").

In another embodiment, an antibody specific for CD47 can be used to isolate a CD47 polypeptide, by standard techniques, such as immunoaffinity, chromatography or immunoprecipitation. Antibodies directed against the CD47 protein (or a fragment thereof) can be used to detect the protein in a biological sample. In some embodiments CD47 may be detected in a biological sample as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

In yet another embodiment, an antibody according to this disclosure can be used as an agent for detecting the presence of CD47 and/or both CD47 and SIRP alpha protein (or a protein fragment thereof) in a sample. In some embodiments, the antibody contains a detectable label. Antibodies are polyclonal, or more preferably, monoclonal. An intact antibody, or a fragment thereof (e.g., Fab, scFv, or F(ab')$_2$) is used. The term "labeled", with regard to an antibody, is intended to encompass direct labeling of the antibody by coupling (i.e., physically linking) a detectable substance to the antibody, as well as indirect labeling of the antibody by reactivity with another reagent that is directly labeled. Examples of indirect labeling include detection of a primary antibody using a fluorescently-labeled secondary antibody and end-labeling of an antibody with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of a described embodiment can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Therapeutic Administration and Formulations of CD47 Antibodies

The antibodies described herein and derivatives, fragments, analogs and homologs thereof, can be incorporated into pharmaceutical compositions suitable for administration. Principles and considerations involved in preparing such compositions, as well as guidance in the choice of components are well known in the art, for example, see Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the antibody and a pharmaceutically acceptable carrier. Where antibody fragments are used, the smallest inhibitory fragment that specifically binds to the binding domain of the target protein may be preferred. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the antibody, use thereof in the compositions is contemplated.

The formulations to be used for in vivo administration must be sterile. This is readily accomplished by filtration through sterile filtration membranes.

A pharmaceutical composition of a described embodiment is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the antibody in the required amount in an appropriate solvent with one or a combination of ingredients enumerated above, as required, followed by filtered sterilization. Generally, dispersions are prepared by incorporating the antibody into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, one or more of the described antibodies may be formulated into an ointment, salve, gel, or cream as generally known in the art.

The compounds can also be prepared in the form of suppositories (e.g., with conventional suppository bases such as cocoa butter and other glycerides) or retention enemas for rectal delivery.

In one embodiment, the described antibodies may be prepared with carriers that will protect against rapid elimination from the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be encapsulated in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate parenteral compositions in dosage unit form for ease of administration and uniformity of dosage. Dosage unit form as used herein refers to physically discrete units suited as unitary dosages for the subject to be treated; each unit containing a predetermined quantity of one or more of the described antibodies calculated to produce the desired therapeutic effect in association with the required pharmaceutical carrier. The specification for the dosage unit forms of the described embodiments are dictated by and directly dependent on the unique characteristics of the antibody and the particular therapeutic effect to be achieved, and the limitations inherent in the art of compounding such an antibody for the treatment of individuals.

The described pharmaceutical compositions can be included in a container, pack, or dispenser together with instructions for administration.

The formulation described herein can also contain more than one of the described antibodies as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, one or more of the described antibodies may be administered as a combination therapy, i.e., combined with other agents, e.g., therapeutic agents, that are useful for treating pathological conditions or disorders, such as various forms of cancer, autoimmune disorders and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

For example, the combination therapy can include one or more antibodies described herein coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Such combination therapies may advantageously utilize lower dosages of the administered therapeutic agents, thus avoiding possible toxicities or complications associated with the various monotherapies.

Preferred therapeutic agents used in combination with an antibody described herein are those agents that interfere at different stages in an inflammatory response. In one embodiment, one or more antibodies described herein may be coformulated with, and/or coadministered with, one or more additional agents such as other cytokine or growth factor antagonists (e.g., soluble receptors, peptide inhibitors, small molecules, ligand fusions); or antibodies or antigen binding fragments that bind to other targets (e.g., antibodies that bind to other cytokines or growth factors, their receptors, or other cell surface molecules); and anti-inflammatory cytokines or agonists thereof.

In other embodiments, the antibodies described herein are used as vaccine adjuvants against autoimmune disorders, inflammatory diseases, etc. The combination of adjuvants for treatment of these types of disorders are suitable for use in combination with a wide variety of antigens from targeted self-antigens, i.e., autoantigens, involved in autoimmunity, e.g., myelin basic protein; inflammatory self-antigens, e.g., amyloid peptide protein, or transplant antigens, e.g., alloantigens. The antigen may comprise peptides or polypeptides derived from proteins, as well as fragments of any of the following: saccharides, proteins, polynucleotides or oligonucleotides, autoantigens, amyloid peptide protein, transplant antigens, allergens, or other macromolecular components. In some instances, more than one antigen is included in the antigenic composition.

Additional Screening Methods

The present disclosure provides methods (also referred to herein as "screening assays") for identifying modulators, i.e., candidate or test compounds or agents (e.g., peptides, peptidomimetics, small molecules or other drugs) that modulate or otherwise interfere with the binding of CD47 to SIRP alpha, or candidate or test compounds or agents that modulate or otherwise interfere with the signaling function of CD47 and/or CD47-SIRP alpha. Also provided are methods of identifying compounds useful to treat disorders associated with aberrant CD47 and/or CD47-SIRP alpha expression, activity and/or signaling. The screening methods can include those known or used in the art or those described herein. For example, CD47 can be immobilized on a microtiter plate and incubated with a candidate or test compound, e.g., a CD47 antibody, in the presence of SIRP alpha. Subsequently, bound SIRP alpha can be detected using a secondary antibody, and absorbance can be detected on a plate reader.

Methods of identifying compounds capable of promoting phagocytosis of tumor cells by macrophages are also provided. These methods can include those known or used in the art or those described herein. For example, macrophages are incubated with labeled tumor cells in the presence of a candidate compound, e.g., a CD47 antibody. After a period of time, the macrophages can be observed for internalization of the tumor label to identify phagocytosis. Additional details regarding these methods, e.g., SIRP alpha blocking assays and phagocytosis assays, are provided in the Examples. This disclosure also includes compounds identified in the screening assays described herein.

In one embodiment, assays are provided for screening candidate or test compounds which modulate the signaling function of CD47. The test compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of described in this disclosure. Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37: 1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233,409.). In one embodiment, a candidate compound is introduced to an antibody-antigen complex and determining whether the candidate compound disrupts the antibody-antigen complex, wherein a disruption of this complex indicates that the candidate compound modulates the signaling function of CD47 and/or the interaction between CD47 and SIRP alpha. In another embodiment, a soluble CD47 and/or both CD47 and SIRP alpha protein described herein is provided and exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat disorders associated with aberrant CD47 and/or CD47-SIRP alpha signaling.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a neutralizing antibody, which modulates or otherwise interferes with CD47 activity and/or signaling.

The screening methods disclosed herein may be performed as a cell-based assay or as a cell-free assay. The cell-free assays of the described embodiments are amenable to use of either the soluble form or the membrane-bound form of CD47 and fragments thereof. In the case of cell-free assays comprising the membrane-bound form of CD47, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound can be accomplished in any vessel suitable for containing the reactants. Examples of such vessels include microtiter plates, test tubes, and microcentrifuge tubes. In one embodiment, a fusion protein that adds a domain that allows one or both of the proteins to be bound to a matrix can be provided. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of a described embodiment. For example, either the antibody (e.g., C47B157, C47B161 and C47B222, or an antibody having a variable heavy chain selected from SEQ ID NOs: 4-6 and a variable light chain selected from SEQ ID NOs: 7 and 8) or the antigen (e.g. CD47 protein) can be immobilized utilizing conjugation of biotin and streptavidin. Biotinylated antibody or antigen molecules can be prepared from biotin-NHS(N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The present disclosure further pertains to novel agents identified by any of the aforementioned screening assays and uses thereof for treatments as described herein.

Diagnostic and Prophylactic Formulations

The antibodies described herein may be used in diagnostic and prophylactic formulations. In one embodiment, one or more of the described antibodies may be administered to a subject that are at risk of developing one or more of the aforementioned diseases, such as for example, without limitation, cancer or other neoplastic condition. A subject's or organ's predisposition to one or more of the aforementioned cancers or other neoplastic conditions can be determined using genotypic, serological or biochemical markers.

Antibodies described herein are also useful in the detection of CD47 and/or SIRP alpha in patient samples and accordingly are useful as diagnostics. For example, the CD47 antibodies described herein are used in in vitro assays, e.g., ELISA, to detect CD47 and/or SIRP alpha levels in a patient sample.

In one embodiment, an antibody described herein is immobilized on a solid support (e.g., the well(s) of a microtiter plate). The immobilized antibody serves as a capture antibody for any CD47 and/or SIRP alpha that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of CD47 and/or SIRPa in the test sample is determined by comparison with a standard curve developed from the standard samples.

It will be appreciated that based on the results obtained using the described antibodies in an in vitro diagnostic assay, it is possible to determine the stage of disease (e.g., a clinical indication associated with ischemia, an autoimmune or inflammatory disorder) in a subject based on expression levels of CD47 and/or SIRP alpha. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

EXAMPLES

Example 1

Generation of CD47 Antibodies Using Hydridoma Technology

Balb/c mice were immunized with recombinant human CD47-Fc Chimera (R&D systems) to initiate anti-CD47 antibody development utilizing Freunds adjuvant (Sigma), InterFAD (mouse Interferon alpha, PBL InterferonSource), or 2-dose adjuvant (Creative Diagnostics) using standard immunization protocols. To develop hybridomas expressing CD47 antibodies, spleens from immunized mice were harvested and B-cells were isolated for fusion with SP20-Bc12 myeloma cells. Hybridoma clones from 4 fusions (C47Y1, C47Y2, C47Y3, and C47Y4) were assayed by ELISA for antibody binding to CD47 but not to the Fc-Tag. The hybridoma supernatants showing specific binding to CD47 were further screened for binding to CD47-expressing Jurkat cells (TIB-152, ATCC) and for blocking SIRP alpha binding to Jurkat cells by meso scale discovery (MSD)-based assays.

Briefly, Jurkat cells were washed and resuspended in phosphate buffered saline and then captured onto MSD 96-well high bind plates at 30,000 cells per well by incubating at 37° C. for 1.5 hours. The plates were blocked with 15% fetal bovine serum (FBS) (or heat-inactivated FBS) for 30 min at room temperature with gentle agitation. For cell-binding activity, hybridoma supernatants were incubated with cells captured on MSD high binding plates at 4° C. for 1 hour, and the bound antibodies were detected with a MSD Sulfo-Tag labeled goat anti-mouse antibody.

For SIRP alpha-blocking activity, recombinant SIRP alpha-Fc (R&D systems) at 2 µg/ml was incubated with Jurkat cells in the presence of hybridoma supernatants for 1-1.5 hours, and the bound SIRP alpha was detected with a MSD Sulfo-Tag labeled mouse anti-SIRP alpha antibody (R&D systems). The plates were read on a Sector 6000 imager and electrochemiluminescence (ECL) signals were recorded. The percent inhibition was normalized to no antibody and no SIRP alpha controls included in the assay. Hybridoma hits showing neutralization of SIRP alpha binding were selected for molecular cloning of antibody V-regions. Briefly, the cDNAs from hybridoma hits of interest were isolated by reverse transcriptase reaction with Invitrogen's SuperScript III cells Direct cDNA System, and then V regions were amplified through PCR with pre-mixed forwards primers and reverse primers prior to infusion cloning onto murine IgG1/K constant regions. After recombinant expression in HEK293 cells (Life Technologies), the transient transfection supernatants containing mIgG1 mAbs were re-screened in the Jurkat cell-binding and SIRP alpha-blocking assays. A total of 20 sequence unique mIgG1 mAbs with confirmed SIRP alpha-blocking activity (>40% inhibition, Table 3) were selected for conversion into chimeric human IgG2 Fc-silent/human kappa mAbs.

TABLE 3

List of hybridoma-derived mIgG1 mAbs that demonstrated >40% inhibition of SIRP alpha blocking.

| Hybridoma | mIgG1 Ab | % Inhibition |
|---|---|---|
| C47Y3_22G02 | C47M27 | 98.9 |
| C47Y2_4E11 | C47M87 | 98.8 |
| C47Y2_33D06 | C47M38 | 98.6 |
| C47Y3_5F06 | C47M26 | 98.4 |
| C47Y2_11E03 | C47M69 | 96.9 |
| C47Y2_9A04 | C47M71 | 96.6 |
| C47Y2_30E07 | C47M41 | 96.5 |
| C47Y3_16C06 | C47M32 | 96.4 |
| C47Y2_28E03 | C47M47 | 93.4 |
| C47Y3_11H10 | C47M36 | 91.0 |
| C47Y4_3A12 | C47M22 | 85.9 |
| C47Y3_13A03 | C47M34 | 85.4 |
| C47Y1_01D03 | C47M6 | 79.0 |
| C47Y4_2E06 | C47M23 | 77.5 |
| C47Y2_5D02 | C47M80 | 70.0 |
| C47Y2_19F06 | C47M57 | 52.3 |
| C47Y4_2C02 | C47M24 | 49.4 |
| C47Y2_13A02 | C47M66 | 43.1 |
| C47Y2_29H05 | C47M45 | 41.0 |
| C47Y3_11B09 | C47M37 | 40.4 |

Example 2

Generation of CD47 Antibodies Using Phage Display Technology

CD47 Reagents and Methods: A recombinant human CD47 extracellular domain (ECD) protein (SEQ ID NO. 22) with the addition of a C-terminal 6× HIS tag (SEQ ID NO: 55) was generated in-house for phage panning. The cDNA clone for human CD47 was obtained from Origene, and the ECD region was amplified by PCR and subcloned into a mammalian expression vector. After transient transfection of HEK 293F cells, the secreted His-tagged human CD47-ECD proteins were purified via Immobilized-metal affinity chromatography (IMAC) using HisTrap columns (GE Healthcare). Peak fractions were pooled and concentrated before being chromatographed over a 26/60 Superdex 200 column (GE Healthcare) for a final polishing step to obtain a monomeric form and a dimeric form of the CD47-ECD proteins. The CD47-ECD proteins were biotinylated using a 10-fold molar excess of sulfo-NHS-LC-Biotin (Pierce) for phage panning experiments.

Phage Display: In-house de novo phage libraries have been described in detail (Shi et al (2010) J. Mol. Biol. 397:385-396; Int. Pat. Publ. No. WO09/085462). These libraries were built on three human VH germline genes (IGHV1-69, 3-23, 5-51) and four human VL germline genes (A27, B3, L6, 012) designed to have high diversity in CDR-H3. Three de novo phage libraries (DNP00004-169HC/LC mix, DNP00005-323HC/LC mix and DNP00006-551HC/LC mix) displaying Fab variants on phage coat protein pIX were panned against biotinylated human CD47-ECD in the dimer form according to standard protocols. The panning conditions used include: panning with biotinylated human CD47 ECD dimer at room temperature for 1 hour, with Round 1 antigen concentration at 100 nM and using Streptavidin beads in capturing phage; Round 2 antigen concentration at 100 nM and using Neutravidin beads in capturing phage; and Round 3 antigen concentration at 10 nM and using with Streptavidin beads in capturing phage. Fab proteins were produced and captured onto ELISA plates by a polyclonal anti-Fd (CH1) antibody. Biotinylated CD47 ECD was added at the desired nM concentration, and the bound biotinylated CD47 was detected by HRP-conjugated streptavidin and chemiluminescence read in a plate reader. Fab clones were also sequenced for their VH and VL identity. The VHs from selected Fabs were amplified with framework-specific primers from E. coli clone expressing the Fab of interest using PCR and subcloned into mammalian expression vector containing signal peptide for mammalian expression and the human IgG2 effector function silent (IgG2 Fc silent) heavy chain constant region. Similarly, the VLs were amplified and were subcloned into a mammalian expression vector containing the kappa light chain constant region. The subcloning was done by Infusion cloning (Clontech) with the primers used summarized in Table 4. Infusion cloning is also known as ligation-independent cloning (LIC), where DNA fragments were connected to each other based on sequence homology without the use of restriction endonucleases or DNA ligase.

TABLE 4

Primers used to convert Fab hits to mAb expressing constructs

| Primer Name | SEQ ID NO: | Primer Sequences |
|---|---|---|
| HuG1_DNVH_F169 | 23 | CAAAGTATACAGGCCCAGGTG CAGCTGGTGCAGAG |
| HuG1_DNVH_F323 | 24 | CAAAGTATACAGGCCGAAGTG CAGCTGCTGGAAAG |
| HuG1_DNVH_F551 | 25 | CAAAGTATACAGGCCGAAGTG CAGCTGGTGCAGAGC |
| HuG1_DNVH_R | 26 | GCCCTTGGTGGAGGCGCTGCT CACGGTCACCAG |
| HuK_DNVL_FA27L6muSP | 27 | CAAAGTATCCAAGCAGAAATT GTGCTGACCCAGAG |
| HuK_DNVL_FO12muSP | 28 | CAAAGTATCCAAGCAGATATT CAGATGACCCAGAGC |
| HuK_DNVL_R | 29 | TGCAGCCACCGTACGTTTAAT TTCCACTTTGGTGCC |

Figure 1B:
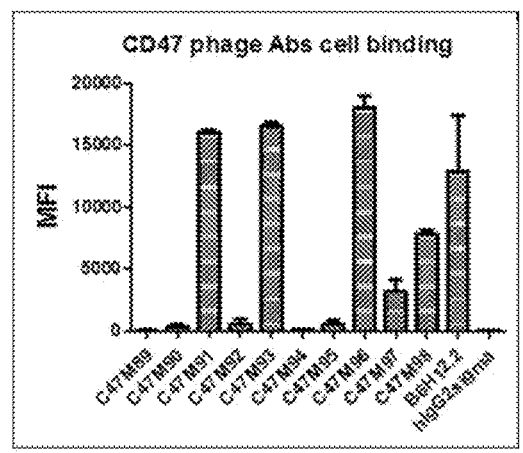
Figure 2A:
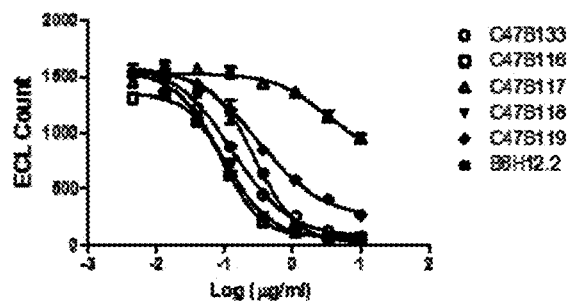
FIGS. 2A-2D. Dose dependent inhibition of SIRP alpha-Fc binding to CD47 expressing Jurkat cells by a subset of 23 human IgG2 Fc-silent mAbs. Shown are the dose response curves of 17 hybridoma mAbs and 3 phage mAbs in comparison to the positive control anti-CD47 mAb B6H12.2 in the cell-based SIRP alpha-blocking MSD assay.
Figure 2B:
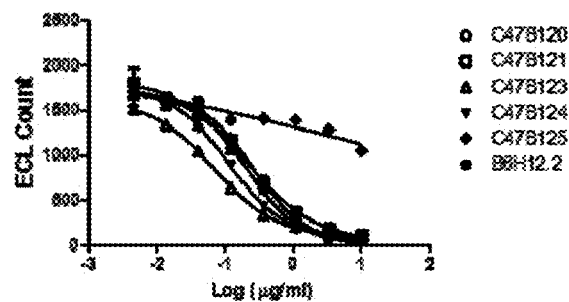
Figure 2C:
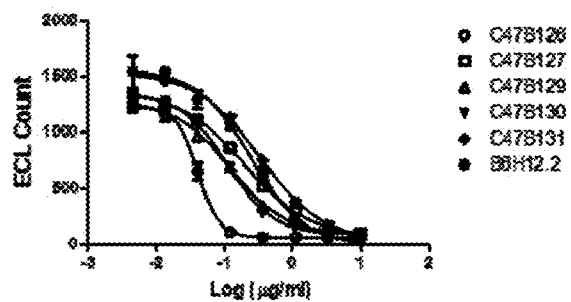
Figure 2D:
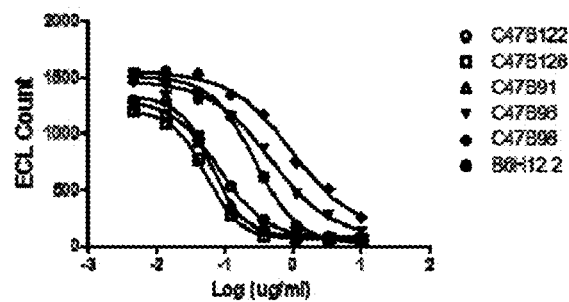

The newly generated VH and VL mammalian expression DNA constructs were paired together to generate 10 mAbs for further characterization. They were transiently transfected in HEK293F cells, and the resulting supernatants containing mAbs were characterized for their ability to bind to CD47 on Jurkat cells by FACS and to block SIRP alpha binding to Jurkat cells as previously described. A commercially available anti-CD47 B6H12.2 was subcloned into the human IgG2sigma constant region and used as a positive control in the assays. FIG. 1 shows the activity of ten phage-derived mAbs, among which four displayed strong SIRP alpha-blocking activity. Three of them C47B91 (=C47M91), C47B96 (=C47M96) and C47B98 (=C47M98) were confirmed as CD47 specific cell-binders and therefore selected for further characterization.

Example 3

Bioactivity of CD47 Antibodies

The ability of the 23 total CD47 antibodies generated (20 from hybridoma methods and 3 from phage display methods) to bind CD47 and to block certain bioactivities of CD47 was analyzed using various in vitro assays as described below.

CD47 binding assay: Human CD47 and Cyno CD47 ECD proteins were generated in-house as His-tagged proteins as described in Example 2. Kinetic binding affinities to human CD47 and Cyno CD47 ECD proteins were determined by a Protein Interaction Array System (ProteOn). Briefly, mAbs were captured on the sensor chip via anti-IgG-Fc to reach surface density of 200-350 RU. The CD47 ECD monomeric proteins were serially titrated from 300 nM down to 3.7 nM and injected for 5 min. The dissociation was monitored for 30 min. Data were fitted to 1:1 binding model. The $K_D$ values of the 23 mAbs as well as the ratios between affinities to human and Cyno CD47 proteins are listed in Table 3. Most of the mAbs showed cyno CD47 cross-reactivity (within 5 fold affinity of human CD47) with the exception of C47B121, C47B120, and C47B131.

Binning assay: This assay permits assessment of the panel of antibodies individually as both capture and detection reagents with the rest of the antibodies in the panel. Antibodies forming effective capture/detection reagents with each other theoretically recognize spatially-separated epitopes on a monomeric protein, thus allowing both antibodies to bind to the target protein at the same time. Groups of clones exhibiting similar patterns of activity across the entire panel are hypothesized to bind to similar epitopes. Selecting clones from different groups should therefore provide antibodies recognizing different epitopes. The CD47 antibodies were directly immobilized on GLC sensors (Bio-Rad). Competing samples were pre-incubated with 200 nM of CD47-ECD for 4 hrs before injection over the chip surface for 4 min to allow association. Dissociation was then monitored for 4 min. The results suggest there might be 4 distinct epitope groups, with group 1 and 2 overlapping and competing with each other, while group 3 only overlaps with group 1 but not with group 2.

SIRP alpha Blocking Activity: The potency of SIRP alpha blocking by the 23 CD47 antibodies was measured by serially titrating the antibodies and incubating with Jurkat cells captured on MSD high-binding plates for 1 hour, then removed before incubation of recombinant SIRP alpha-Fc to Jurkat cells for another 1.5 hrs. The bound SIRP alpha was detected with a MSD Sulfo-Tag labeled mouse anti-SIRP alpha antibody. The ECL signal was plotted as a function of antibody concentrations, and $EC_{50}$ values were obtained from fitting the dose-response curves using non-linear regression model in GraphPad Prism. All antibodies demonstrated dose-dependent inhibition of SIRP alpha binding to CD47-expressing cells. FIG. 2 shows the dose-response curves of a subset of the anti-CD47 mAbs in the assay.

Hemagglutination Activity: The 23 mAbs were also evaluated for activity in hemagglutination assays. Briefly, blood was collected from healthy donor volunteers into Vacutainer blood collection tubes (BD Biosciences), buffered with sodium citrate.

Figure 3A:
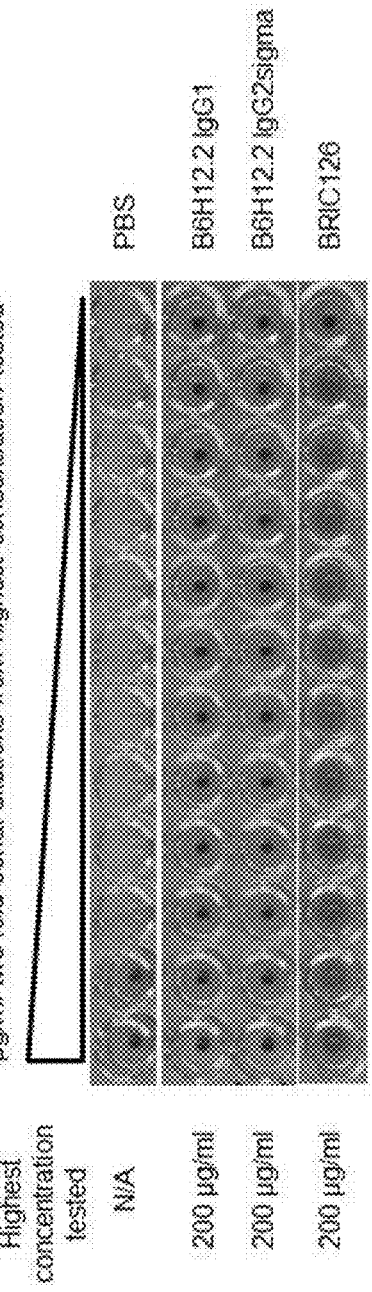
FIGS. 3A and 3B. Hemagglutination of human red blood cells in response to varying doses of anti-human CD47 monoclonal antibodies IgG1/IgG2 Fc-silent B6H12.2 and commercially available BRIC126 (FIG. 3A). Representative results of hemagglutination assays with 23 anti-CD47 mAbs. Shown are hemagglutination results in response to C47B91, C47B98, C47B116, C47B123, and C47B131 (FIG. 3B).
Figure 3B:
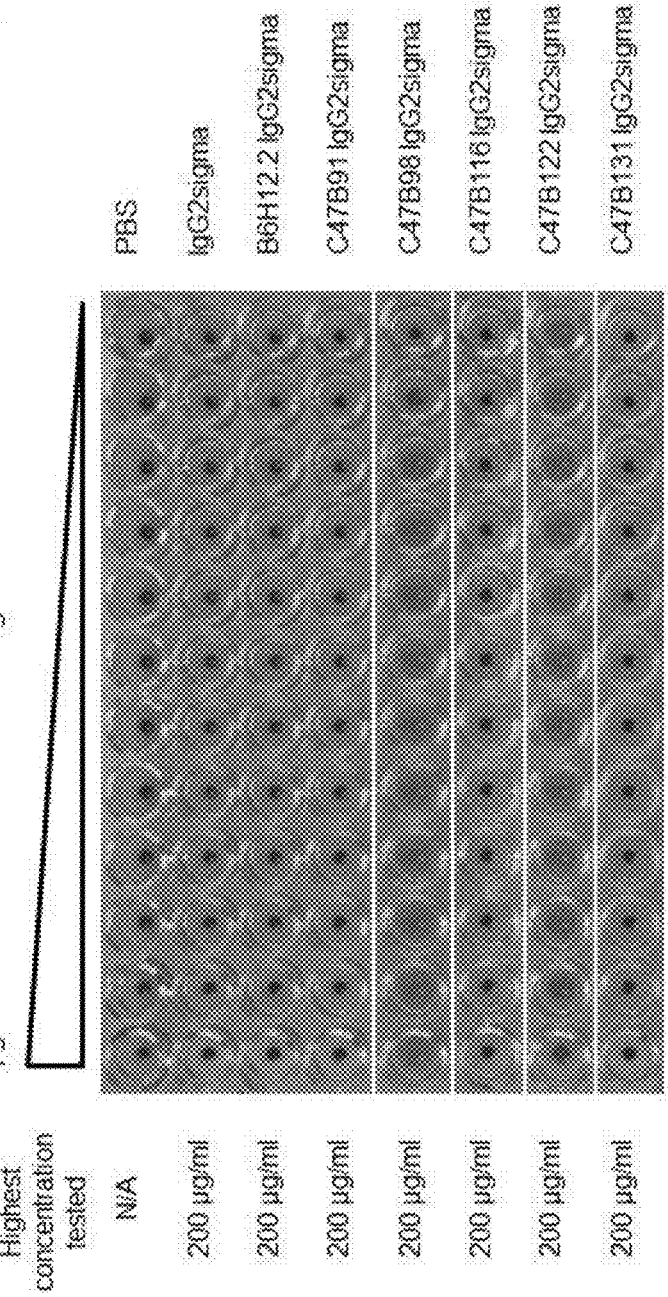
Figure 4:
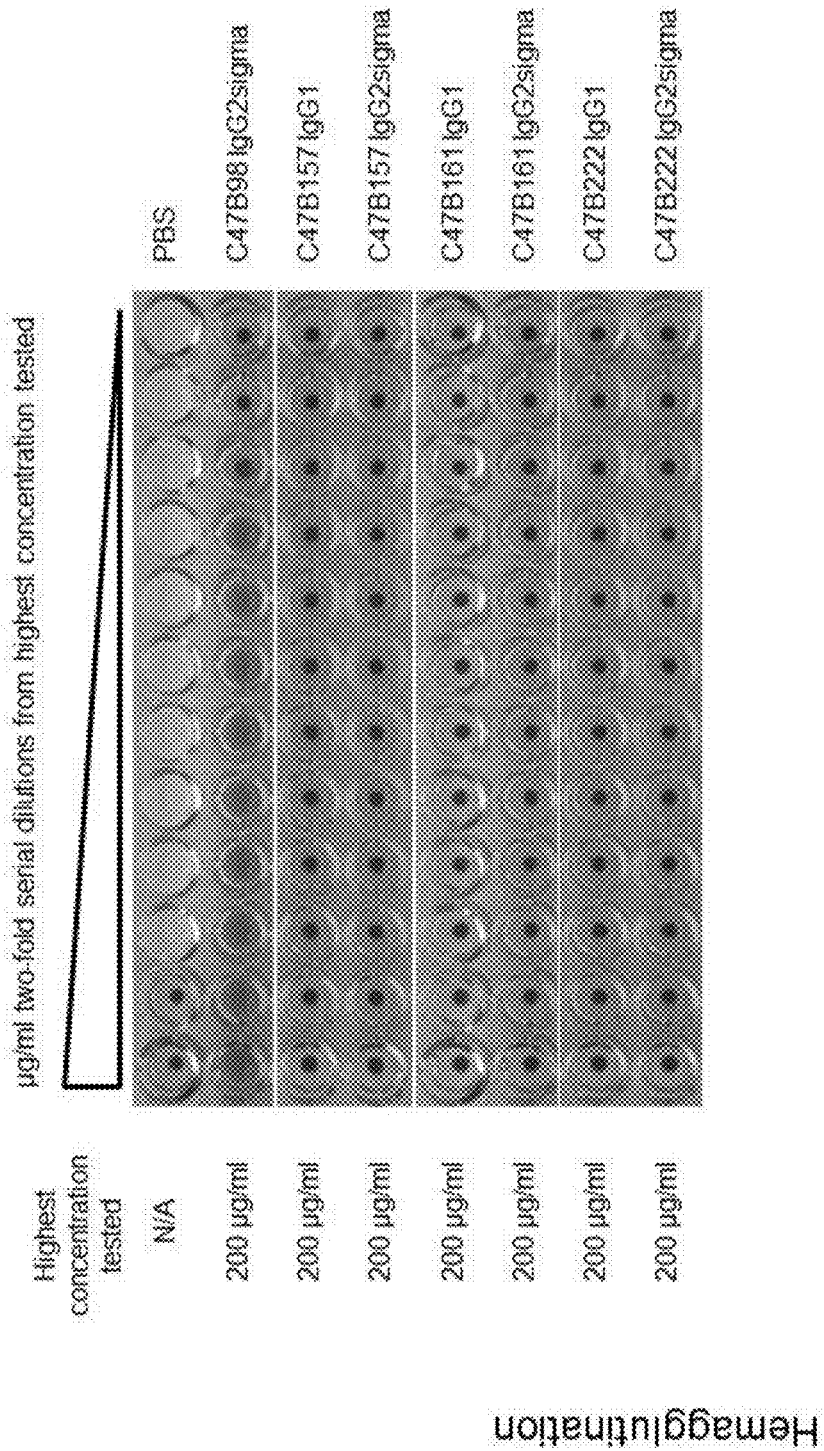
FIG. 4. Hemagglutination of human red blood cells in response to varying doses of anti-human IgG1/IgG2 Fc-silent C47B157, C47B161, and C47B222. IgG2 Fc silent C47B98 known to induce hemagglutination (see FIG. 3B) was included as positive control.
Figure 5A:
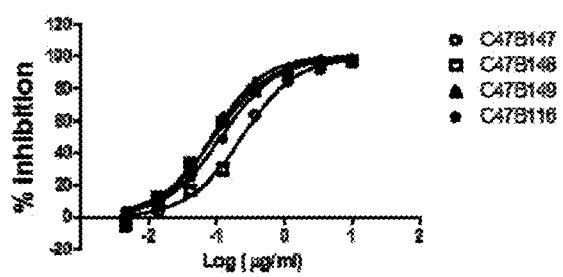
FIGS. 5A-5D. Dose dependent inhibition of SIRP alpha-Fc binding to CD47 expressing Jurkat cells by HFA variants of C47B116. Shown are the dose response curves of 12 human frame work adapted variants in comparison to the parent hybridoma mAb C47B116 in the cell-based SIRP alpha-blocking MSD assay.
Figure 5B:
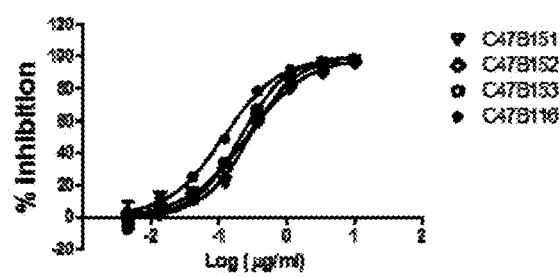
Figure 5C:
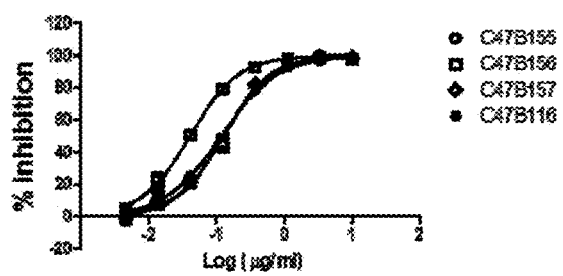
Figure 5D:
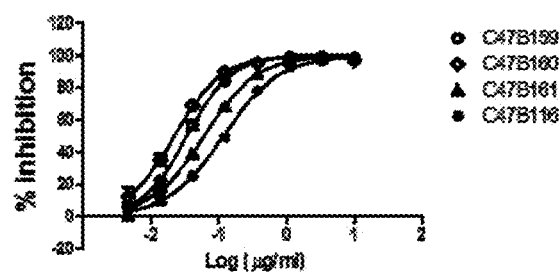

Blood was washed with PBS three times and a 2% erythrocyte suspension was prepared in PBS. 50 µl of the serially diluted mAbs (2-fold) were incubated with 50 µl of the 2% erythrocyte suspension for 2 hours at room temperature in clear 96-well round bottom plates and subsequently were scored for hemagglutination when RBCs did not appear as tight pellets in the well. The starting concentration from which 2-fold serial dilutions were prepared was 200 µg/ml for most mAbs tested. In instances where antibody stock concentrations were less concentrated (C47B118 and C47B119) the starting concentration prepared for antibodies was 85 µg/ml. Most of the tested mAbs did induce hemagglutination (representative results shown in FIG. 3 and FIG. 4), however no association of hemagglutination with any other properties of these mAbs was found.

The characteristics of the 23 mAbs in these assays were summarized in Table 5. Among them, C47B116 and C47B91 were selected for further optimization, as they did not induce hemagglutination, showed potent SIRP alpha-blocking activity as well as good affinity to both human CD47 and Cyno CD47.

TABLE 5

Characteristics of the 23 anti-CD47 mAbs including affinity to human and cyno CD47, ability to block SIRP alpha, epitope bins and hemagglutination (Hg) activities. Lowest concentrations at which hemagglutination was visibly observed are indicated where appropriate.

| mAb ID | SIRPa-blocking $EC_{50}$ (µg/ml) | Human CD47 $K_D$ (M) | Cyno CD47 $K_D$ (M) | $K_D$ Ratio Cyno/Human | Epitope Bin | Hg |
|---|---|---|---|---|---|---|
| B6H12.2 | 0.21 | 5.39E−10 | 5.72E−10 | 1.1 | 1 | N |
| C47B115 | NA | 1.41E−09 | 7.12E−09 | 5.0 | 2 | Y ≥0.195 µg/ml |
| C47B116 | 0.10 | 1.41E−09 | 9.67E−10 | 0.7 | 2 | N |
| C47B117 | 2.96 | 8.72E−08 | 1.52E−07 | 1.7 | 4 | N |
| C47B118 | 0.09 | 3.96E−09 | 2.64E−09 | 0.7 | 2 | Y ≥0.332 µg/ml |
| C47B119 | 0.32 | 2.46E−09 | 2.35E−09 | 1.0 | 2 | N |
| C47B120 | 0.26 | 5.56E−09 | 7.85E−08 | 14.1 | 1 | N |
| C47B121 | 0.20 | 7.16E−09 | NB | | 3 | N |
| C47B122 | 0.08 | 1.64E−09 | 2.91E−09 | 1.8 | 2 | Y ≥0.098 µg/ml |
| C47B123 | 0.07 | 2.07E−09 | 1.71E−09 | 0.8 | 2 | Y ≥0.098 µg/ml |

TABLE 5-continued

Characteristics of the 23 anti-CD47 mAbs including affinity to human and cyno CD47, ability to block SIRP alpha, epitope bins and hemagglutination (Hg) activities. Lowest concentrations at which hemagglutination was visibly observed are indicated where appropriate.

| mAb ID | SIRPa-blocking EC$_{50}$ (μg/ml) | Human CD47 K$_D$ (M) | Cyno CD47 K$_D$ (M) | K$_D$ Ratio Cyno/Human | Epitope Bin | Hg |
|---|---|---|---|---|---|---|
| C47B124 | 0.11 | 3.65E−09 | 2.90E−09 | 0.8 | 2 | Y ≥0.781 μg/ml |
| C47B125 | ~ | 4.05E−08 | 3.32E−08 | 0.8 | 2 | N |
| C47B126 | 0.04 | 3.44E−10 | 2.60E−10 | 0.8 | 1 | Y ≥0.098 μg/ml |
| C47B127 | 0.19 | 3.28E−09 | 4.14E−09 | 1.3 | 2 | Y ≥0.781 μg/ml |
| C47B128 | 0.05 | 2.23E−09 | 2.22E−09 | 1.0 | 1 | Y ≥0.098 μg/ml |
| C47B129 | 0.12 | 2.78E−09 | 4.94E−09 | 1.8 | 2 | Y ≥0.195 μg/ml |
| C47B130 | 0.11 | 4.84E−09 | 4.28E−09 | 0.9 | 1 | Y ≥0.064 μg/ml |
| C47B131 | 0.33 | 1.45E−09 | 1.62E−07 | 111.7 | 3 | N |
| C47B132 | NA | 2.65E−09 | 9.62E−09 | 3.6 | 2 | Y ≥0.083 μg/ml |
| C47B133 | 0.13 | 1.06E−09 | 3.80E−09 | 3.6 | 2 | Y ≥0.098 μg/ml |
| C47B134 | NA | 2.54E−09 | 2.71E−09 | 1.1 | 2 | Y ≥0.391 μg/ml |
| C47B91 | 0.06 | 1.56E−08 | 2.45E−08 | 1.6 | 1 | N |
| C47B96 | 0.46 | 6.08E−08 | 3.58E−08 | 0.6 | 1 | Y ≥3.125 μg/ml |
| C47B98 | 0.95 | 3.24E−09 | 3.24E−09 | 1.0 | 2 | Y ≥0.098 μg/ml |

Note:
the K$_D$ numbers for B6H12.2 represent averages of 5 readings in the same experiment.
NA: not tested in the same experiment.

Example 4

Human Framework Adaptation of C47B116

Initial analysis of the amino acid sequence of the C47B116 VH domain (SEQ ID NO: 30) suggests that the closest mouse germline genes are IGHV1S29*02 for HV and IGHJ4*01 for HJ. Initial analysis of the amino acid sequence of the C47B116 VL domain (SEQ ID NO: 54) suggests that the closest mouse germline genes are IGKV117*01 and IGKJ2*01. For human framework adaption (HFA) of C47B116 to reduce immunogenicity in humans, four human VH (IGHV1-3, IGHV1-46, IGHV1-69, and IGHV5-51) and 3 human VL (IGKV2-28, IGKV3-1, and IGKV4-1) variants chains have been designed to replace the mouse framework in C47B116 VL and VH sequences with human frameworks while keeping the CDRs intact, based on sequence homology analysis and consideration for future affinity maturation using in-house de novo libraries. Constructs for each VH (SEQ ID NO: 4, 5, 31, and 32) and VL (SEQ ID NO: 7, 33, and 34) chains were generated by gene assembly and cloned into vectors for human IgG2sigma expression. Combinations of VH and VL variants were co-transfected into HEK 293Expi expression system and the resulting 12 HFA variants were purified from culture supernatants by Protein-A chromatography. The purified C47B116 HFA variants were again characterized for SIRP alpha—blocking, binding affinities to human and Cyno CD47, and hemagglutination as previously described. For the hemagglutination assays, the starting concentration from which 2-fold serial dilutions were prepared was 200 μg/ml for most mAbs tested. In instances were antibody stock concentrations were less concentrated, starting concentrations for the serial dilutions were prepared at 125 μg/ml (C47B160), 170 μg/ml487B156), and 195 μg/ml (C47B159). All variants demonstrated potent SIRP alpha-blocking activity (FIG. 5). C47B148, C47B151, C47B152, C47B156, and C47B160 induced hemagglutination, suggesting frameworks may contribute to this activity. The selected C47B116 HFA variants investigated for kinetic binding studies showed similar affinity to human CD47 and cyno CD47. Some HFA variants (C47B155, C47B157, C47B159 and C47B161) retained good binding affinity (within 5-fold of the parent mAb C47B116) to CD47, whereas others (C47B147, C47B149, C47B151 and C47B153) showed more significant loss in affinity (more than 6 fold decrease compared to C47B116). The data are summarized in Table 6. C47B157 and C47B161 were chosen for further characterization because they maintained potent SIRP alpha—blocking activity, good binding affinity to both human and cyno CD47, but exhibited no hemagglutination activity or biophysical property concerns.

TABLE 6

Characterization of 12 C47B116 HFA variants for SIRP alpha-blocking, affinity to human CD47 and cyno CD47, and hemagglutination activities. The lowest concentrations at which hemagglutination was visibly observed are indicated where appropriate.

| C47BB116 HFA Ab | SIRPa-blocking $EC_{50}$ (μg/ml) | Human CD47 $K_D$ (M) | Cyno CD47 $K_D$ (M) | KD Ratio Cyno/Human | Hemagglutination |
|---|---|---|---|---|---|
| C47B147 | 0.24 | 9.55E−09 | 1.35E−08 | 1.4 | Y ≥0.781 μg/ml |
| C47B148 | 0.09 | NA | NA | | Y ≥0.098 μg/ml |
| C47B149 | 0.09 | 7.95E−09 | 1.16E−08 | 1.5 | N |
| C47B151 | 0.29 | 6.89E−09 | 9.34E−09 | 1.4 | Y ≥0.781 μg/ml |
| C47B152 | 0.26 | NA | NA | | Y ≥0.195 μg/ml |
| C47B153 | 0.21 | 6.39E−09 | 7.92E−09 | 1.2 | N |
| C47B155 | 0.13 | 4.27E−09 | 4.65E−09 | 1.1 | N |
| C47B156 | 0.04 | NA | NA | | Y ≥0.083 μg/ml |
| C47B157 | 0.13 | 3.53E−09 | 3.71E−09 | 1.1 | N |
| C47B159 | 0.03 | 2.60E−09 | 2.29E−09 | 0.9 | N |
| C47B160 | 0.02 | NA | NA | | Y ≥0.061 μg/ml |
| C47B161 | 0.06 | 2.87E−09 | 2.96E−09 | 1.0 | N |
| C47B116 | 0.12 | 1.02E−09 | 9.50E−10 | 0.9 | N |

Example 5

Affinity Maturation of C47B91

The heavy chain of C47B91 (SEQ ID NO: 35) is coming from 5-51 germline, and the light chain (SEQ ID NO: 36) is coming from L6 germline. Two Fab libraries were designed for the affinity maturation of C47B91. One of the Fab libraries is heavy chain library (C47F8L1), adding diversity from de novo V5.0 to the CDR1 and CDR2 in VH of C47B91 (Table 7); and another Fab library is light chain library (C47F18L1), adding VL diversity from de novo V5.0 based on the VL germline (L6) of C47B91 (Table 8). The Fab libraries were constructed in a pIX phage display system as described in U.S. Pat. No. 6,472,147 and International application No. WO09/085462 with minor modifications to restriction enzyme sites for cloning purposes.

TABLE 7

Affinity maturation design for the light chain library

| Loop | Position | Parent (L6) | VL library diversification scheme |
|---|---|---|---|
| L1 | 30 | S | D, N, R, S |
| | 31 | S | N, S, T |
| | 32 | Y | D, N, R, S, Y |
| L2 | 49 | Y | E, H, K, Y |
| | 50 | D | D, G, S, W, Y |
| | 53 | N | D, N, S, T, Y |
| L3 | 91 | R | A, D, E, G, H, N, R, S, W, Y |

TABLE 7-continued

Affinity maturation design for the light chain library

| Loop | Position | Parent (L6) | VL library diversification scheme |
|---|---|---|---|
| | 92 | S | A, D, E, G, H, N, R, S, W, Y |
| | 93 | N | A, D, E, G, H, N, R, S, W, Y |
| | 94 | W | A, D, E, G, H, N, R, S, W, Y |
| | 96 | L | F, I, L, N, R, W, Y |

TABLE 8

Affinity maturation design for the heavy chain library

| Loop | Position (Kabat) | Parent (5-51) | VH library diversification Scheme |
|---|---|---|---|
| H1 | 30 | T | D, K, T |
| | 31 | S | D, N, S, T |
| | 32 | Y | A, D, S, Y |
| | 33 | W | A, D, G, S, W, Y |
| | 35 | G | G, H, N, S |
| H2 | 50 | I | A, E, I, N, R, T, W, Y |
| | 52 | Y | A, D, L, N, R, Y |
| | 55 | D | D, E, N, S, Y |
| | 57 | D | D, N, R, S, T, Y |
| | 59 | R | E, G, Q, R, Y |
| H3 | 93 | M | V |

Affinity maturation Fab libraries displayed on phage coat protein IX was panned against CHO-S mammalian cells expressing full length of human CD47. The phage library was pre-cleared with $1 \times 10^8$ CHO-S parental cells by incubating together in 10% FBS/DMEM at 4° C. overnight. Pre-cleared libraries were recovered through centrifugation to remove the CHO-S parental cells, and concentrated by PEG/NaCl precipitation. About $1 \times 10^7$ CHO-S CD47 expressing cells were used for each round of panning, panning was about 2 hours at 4° C. Cells binding with the phage were washed with 40% Ficoll/2% BSA in PBS once, and 3 times with ice-cold PBS/0.2% FBS. Round 1 and 2 used the CHO-S CD47 higher expressing clone, while round 3 used either the CHO-S CD47 higher expressing clone or low expressing clone in order to enrich tighter binders. Same libraries were also used to pan with biotinylated CD47 human CD47 ECD monomer. The panning was performed for one hour at 25° C., and the antigen concentrations were at 1 nM for round 1, 0.1 nM for round 2 and 0.1 nM or 0.01 nM for round 3. Binders were retrieved by addition of Strepavidin-beads to form a bead/antigen/phage complex, which was washed in TBST. Alternatively overnight wash was used in attempt to enrich binders with slower off-rate.

Fab production was induced from phage plasmid DNA enriched after panning. The supernatants containing secreted Fabs were used directly to test for inhibition of recombinant human SIRP alpha binding to human CD47 on Jurkat cells and to check their binding to human CD47 ECD monomer and dimer by ELISA as previously described. The Fab clones were also sequenced to check for their VH and VL identity. Fab hits were selected based on unique sequences, binding activity to ECD proteins, and SIRP alpha-blocking activity.

The $V_H$ from selected Fabs was amplified with framework-specific primers from E. coli clone expressing the Fab of interest using PCR. The amplified fragments were subcloned into mammalian expression vector containing signal peptide for mammalian expression and the human IgG2 Sigma heavy chain constant region. Similarly, the $V_L$ fragments were amplified and were subcloned into a mammalian expression vector containing the kappa light chain constant region. The subcloning was done by Infusion cloning (Clontech) with the following primers: HuG1_DNVH_F551, HuG1_DNVH_R, HuK_DNVL_FA27L6muSP, and HuK_DNVL_R (sequences listed in Table 3). The newly generated $V_H$ and $V_L$ mammalian expression DNA constructs were paired together to generate mAbs for further characterization.

A total of 32 C47B91 affinity matured mAbs were generated through pairing of 10 affinity matured VH chains (SEQ ID NO: 6, and 37-45) with the parent VL chain, 4 affinity matured VL chains (SEQ ID NO: 8, and 46-48) with the parent VH chain or from best chains crosses. They were expressed in HEK 293 Expi cells, purified via Protein-A chromatography, and characterized for SIRP alpha-blocking activity, binding affinity to human and Cyno CD47, and hemagglutination activity. A biochemical assay was conducted to investigate the ability of the variants to block SIRP alpha-binding to CD47. Here, His-tagged CD47-ECD dimer protein was pre-incubated with the mAbs before addition to the SIRP alpha-Fc captured on MSD standard plates and then the amount of CD47 bound was detected by a sheep polyclonal anti-CD47 antibody (R&D systems) combined with an MSD SulfoTag-labeled anti-sheep antibody (Meso Scale Discovery). The SIRP alpha-blocking activity of the antibodies was normalized to the percentage of inhibition relative to the signal of no Ab (maximum binding) and no CD47 (background). The inhibitory activities of these mAbs at 10 μg/ml were shown in Table 9, and 25 out of 32 mAbs demonstrated greater inhibition of SIRP alpha binding than the parent C47B91 at 10 μg/ml. Binding affinities to human and Cyno CD47 were measured by ProteOn as described previously. Most of the variants showed improvement in affinity over the parent C47B91 mAb, with C47B222, C47B223, C27B226 and C47B227 showing the most, 5-7 fold tighter affinity compared to C47B91. Importantly, the off-rates were significantly improved with some of these variants. Some of the variants did induce hemagglutination, suggesting that variations in the CDR sequences may also contribute to hemagglutination activity. The data for SIRP alpha-blocking, binding affinities to human and Cyno CD47, and hemagglutination are summarized in Table 8.

TABLE 9

Characterization of 32 C47B91 AM variants for SIRP alpha-blocking, affinity to human CD47 and cyno CD47, and hemagglutination activities. The lowest concentrations at which hemagglutination was visibly observed are indicated where appropriate. For C47B214, C47B218, C47B241, C47B242, C47B243, and C47B244, two donors were tested, and one donor demonstrated hemagglutination in response to these mAbs.

| C47B91 AM Ab | % SIRP alpha Inhibition | Human CD47 KD (M) | Cyno CD47 KD (M) | KD Ratio Cyno/ Human | Hemagglutination |
|---|---|---|---|---|---|
| C47B213 | 71.6 | 2.33E-09 | 4.25E-09 | 1.8 | Y ≥3.125 μg/ml |
| C47B214 | 99.7 | 2.30E-09 | 1.40E-09 | 0.6 | Y/N |
| C47B215 | 99.6 | 2.05E-09 | 1.44E-09 | 0.7 | N |
| C47B216 | 99.8 | 3.35E-09 | 2.74E-09 | 0.8 | N |
| C47B217 | 83.1 | 7.67E-09 | 5.56E-09 | 0.7 | N |
| C47B218 | 98.9 | 2.56E-09 | 1.58E-09 | 0.6 | Y/N |
| C47B219 | 99.4 | 2.58E-09 | 1.66E-09 | 0.6 | N |
| C47B220 | 98.6 | 4.30E-09 | 3.74E-09 | 0.9 | N |
| C47B221 | 95.0 | 5.21E-09 | 4.50E-09 | 0.9 | N |

TABLE 9-continued

Characterization of 32 C47B91 AM variants for SIRP alpha-blocking, affinity to human CD47 and cyno CD47, and hemagglutination activities. The lowest concentrations at which hemagglutination was visibly observed are indicated where appropriate. For C47B214, C47B218, C47B241, C47B242, C47B243, and C47B244, two donors were tested, and one donor demonstrated hemagglutination in response to these mAbs.

| C47B91 AM Ab | % SIRP alpha Inhibition | Human CD47 KD (M) | Cyno CD47 KD (M) | KD Ratio Cyno/ Human | Hemagglutination |
|---|---|---|---|---|---|
| C47B222 | 99.9 | 1.12E-09 | 8.42E-10 | 0.8 | N |
| C47B223 | 100.0 | 1.14E-09 | 8.07E-10 | 0.7 | N |
| C47B224 | 99.7 | 2.46E-09 | 2.19E-09 | 0.9 | N |
| C47B225 | 96.3 | 3.31E-09 | 3.76E-09 | 1.1 | Y ≥3.125 μg/ml |
| C47B226 | 100.0 | 8.72E-10 | 5.43E-10 | 0.6 | N |
| C47B227 | 100.0 | 9.02E-10 | 5.74E-10 | 0.6 | N |
| C47B228 | 99.3 | 2.69E-09 | 2.53E-09 | 0.9 | N |
| C47B229 | 16.1 | 2.15E-09 | 8.32E-09 | 3.9 | Y ≥1.563 μg/ml |
| C47B230 | 28.4 | 1.99E-09 | 7.28E-09 | 3.7 | Y ≥1.563 μg/ml |
| C47B231 | 83.7 | 1.13E-08 | 1.23E-08 | 1.1 | N |
| C47B232 | 99.6 | 2.80E-09 | 2.42E-09 | 0.9 | N |
| C47B233 | 98.4 | 3.90E-09 | 3.02E-09 | 0.8 | N |
| C47B234 | 86.6 | 4.49E-09 | 7.93E-09 | 1.8 | N |
| C47B235 | 99.9 | 2.35E-09 | 3.06E-09 | 1.3 | Y ≥0.781 μg/ml |
| C47B236 | 9.8 | 2.92E-09 | 1.46E-08 | 5.0 | N |
| C47B237 | 97.9 | 2.57E-09 | 3.51E-09 | 1.4 | N |
| C47B238 | 99.1 | 3.53E-09 | 3.73E-09 | 1.1 | N |
| C47B239 | 96.7 | 6.69E-09 | 9.70E-09 | 1.4 | N |
| C47B240 | 93.0 | 8.59E-09 | 9.23E-09 | 1.1 | N |
| C47B241 | 99.8 | 2.62E-09 | 2.03E-09 | 0.8 | Y/N |
| C47B242 | 99.1 | 3.47E-09 | 3.46E-09 | 1.0 | Y/N |
| C47B243 | 99.8 | 2.02E-09 | 2.08E-09 | 1.0 | Y/N |
| C47B244 | 99.8 | 2.12E-09 | 1.55E-09 | 0.7 | Y/N |
| C47B91 | 82.6 | 5.95E-09 | 1.78E-08 | 3.0 | N |

Example 6

Epitope and Paratope Identification by X-Ray Crystallography

The detailed epitopes and paratopes of antibodies C47B161, C47B167, C47B222, C47B227 and B6H12.2 were determined by co-crystallization of their corresponding Fabs with the CD47 ECD-C15G mutant [(SEQ ID NO: 49) hereafter simply CD47] and structure determination by X-ray crystallography. C47B167 was derived from human framework adaption of C47B131 of epitope bin 3 using a similar approach as described for C47B116 in example 4. It blocks SIRPalpha binding ($EC_{50}$=0.79 pg/ml), binds to human CD47 with moderate affinity (kD=5.2 nM) and does not induce hemagglutination.

The His-tagged C47B161, C47B167, C47B222, C47B227 Fabs were expressed in HEK293 cells and purified using affinity and size exclusion chromatography. The His-tagged CD47 was deglycosylated and further purified by affinity chromatography. The complex CD47:Fab was prepared by mixing Fabs with excess CD47 at a molar ratio ranging from 1.2:1.0 to 1.5:1.0. The complex was incubated overnight at 4° C., separated from the uncomplexed species using size exclusion chromatography, and concentrated to 7.5-20 mg/mL in 20 mM HEPES pH 7.4, 100 mM NaCl, 5% glycerol. The concentrated complex was then used to set up crystallization trials using the sitting drop method at 20° C. and crystals were optimized by varying the protein to reservoir ratio. The optimized crystallization conditions for each of the Fab-CD47 complexes are listed in Table 10.

TABLE 10

Crystallization Conditions for the CD47/Fab complexes.

CD47/C47B161 Complex

CD47 was treated with 200 mU endoH/mg of CD47 (endoH from Sigma E7642) and the fully deglycosylated protein was purified in Concanavalin A Sepharose 4B (GE 17-0440-03) and buffer exchanged to 50 mM Tris pH 8, 50 mM NaCl (ELN CD47-2013-196). The CD47/C47B161 complex was then prepared by mixing deglycosylated CD47 with C47B161 at a molar ratio of 1.2:1.0 (excess CD47), incubated at 4° C. overnight, purified by size-exclusion chromatography, and concentrated to 7.5 mg/mL in 20 mM Hepes pH 7.4, 0.1M NaCl, 5% glycerol. Crystals suitable for X-diffraction were obtained from 34% PEG 8 kDa, 0.1M Hepes pH 7.5 using the sitting drop vapor-diffusion method at 20° C.

CD47/C47B167 Complex

The complex was prepared by mixing CD47 with C47B167 at a molar ratio of 1.2:1.0 (excess CD47), incubated at 4° C. overnight, buffer exchanged to 20 mM Tris pH 7.5, and then eluted from monoS with a gradient of 43-53 mM NaCl in 20 mM Tris pH 7.5 and concentrated to 15 mg/mL. Crystals suitable for X-diffraction were obtained from 18% PEG 3 kDa, 0.2M ($(NH_4)_2SO_4$, 0.1M Mes pH 6.5 using the sitting drop vapor-diffusion method at 20° C.

CD47/C47B222 Complex

The complex was prepared by mixing CD47 with C47B222 at a molar ratio of 1.5:1.0 (excess CD47), incubated at 4° C. overnight, buffer exchanged to 20 mM Tris pH 7.5, and then eluted from monoS with a gradient of 43-61 mM NaCl in 20 mM Tris pH 7.5 and concentrated to 17 mg/mL. Crystals suitable for X-diffraction were obtained from 25% PEG 3k, 1M LiCl, 0.1M Mes pH 6.5 using the sitting drop vapor-diffusion with microseed matrix screening method[10] at 20° C.

CD47/C47B227 Complex

The CD47/C47B227 complex was prepared similarly to the C47B167 complex. Crystals suitable for X-diffraction were obtained from 4.5M Na Formate, 0.1M Tris pH 8.5 using the sitting drop vapor-diffusion with microseed matrix screening method[10] at 20° C. and the complex at 11 mg/mL.

CD47/B61112.2 Complex

The complex was prepared similarly to the C47B167 complex, with the exception of B6H12.2 complex being eluted from monoS with a gradient of 119-137 mM NaCl in 20 mM Hepes pH 7.0 and concentrated to 3 mg/mL. Crystals suitable for X-diffraction were obtained from 2.4M $(NH_4)_2SO_4$, 0.1M Na Acetate pH 5.5 using the sitting drop vapor-diffusion with microseed matrix screening method[10] at 20° C.

C47B161, C47B167, C47B222, C47B227 Fabs

C47B161, C47B167 and C47B227 were respectively, concentrated to 8, 17 and 20 mg/mL without further purification. Crystals suitable for X-diffraction were obtained from the conditions listed in Table 2 using the sitting drop vapor-diffusion method at 20° C. (ELN CD47-2013-219). In the case of C47B222, the best quality dataset (described in Table 2) was derived from a crystal that was set up to be of a CD47/C47B222 complex but, instead contained only the free Fab. This CD47/C47B222 complex was prepared similarly to the C47B222 complex described previously, with the difference of the complex being eluted from monoS with a gradient of 119-145 mM NaCl in 20 mM Hepes pH 7.0 and concentrated to 23 mg/mL.

For X-ray data collection, one crystal was soaked for a few seconds in a cryo-protectant solution containing crystallization solution supplemented with 20% glycerol, and flash frozen in the stream of nitrogen at 100 K. Diffraction data were collected at the Dectris Pilatus 6M Pixel Array detector at the beamline 17-ID of the Advanced Photon Source (APS) at Argonne National Laboratory over a 240° crystal rotation with 2-min exposures per 0.25°-image and were processed with the program HKL2000. X-ray data statistics are given in Tables 11 and 12.

TABLE 11

Crystal data, X-ray data and refinement statistics for the CD47/Fab complexes.

| Complex | CD47/C47B161 | CD47/C47B167 | CD47/C47B222 | CD47/C47B227 | CD47/B6H12.2 |
|---|---|---|---|---|---|
| Crystal data | | | | | |
| Crystallization solution | | | | | |
| 0.1M Buffer | Hepes pH | Mes pH 6.5 | Mes pH 6.5 | Tris pH 8.5 | Acetate pH |
| Precipitant | 34% PEG 8K | 18% PEG 3K | 25% PEG 3K | 4.5M NaFormate | 2.4M $(NH_4)_2SO_4$ |
| Additive | | 0.2M $(NH_4)_2SO_4$ | 1M LiCl | | |
| Space group | $P2_1$ | $P2_12_12$ | $P2_1$ | $P2_1$ | C2 |
| Complex/asym.unit | 2 | 4 | 1 | 2 | 1 |
| Unit cell | | | | | |
| a (Å) | 74.56 | 173.61 | 60.57 | 94.95 | 161.76 |
| b (Å) | 60.97 | 210.84 | 72.93 | 63.55 | 54.53 |
| c (Å) | 124.13 | 89.37 | 72.70 | 142.00 | 83.49 |
| β (°) | 90.05 | 90.00 | 108.96 | 102.50 | 95.89 |
| $V_m$ (Å$^3$/Da) | 2.0 | 3.0 | 2.2 | 3.0 | 2.7 |
| Solvent content (%) | 39 | 59 | 45 | 59 | 54 |
| X-ray data* | | | | | |
| Resolution (Å) | 50.00-2.90 | 50.00-2.90 | 50.00-2.30 | 50.00-3.00 | 40.00-2.10 |
| High Resolution Shell (Å) | (2.95-2.90) | (2.95-2.90) | (2.34-2.30) | (3.05-3.00) | (2.14-2.10) |
| Measured reflections | 77,044 | 476,433 | 82,617 | 94,048 | 130,229 |
| Unique reflections | 24,865 | 72,505 | 26,271 | 32,700 | 42,025 |
| Completeness (%) | 98.6 (90.9) | 100 (100) | 98.8 (97.0) | 98.6 (98.6) | 98.7 (99.1) |
| Redundancy | 3.1 (2.9) | 6.6 (6.3) | 3.1 (2.8) | 2.9 (2.3) | 3.1 (3.0) |
| Rsym (%) | 11.9 (46.5) | 18.0 (72.9) | 8.3 (43.2) | 16.5 (53.6) | 10.5 (36.8) |
| <I/σ> | 9.1 (2.0) | 12.0 (3.1) | 12.8 (2.4) | 7.2 (2.1) | 10.8 (4.2) |

TABLE 11-continued

Crystal data, X-ray data and refinement statistics for the CD47/Fab complexes.

| Complex | CD47/ C47B161 | CD47/ C47B167 | CD47/ C47B222 | CD47/ C47B227 | CD47/ B6H12.2 |
|---|---|---|---|---|---|
| Refinement | | | | | |
| Resolution (Å) | 41.4-2.9 | 45.0-2.9 | 32.2-2.3 | 41.3-3.0 | 38.6-2.1 |
| Number of reflections | 24,832 | 72,349 | 26,217 | 32,646 | 41,995 |
| Number of all atoms | 8,243 | 17,321 | 4,291 | 7,358 | 4,441 |
| Number of waters | 57 | 195 | 99 | 10 | 208 |
| Rfactor (%) | 24.9 | 18.7 | 18.8 | 20.9 | 18.2 |
| Rfree (%) | 29.7 | 24.1 | 24.4 | 26.6 | 22.9 |
| RMSD | | | | | |
| bond lengths (Å) | 0.003 | 0.003 | 0.003 | 0.009 | 0.007 |
| bond angles (°) | 0.768 | 0.697 | 0.712 | 1.516 | 1.119 |
| Wilson B-factor (Å$^2$) | 53.18 | 38.90 | 49.94 | 66.83 | 25.4 |
| MolProbity | | | | | |
| Ramachandran favored (%) | 93.93 | 96.06 | 95.87 | 94.22 | 97.76 |
| Ramachandran allowed (%) | 5.70 | 3.62 | 4.13 | 5.57 | 2.24 |
| Ramachandran outliers (%) | 0.37 | 0.32 | 0.00 | 0.21 | 0.00 |
| Rotamer outliers (%) | 0.00 | 0.38 | 0.89 | 0.38 | 0.64 |
| Clash score | 6.69 | 2.74 | 3.16 | 6.62 | 3.47 |

*Values for high resolution shell are in parenthesis.

TABLE 12

Crystal data, X-ray data and refinement statistics for the free Fabs.

| Fab | C47B161 | C47B167 | C47B222 | C47B227 |
|---|---|---|---|---|
| Crystal data | | | | |
| Crystallization solution | | | | |
| 0.1M Buffer | Mes pH 6.5 | Acetate pH 4.5 | Tris pH 8.5 | Tris pH 8.5 |
| Precipitant | 24% PEG 3K | 25% PEG 3K | 2.4M (NH$_4$)$_2$SO$_4$ | 2.4M (NH$_4$)$_2$SO$_4$ |
| Additive | 1M Na Acetate | 0.2M (NH$_4$)$_2$Ac | 5% MPD | 5% MPD |
| Space group | P2$_1$2$_1$2$_1$ | P2$_1$2$_1$2$_1$ | P2$_1$2$_1$2$_1$ | P2$_1$2$_1$2$_1$ |
| Fab/asym.unit | 1 | 2 | 1 | 1 |
| Unit cell | | | | |
| a (Å) | 56.63 | 73.96 | 63.74 | 62.60 |
| b (Å) | 60.59 | 79.90 | 74.47 | 73.98 |
| c (Å) | 122.97 | 144.40 | 103.98 | 114.04 |
| V$_m$ (Å$^3$/Da) | 2.1 | 2.1 | 2.6 | 2.6 |
| Solvent content (%) | 42 | 42 | 53 | 53 |
| X-ray data* | | | | |
| Resolution (Å) | 40.00-2.00 | 50.00-2.00 | 50.00-1.60 | 50.00-2.60 |
| High Resolution Shell (Å) | (2.03-2.00) | (2.03-2.00) | (1.63-1.60) | (2.64-2.60) |
| Measured reflections | 176,113 | 370,967 | 388,172 | 104,467 |
| Unique reflections | 28,937 | 58,215 | 65,229 | 16,591 |
| Completeness (%) | 99.2 (96.5) | 99.1 (97.3) | 97.5 (88.5) | 98.8 (97.3) |
| Redundancy | 6.1 (5.1) | 6.4 (5.7) | 6.0 (5.1) | 6.3 (6.1) |
| Rsym (%) | 5.4 (14.9) | 5.7 (24.6) | 8.6 (29.2) | 11.8 (60.4) |
| <I/σ> | 26.9 (10.6) | 27.7 (8.3) | 16.4 (5.2) | 14.8 (3.8) |
| Refinement | | | | |
| Resolution (Å) | 34.3-2.0 | 35.0-2.0 | 35.0-1.6 | 33.8-2.6 |
| Number of reflections | 28,865 | 58,140 | 65,163 | 16,518 |
| Number of all atoms | 3,427 | 6,840 | 3,581 | 3,268 |
| Number of waters | 105 | 173 | 325 | 75 |
| Rfactor (%) | 19.4 | 19.8 | 17.05 | 18.18 |
| Rfree (%) | 24.0 | 24.8 | 19.79 | 27.24 |

TABLE 12-continued

Crystal data, X-ray data and refinement statistics for the free Fabs.

| Fab | C47B161 | C47B167 | C47B222 | C47B227 |
|---|---|---|---|---|
| RMSD | | | | |
| bond lengths (Å) | 0.007 | 0.007 | 0.014 | 0.007 |
| bond angles (°) | 1.209 | 1.148 | 1.625 | 1.128 |
| Wilson B-factor (Å$^2$) | 26.86 | 28.03 | 18.68 | 38.57 |
| MolProbity | | | | |
| Ramachandran favored (%) | 98.38 | 97.33 | 98.09 | 95.93 |
| Ramachandran allowed (%) | 1.39 | 2.67 | 1.91 | 3.83 |
| Ramachandran outliers (%) | 0.23 | 0.00 | 0.00 | 0.24 |
| Rotamer outliers (%) | 1.07 | 0.80 | 0.28 | 0.29 |
| Clash score | 2.59 | 1.60 | 2.03 | 5.76 |

*Values for high resolution shell are in parenthesis.

The Overall Structures

The structural models for the CD47 molecules include residues from 1 to at least 114, corresponding to the IgV domain, and glycans in positions 5, 16, 32, 55, and 93, except for CD47 in the C47B161 Fab complex with no visible glycans. The CD47 C-terminal 6× His (SEQ ID NO: 55) is disordered. The Fab structural models contain residues from 1 to at least 211 for the light chain and from 1 to at least 217 for the heavy chain. The Fab C-terminal 6× His tag (SEQ ID NO: 55) and inter-chain disulfide bond are disordered. In the case of the C47B222/C47B227 heavy chains, residues 135-140 are also disordered. The antibody/antigen combining site is well defined by electron density in all 5 complexes, which allows reliable positioning of the binding residues. The Fabs are numbered sequentially in all figures and CD47 numbering starts at the N-terminus of the mature protein.

The CD47 molecules in the Fab complexes superimposed among themselves and with CD47 bound to SIRP alpha (Hatherley, 2008) with RMSD of 0.45-0.98 Å, indicating a high degree of structural similarity of CD47 in the various complexes and absence of large conformational changes induced by Fab or receptor binding.

The Epitopes, Paratopes and Antibody/Antigen Interactions

C47B161, C47B167, and C47B222/C47B227/B6H12.2 bind to 3 distinct epitope bins as revealed by antibody competition binning assays. C47B222 and C47B227 bind to the same overall location, while C47B167 binds closer to the cell membrane and C47B161 and B6H12.2 bind to a more apical region of CD47. Binding to an epitope closer to the membrane can cause additional constraints to the Fab that might propagate to the 2$^{nd}$ Fab arm in the antibody and make binding of this arm to another CD47 molecule more challenging. We speculate that constraints to the 2$^{nd}$ Fab arm due to epitope location could translate into less cell aggregation from CD47/antibody/CD47 cross-linkings. In the case of the C47B222 Fab, the HC has more extensive contacts with CD47 than the LC and it is the chain closer to the membrane.

The epitope and paratope sequences are shown in FIG. 6. The details of the interaction made between CD47 and each of the Fabs is discussed in detail below.

CD47/C47B161 Complex

C47B161 recognizes a conformational epitope composed of residues in the CD47 N-terminal (Q1 and L3), BC (N27 and E29) and FG (residues 101-103) loop regions and the F (residue E97) and G (E104) β-strands as seen in FIG. 7. M259 binds to epitope bin 2 region and covers an area of about 690 Å$^2$ on CD47.

The paratope is composed of residues from five CDRs except CDR-L3. The LC is positioned mostly on the CD47 β-sheet, while the HC covers the apical loop regions of the antigen. In comparison to the other anti-CD47 Fabs under evaluation, C47B161 has a long CDR-L1 with an insertion of six residues at position 30. The Y35 and Y37 residues near the tip of the CDR-L1 loop enhance the affinity of the antibody for its antigen by H bonding the β-sheet of CD47 (FIG. 7C). The other residues at the L1 loop tip (H31 and N33 residues), are not involved in direct contact with CD47 but, they play an important role in orienting Y35 and, specially, Y37 for effective interaction with CD47. On the VH side, all CDRs are involved in interactions with the antigen, particularly with the N-terminus Q1 residue, which is cyclized as pyroglutamate, and the 27-29 and 102-103 loop segments (FIGS. 7B and 7D).

CD47/C47B167 Complex

C47B167 recognizes a conformational epitope composed of residues of the C (Y37 and K39), C' (R45, D46 and T49) and C" (N55-T58) β-strands and CC" (A53, L54) and C"E (V59-T61, S64, A66, K67) loop regions as shown in FIG. 8. C47B167 binds to the epitope bin 3 region and covers an area of about 930 Å$^2$ on CD47.

The C47B167 paratope is made of residues from all six CDRs. The C and C' β-strands (Y37, K39, R45, D46 and T49) interact only with the LC CDRs, while the loop region 64-67 is contacted only by the long CDR-H3 (9 residue insertion).

Figure 8A:
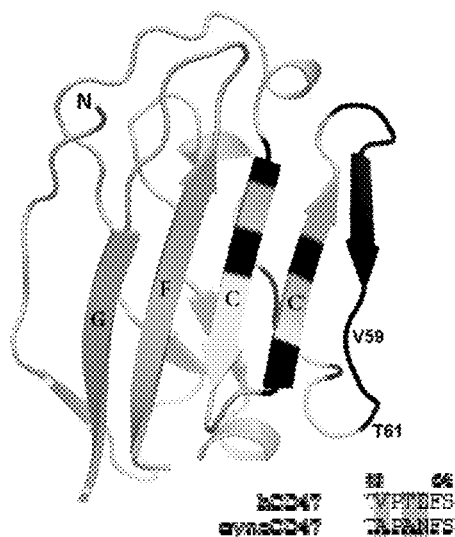
FIG. 8A-8D. Epitope location and interactions between CD47 and C47B167. C47B167 recognizes the epitope bin 3 region in black. The antibody binds well to human CD47 (SEQ ID NO: 67) and weakly to cyno CD47 (SEQ ID NO: 68) due to sequence differences in the V59-T61 epitope region (FIG. 8A). 2D Interaction map between CD47 and C47B167. Van der Waals interactions are shown as dashed lines, H bonds are solid lines with arrows indicating backbone H bonds and pointing to the backbone atoms. CD47, VL and VH residues are in gray boxes, white boxes and ovals, respectively. A distance cut-off of 4 Å was used to define the contacting residues (FIG. 8B). CD47 main interactions with the Fab light (FIG. 8C) and heavy (FIG. 8D) chains. H-bonds are shown as dashed lines. CD47 residues are underlined.
Figure 8B:
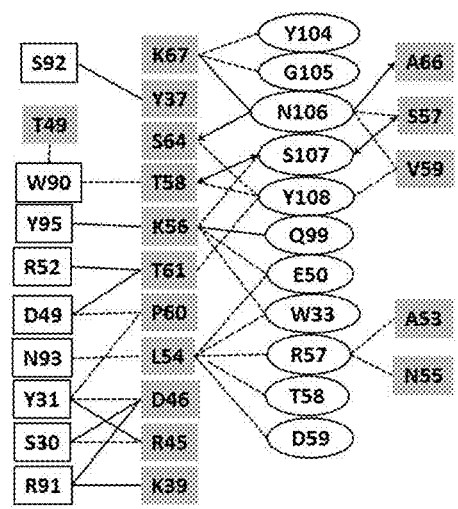
Figure 8C:
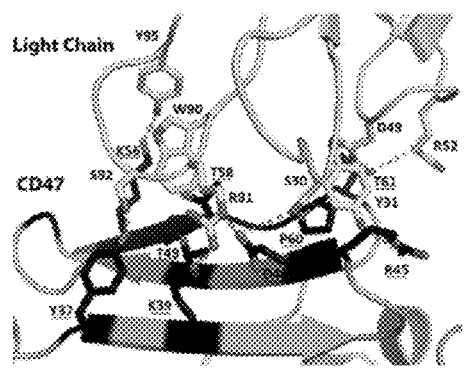
Figure 8D:
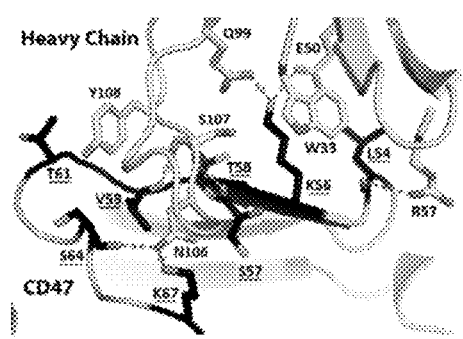

C47B167 has reduced cross-reactivity to cyno monkey CD47 due to sequence divergence in the epitope region V59-T61 (see stretch of sequence alignment in FIG. 8A). The T61A human to cynoCD47 change kills the H bonds between residue 61 and LC residues D49 and R52 in cyno (FIG. 8C). Additionally, a potential N-linked glycosylation site in position 62 of cyno CD47 (and not in human) could create steric hindrance for antibody binding to the V59-T61 region. The V59A change should have a minor impact (FIG. 8D).

Figure 9A:
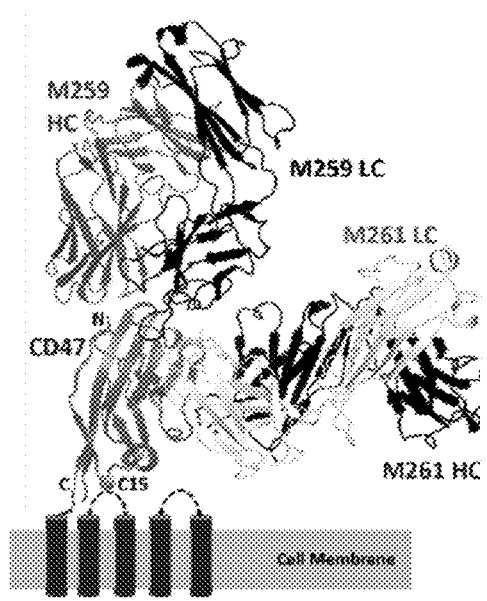
FIGS. 9A and 9B. CD47 bound to both C47B161 and C47B167. The ternary complex was achieved by superposition of equivalent CD47 Ca atoms in both complexes (FIG. 9A). There is no epitope overlap between the 2 antibodies (FIG. 9B). The CD47 structure from the C47B167 complex is shown in FIG. 9B. The C47B167 epitope is shown in black and the C47B161 epitope is in white.
Figure 9B:
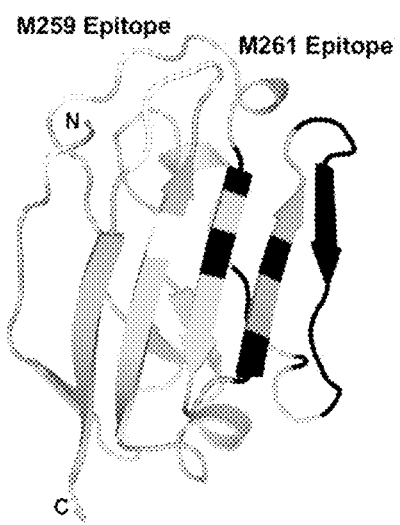
Figure 12A:
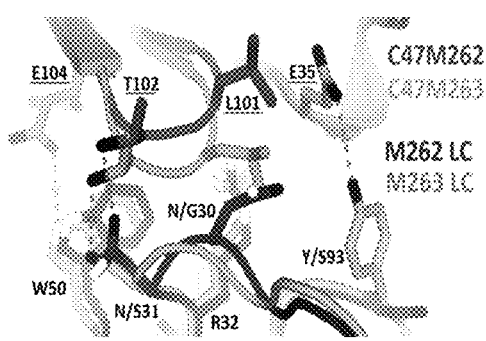
FIGS. 12A and 12B. Epitope and paratope differences between C47B222 and C47B227. Differences in the light chain interactions: N30G, N31S and Y93S mutations in CDR-L1 and CDR-L3 result in repositioning of the FG loop of CD47 and changes in the H bond pattern (FIG. 12A). Differences in the heavy chain interactions: A different conformation for the CDR-H3 loop of C47B222 increases the number of H bonds made by the H3 loop from none in C47B227 to 4 bonds in C47B222 (with CD47 residues Y37, K39, D46 and D51). The structural overlay was achieved by superposition of equivalent CD47 Ca atoms in both complexes. The CD47 residues are underlined (FIG. 12B).
Figure 12B:
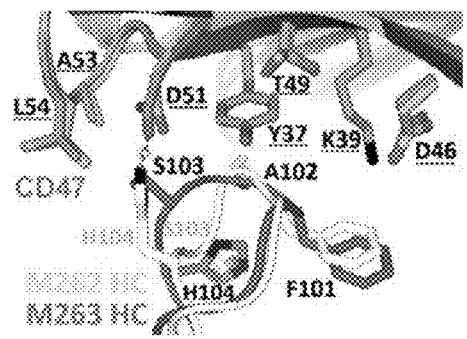
Figure 13A:
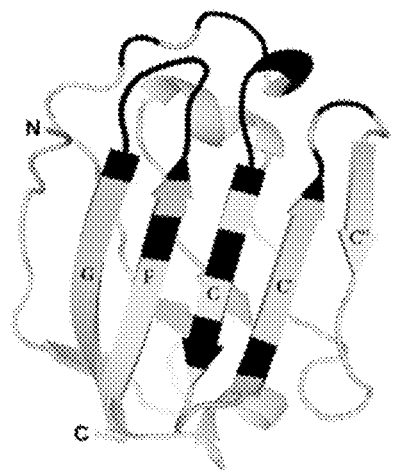
FIGS. 13A-13D. Epitope location and interactions between CD47 and B6H12.2. Epitope overall location. B6H12.2 binds to the epitope bin 1 region shown in black (FIG. 13A). 2D Interaction map between CD47 and B6H12.2: Van der Waals interactions are shown as dashed lines, H bonds are solid lines with arrows indicating backbone H bonds and pointing to the backbone atoms. CD47, VL and VH residues are in gray boxes, white boxes and ovals, respectively. A distance cut-off of 4 Å was used to define the contacting residues (FIG. 13B). CD47 main interactions with the Fab Light (FIG. 13C) and Heavy (FIG. 13D) chains. H-bonds are shown as dashed lines. CD47 residues are underlined.
Figure 13B:
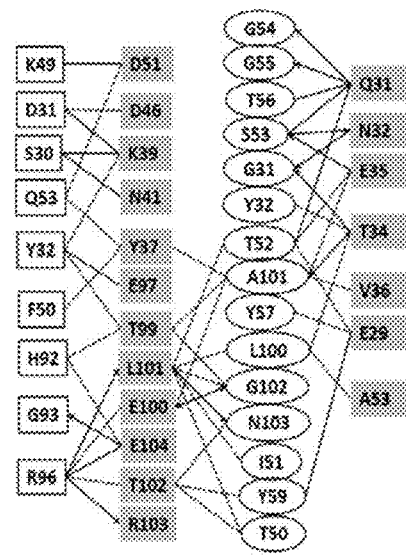
Figure 13C:
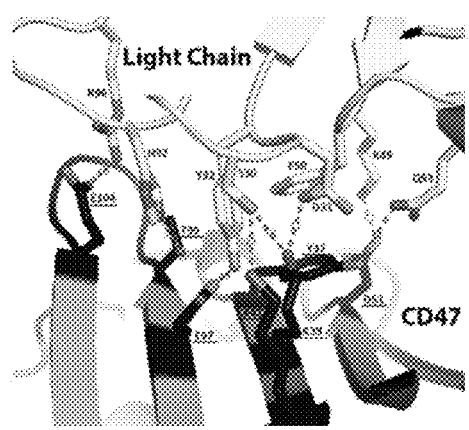
Figure 13D:
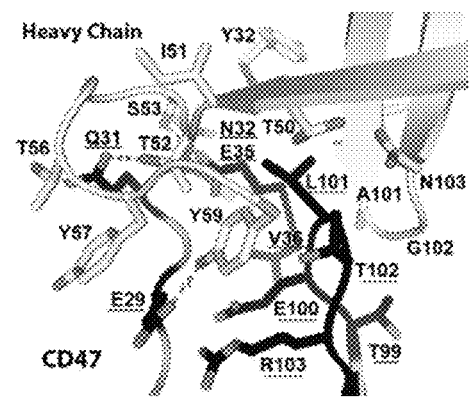

There is no common residue between the epitope bins 2 and 3. C47B161 (bin 2) and C47B167 (bin 3) can bind simultaneously to CD47 without any clash regions as shown in FIG. 9. This result has also been demonstrated using antibody competition binning assays (see Example 3). C47B167 recognizes a larger area of the CD47 β-sheet than C47B161 and binds considerably closer to the cell membrane.

CD47/C47B222 and CD47/C47B227 Complexes

C47B222 recognizes a conformational epitope composed of residues of the C (Y37 and K39), C' (D46, T49, D51), C" (I56, T58) and F (T99) β-strands and the BC (E35), C'C" (A53 and L54), C"E (V59), and FG (L101, T102) loop regions as shown in FIG. 10. The epitope of C47B222 is located in the bin 1 region and covers a CD47 area of about 730 Å$^2$. C47B222 competes for CD47 binding with C47B161, C47B167, C47B227 and B6H12.2. The regions of C47B222 epitope overlap with the other epitopes are displayed in FIG. 6.

The C47B222 paratope is composed of residues from all CDRs except CDR-L3. The majority of the C47B222 interactions with CD47 are made by the heavy chain using a combination of H bonds and van der Waals contacts (FIG. 10). There is clear segregation between the epitope regions recognized by the HC and LC paratopes. The heavy chain interacts exclusively with the C'C" loop and all β-strand epitope regions except for the F strand. The light chain binds, also with exclusivity, the BC and FG loops and the F strand, occupying a more apical position on CD47 that serves to block SIRP alpha binding to CD47 very effectively. Leucine 54 in the C'C" loop is in a central location of the combining site and contacts all three heavy chain CDRs (FIG. 10B). The C" strand hydrogen bonds CDR-H2 and the C and C' β-strands contact CDR-H3.

The C47B227 conformational epitope is also located in bin 1. The epitope covers a CD47 area of about 800 $Å^2$ composed of residues of all strands of the β-sheet (strand C: Y37; strand C': T49 and D51; strand C": N55, K56 and T58; strand F: T99; strand G: E104) and segments of the BC (E35), C'C" (residue range 53-55) and FG (L101, T102) loop regions as shown in FIG. 11.

The C47B227 paratope is composed of residues from all CDRs. Similar to C47B222, the heavy chain of C47B227 interacts exclusively with the C, C', and C" β-strands and most of the C'C" loop region—the exception is A53, which is in the C'C" loop and has a van der Waals contact with CDR-L3. The light chain of M263 binds to the F and G strands and the BC and FG loops. C47B222 and C47B227 bind to CD47 with a similar orientation and share many epitope and paratope residues (FIG. 6).

C47B222 has 97% sequence identity to C47B227 with 6 amino acid changes in the regions near or at the CDRs (HC: T30D and LC: N30G, N31S, H49Y, I56T and S93Y changes from C47B222 to C47B227. See FIG. 6). Nevertheless, C47B222 and C47B227 bind to CD47 with the same overall orientation and recognize roughly the same epitope region with similar affinity (about 1 nM). This epitope tolerance to different light chains is a direct consequence of the C47B222/C47B227 recognition of CD47 being heavily based on the HC contacts and the separation between the epitope regions recognized by the HC and LC paratopes (epitope segregation). Furthermore, the effective number of residues changes between C47B222 and C47B227 is only three (N30G, N31S and S93Y) since the heavy chain T30D and light chain H49Y and I56T changes are too far away (greater than 6 Å) from the combining site to have an effect in CD47 recognition. Replacement of G30 with Asn in C47B222 only induces accommodation of the CD47 FG loop in a slightly different position to avoid steric clashes between L101 and N30 as seen in FIG. 11A. The N31S and S93Y changes create new H bonds with the T102 main chain and E35 in M263, strengthening the interaction of the C47B227 LC with CD47 and contra-balancing the fewer H bonds made by the CDR-H3 of C47B227 in comparison to the C47B222, which adopts a different conformation and uniquely H bonds CD47 residues Y37, K39, D46 and D51 (FIGS. 10-12).

CD47/B6H12.2 Complex

B6H12.2 binds to the epitope bin 1 region and it was used as a control antibody. B6H12.2 recognizes a conformational epitope composed of residues of the C (V36, Y37, K39 and K41), C' (D46, D51), F (E97, T99) and G (E104) β-strands and the BC (E29, Q31, N32, T34 and E35), C'C" (A53) and FG (E100-R103) loop regions as shown in FIG. 10. Unlike C47B222 and C47B227, which were also clustered in bin 1, B6H12.2 does not recognize any residues in neither the C" β-strand nor the C"D loop region. Nevertheless, B6H12.2 has a larger epitope area than C47B161, C47B167, C47B222 and C47B227 (about 1055 $Å^2$ versus 690 $Å^2$ for C47B161, 930 $Å^2$ for C47B167, 730 $Å^2$ for C47B222, and 800 $Å^2$ for C47B227).

The B6H12.2 paratope is composed of residues from all CDRs (FIG. 13). The antibody and antigen recognition appears to be mostly driven by H bonds. The light chain makes 6H bonds with CD47 side chains and 3 with backbone atoms. The heavy chain, on the other hand, is engaged in 13H bonds with CD47, most of them involving backbone atoms. B6H12.2 has a short CDR-H3 that goes deep into the combining site, stabilizes the FG loop and gives space for CDR-H2 to spread on top of the BC loop. The heavy chain contacts with exclusivity the BC (mostly CDR-H2), C'C" (CDR-H3) and most of the FG (CDRs-H2 and H3) loop regions, while the LC contacts exclusively the C' strand and the adjacent C-terminal area of the C strand. However, there is less epitope segregation for B6H12.2 than for C47B222 and C47B227. There are multiple epitope residues in the F strand and FG loop that interact with both HC and LC.

Epitope Summary

Unlike C47B161, B6H12.2 does not recognize the N-terminal region of CD47. Unlike C47B167, C47B222, and C47B227, B6H12.2 does not recognize any residues in either the C" β-strand or the C"D loop regions of CD47 (see FIG. 6). Specifically, the epitope residues of each Fab that do not coincide with the epitope identified for B6H12.2 are:

C47B161: residues in the N-terminal (Q1 and L3) and the BC loop (N27) regions.

C47B167: residues in the β-strand C' (R45 and T49), C'C" loop (L54), β-strand C" (1(56, S57, and T58) and C"D loop (V59, P60, T61, S64 and K67) regions.

C47B222: residues in the β-strand C' (T49), C'C" loop (L54), β-strand C" (K56 and T58) and C"D loop (V59) regions.

C47B227: residues in the C'C" loop (L54) and β-strand C" (K56 and T58) regions.

Example 7

Characterization of CD47 Antibodies

Several human CD47 IgG2sigma antibodies with desired characteristics were converted to an IgG1 Fc format for further evaluation in bioassays. Their IgG1 variants were confirmed to bind to human CD47, and block SIRP alpha-binding. IgG1/IgG2sigma Fc variants that did not induce hemagglutination (C47B222, C47B157, and C47B161) were further evaluated in vitro for enhancement of phagocytosis, apoptosis, complement mediated cytotoxicity (CDC), and platelet aggregation activity. In addition, the anti-tumor activity of these three mAbs was tested in vivo.

Phagocytosis:

In vitro phagocytosis assays were performed to assess whether C47B157, C47B161, and C47B222 enhance phagocytosis of CD47 expressing target cells by human macrophages. Briefly, CD14 positive monocytes were isolated from leukopak purified PBMCs by negative depletion using the Stemcell EasySep human monocyte enrichment kit without CD16 depletion. Purified monocytes were plated at $0.1 \times 10^6$ cells/cm$^2$ in X-VIVO-10 medium (Lonza) supplemented with 10% FBS (Invitrogen) and 25 ng/ml M-CSF (R&D Systems) and were differentiated to macrophages for seven days. IFN-γ (R&D Systems) was added at 50 ng/ml during the final 24 hours of differentiation. Subsequently, adherent macrophages were detached from tissue culture dishes by Accutase (Sigma) treatment and macrophages ($1 \times 10^5$) were plated in 96-well U-bottom plates at a 1:1 ratio with GFP expressing Jurkat cells ($1 \times 10^5$) in the presence of varying concentrations of anti-CD47 mAbs. Cells were incubated at 37° C. for 90 minutes. Upon completion of incubation, cells were washed once with PBS and cells were detached with Accutase (20 minute incubation). Cells were pelleted, washed and macrophages were stained with an APC conjugated anti-human CD11b antibody (eBiosciences) for 30 minutes followed by two washes with stain Buffer (BD Biosciences). Cells were acquired on the MacsQuant flow cytometer. Data was analyzed with the FloJo software. Percent phagocytosis was determined by the following equation [((GFP$^{pos}$, CD11b$^{pos}$ cells)/(GFP$^{pos}$, CD11b$^{pos}$+GFPP$^{pos}$ cells))×100%].

Figure 14:
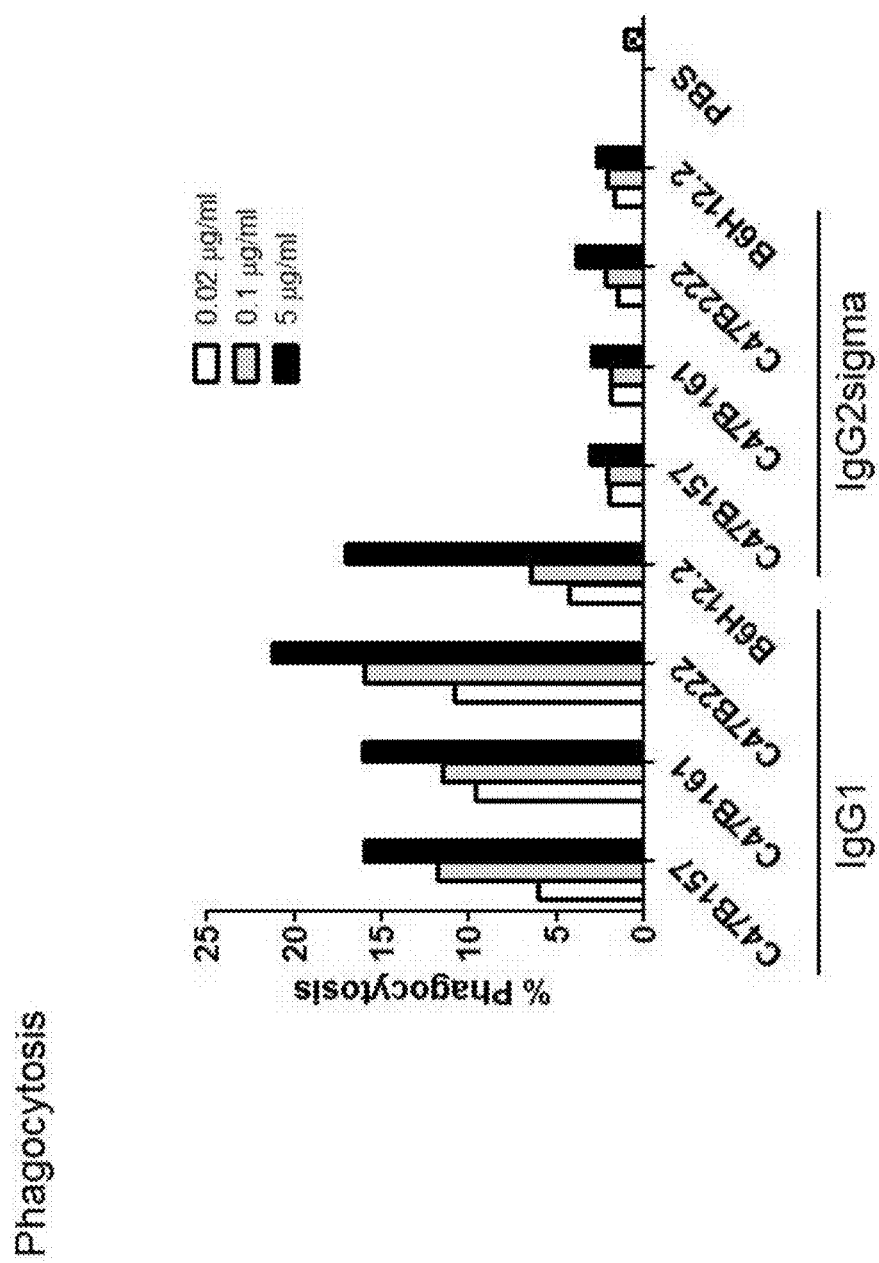
FIG. 14. Phagocytosis of Jurkat target cells by human PBMC derived macrophages in response to 90 minute treatment with varying concentrations of anti-human CD47 IgG1/IgG2 Fc-silent C47B157, C47B161, C47B222, and B6H12.2.

These experiments demonstrated that IgG1 B157, B161, B222 and B6H12.2 demonstrated robust phagocytosis enhancing ability, while IgG2sigma B157, B161, B222, and B6H12.2 (FIG. 14) enhanced phagocytosis minimally.

Apoptosis:

Several anti-CD47 mAbs (e.g., AD-22, 1F7 and MABL-1) have been described to mediate apoptosis of target cells in soluble form upon ligation of CD47. To test whether C47B157, C47B161, and C47B222 mediate apoptosis upon ligation of CD47, Jurkat cells or HL60 cells ($1 \times 10^6$ cells/ml in 100 µl) were incubated for 24 hours at 37° C. in RPMI1640 supplemented with 10% FBS in the presence or absence of antibodies (0.05, 0.5, and 5 µg/ml). Apoptosis was detected with the FITC Annexin-V Apoptosis Detection Kit (BD Pharmingen). Apoptosis was expressed as the sum of early apoptosis (Annexin-V positive/PI negative) and late apoptosis (Annexin-V positive/PI negative).

These experiments revealed that the control mAb B6H12.2 induced robust apoptosis as IgG2sigma in Jurkat and HL60 cells, but not as IgG1 (see FIG. 15). Similarly, C47B157 and C47B161 induced low levels of apoptosis as IgG2sigma in Jurkat cells, but not as IgG1. IgG1/IgG2sigma C47B157 and C47B161 had no proapoptotic effects on HL60 cells. 24 hour treatment of Jurkat and HL60 cells with IgG1 or IgG2sigma C47B222 did not result in apoptosis induction.

Complement Mediated Cytotoxicity:

C47B157, C47B161, and C47B222 were tested for complement mediated cytotoxicity (CDC). CDC assays were performed with Wil2-S target cells. 50,000 Wil2-S cells were plated in opaque white 96-well plates in 25 µl RPMI-1640 supplemented with 10% heat inactivated FBS and 0.1 mM NEAA (all reagents from Invitrogen). Upon addition of 25 µl of medium supplemented with or without antibodies cells were incubated for 30 minutes at 37° C. Subsequently, 50 µl of human serum (Bioreclamation, complement preserved) was added and cells were incubated at 37° C. for 2 hours. To assess maximal lysis 20 µl of 2% Triton-X-100 were added to control wells and cells were incubated at 37° C. for 2 hours. Once the incubation was completed, 100 µl of CellTiter-Glo Reagent (Promega; premixture of buffer and substrate) was added to each well, contents were gently mixed to induce cell lysis and luminescence was recorded on the 2104 EnVision Multilabel reader (Perkin Elmer). Specific lysis was calculated by the following equation: [specific lysis=((Experimental release-spontaneous release)/(maximum release-Spontaneous release))*100].

Figure 16B:
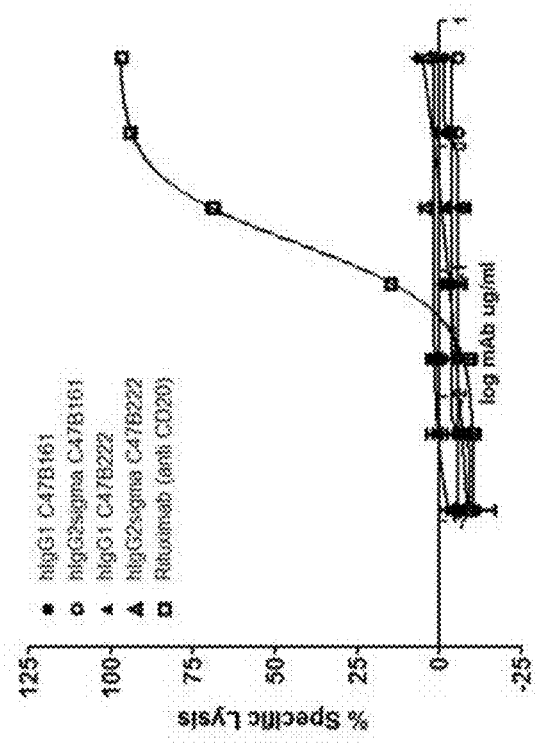
FIGS. 16A and 16B. Enhancement of complement dependent cytotoxicity against Wil2-s target cells in response to varying concentrations of anti-human CD47 IgG1/IgG2 Fc-silent C47B157, C47B161, C47B222, B6H12.2. Rituximab was included as positive control.
Figure 16A:
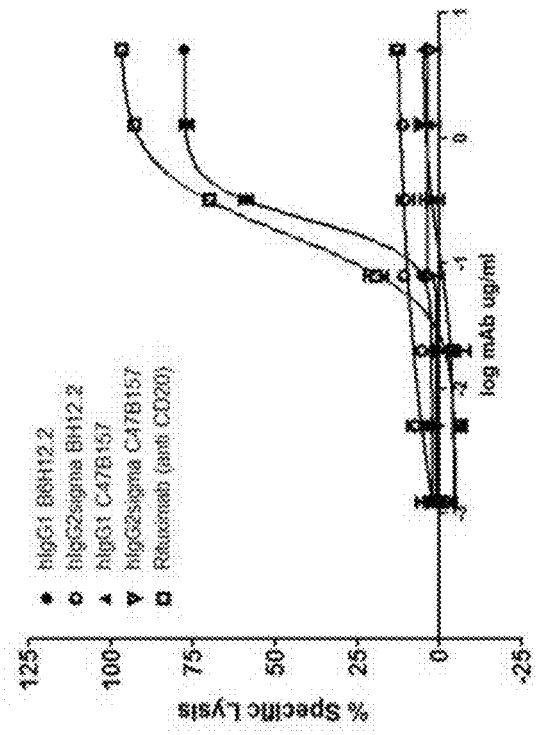

As shown in FIG. 16, IgG1/IgG2sigma C47B157, C47B161, and C47B222 did not enhance CDC as IgG1 or IgG2sigma. In contrast, the tool mAb B6H12.2 IgG1 mediated robust CDC similar to the positive control rituximab, and did not enhance CDC in the effector function silent IgG2sigma backbone.

Platelet Aggregation:

Based on the observation that the commercially available anti-CD47 mAb B6H12 (mIgG1) induced platelet aggregation (Fujimoto T T, Katsutani S, Shimomura T, Fujimura K. (2003) J Biol Chem 278: 26655-26665), assays were established to determine the platelet aggregation activity of C47B157, C47B161, and C47B222. Briefly, blood was collected from healthy donor volunteers into Vacutainer blood collection tubes (BD Biosciences) buffered with sodium citrate. Platelet rich plasma (PRP) and platelet poor plasma (PPP) were prepared with the PDQ platelet function centrifuge (Biodata Corporation) according to the manufacturer's protocol. Platelet aggregation was measured with the PAP-8E aggregometer (Biodata Corporation) as recommended by the manufacturer. Specifically, 25 µl of ADP (positive control; Biodata Corporation) or antibodies were added to 225 µl of PRP for a final concentration of 10 µM ADP or 100, 140, 150, or 200 µg/ml test antibodies (depending on availability of antibody tested). Aggregation was determined by measuring the transmission of light through the 250 µl sample at 37° C. with continuous stirring. The transmission of PPP was set as 100%. Aggregation was recorded for a total of 6 minutes.

Figure 17A:
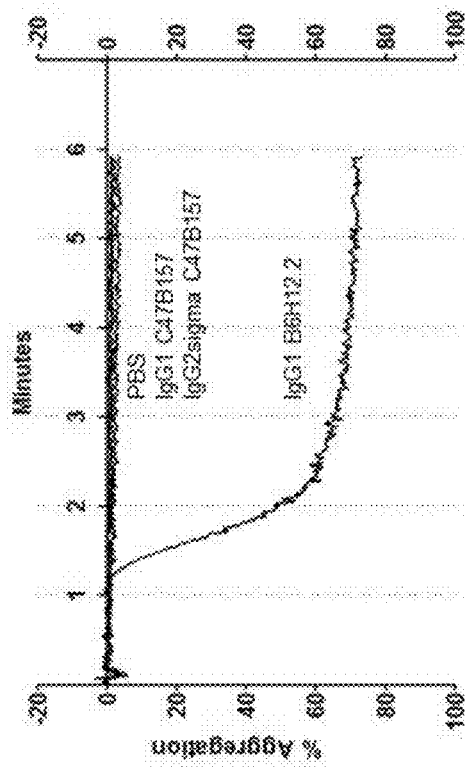
FIGS. 17A-17D. Aggregation of human platelets in response to incubation of platelet rich plasma with (FIG. 17A) PBS, 200 µg/ml IgG1/IgG2 Fc silent B6H12.2 and 10 µM ADP.
Figure 17B:
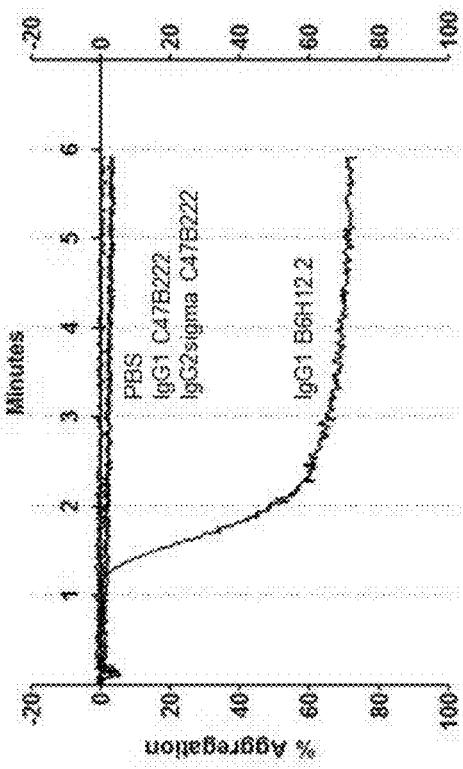
Figure 17C:
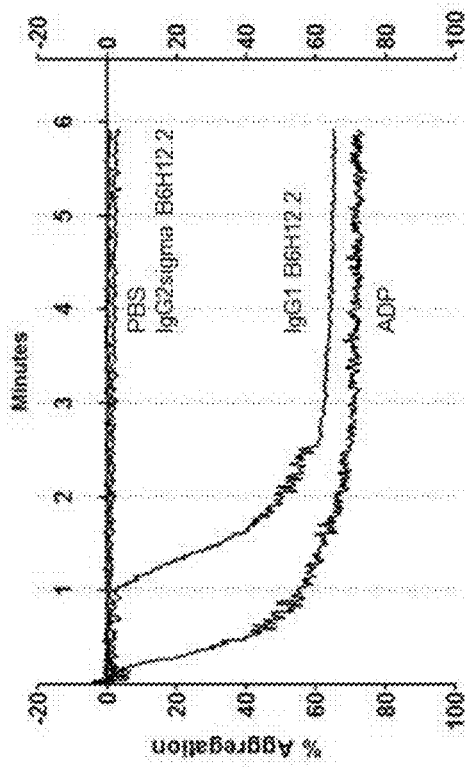
Figure 17D:
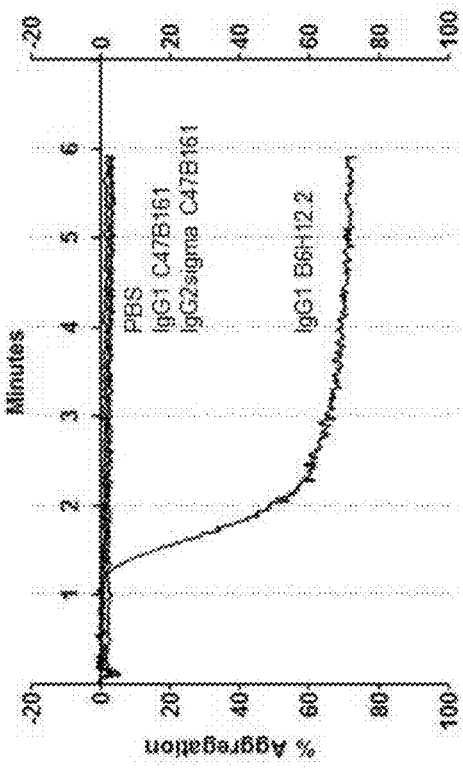

To assess platelet aggregation activity of the herein described mAbs, eight assays with independent donors were evaluated: 1.) five experiments were conducted where the activity of IgG1/IgG2sigma B6H12.2 was compared to the positive control 10 µM ADP and negative control PBS; and 2.) three experiments were conducted where the activity of IgG1/IgG2sigma C47B157, C47B161, and C47B222 was compared to IgG1 B6H12.2 and negative PBS control. The platelet aggregation assays demonstrated that C47B157, C47B161, and C47B222 did not induce platelet aggregation in either the IgG1 or IgG2sigma backbone with three independent donors when tested at concentrations ranging from 100 to 200 µg/ml (see FIG. 17b-d depicting results for an experiment run at 200 µg/ml). Maximal aggregation observed for IgG1/IgG2sigma C47B157, C47B161, and C47B222 ranged from 0 to 7% similar to what was observed for the PBS control (eight independent donors; maximal aggregation ranged from 2-11%). In contrast, B6H12.2 tested at 100 and 200 µg/ml induced aggregation as IgG1, ranging from 40 to 93% (eight donors) similar to the positive control 10 µM ADP (five donors; aggregation ranging from 55 to 120%), but not as IgG2sigma ranging from 1 to 6% (five independent donors).

In Vivo Anti-Tumor Efficacy of Fc Variants of CD47 Antibodies:

The in vivo anti-tumor activity of C47B157, C47B161, and C47B222 was tested in three human tumor cell models. Briefly, for the first two models $10 \times 10^6$ HL-60 or $5 \times 10^6$ MV4-11 cells were intravenously implanted into NSG mice. For both of these models, antibody treatment was initiated on day 6 following tumor cell implant, and animals were dosed twice weekly at 0.2 and 10 mg/kg via intraperitoneal injection. A total of six doses were administered (final dose on day 23) and each dosing group consisted of five mice. For the HL-60/NSG mice model peripheral blood from the mice was collected weekly and analyzed via FACS to assess tumor cell outgrowth and treatment effects starting on day 14 (final collection on day 42). For the MV4-11/NSG model, peripheral blood from mice was collected on day 34 and was analyzed via FACS to assess effects of treatment on tumor cell outgrowth in the peripheral blood. In a third in vivo model $10 \times 10^6$ Kasumi-3 cells were intravenously implanted into NSG mice, and treatment was initiated on day 6 following tumor cell implant. Animals were dosed twice weekly at 0.2 and 10 mg/kg via intraperitoneal injection for a total of 12 doses. Final dose was administered on day 44 and each dosing group consisted of five mice. Peripheral blood was collected from mice weekly and analyzed via FACS to assess tumor cell outgrowth in the peripheral blood starting on day 14.

Figure 19A:
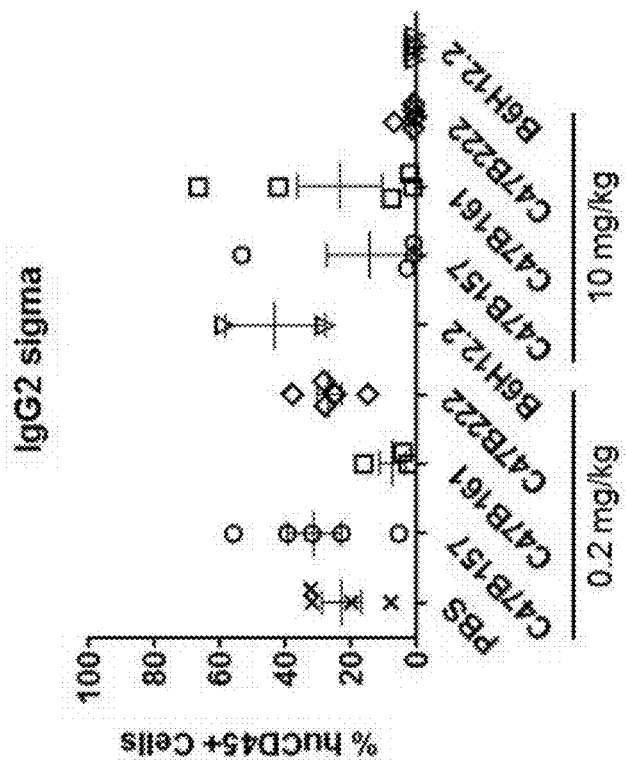
FIGS. 19A and 19B. In vivo activity of IgG1/IgG2 Fc-silent C47B157, C47B161, C47B222, and B6H12.2 in the MV4-11/NSG mice model. NSG mice were intravenously implanted with five million MV4-11 cells and antibody treatment was initiated on day 6 following tumor cell implant. Each group consisted of five mice. Animals received a total of six doses, twice weekly (final dose day 23). Peripheral blood from mice was collected on day 34 and was analyzed via FACS to assess effects of treatment on tumor cell outgrowth.
Figure 19B:
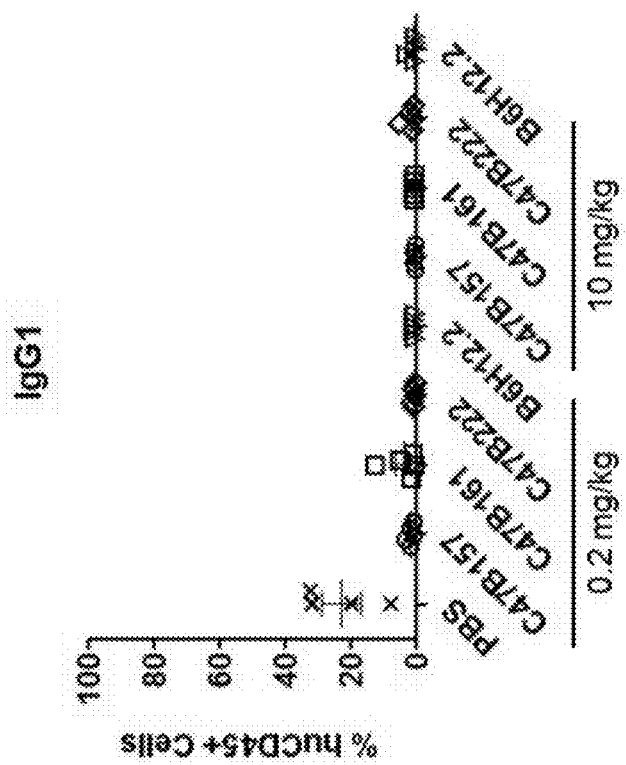
Figure 20A:
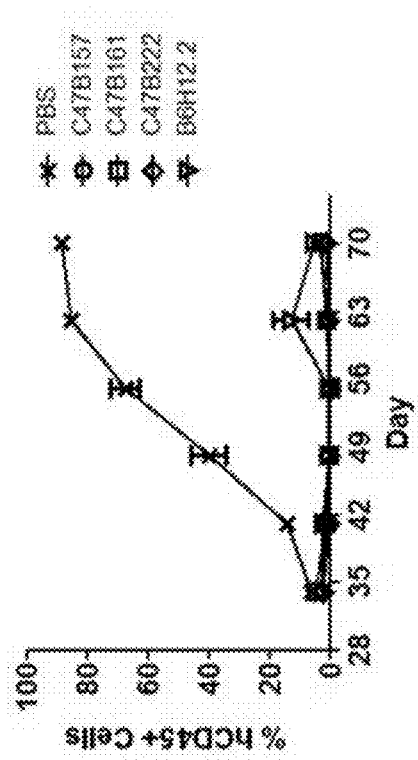
FIG. 20A-20D. In vivo activity of IgG1/IgG2 Fc-silent C47B157, C47B161, C47B222, and B6H12.2 in the Kasumi-3/NSG mice model. NSG mice were implanted with 10 million Kasumi-3 cells intravenously and antibody treatment was initiated on day 6 following tumor cell implant. Each treatment group consisted of five mice. Animals received a total of twelve doses, twice weekly (final dose day 44). Peripheral blood from the mice was collected weekly and analyzed via FACS to assess tumor cell outgrowth and treatment effects starting on day 14. Graph shows percentage of CD45% cells starting on day 34.
Figure 20B:
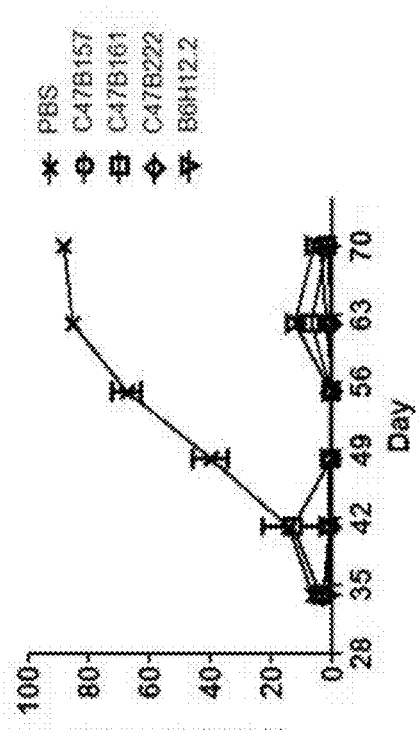
Figure 20C:
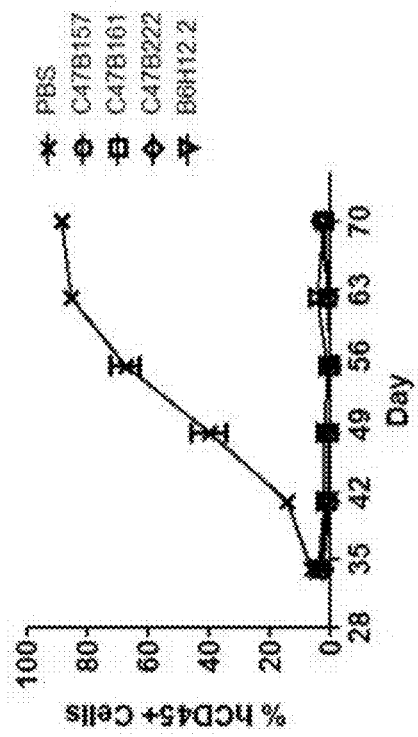
Figure 20D:
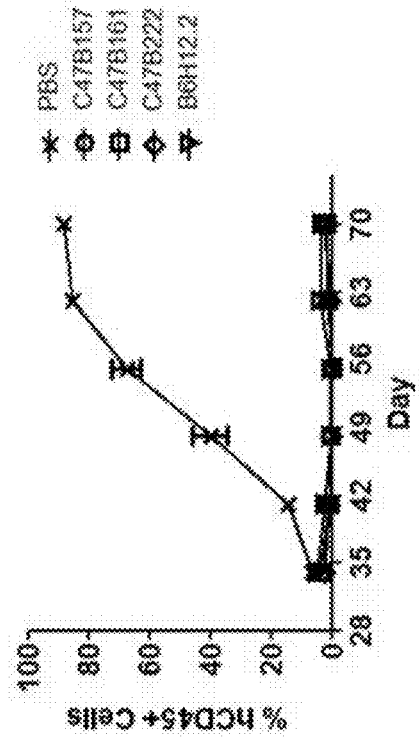

In all three models tested, C47B157, C47B161, C47B222, and B6H12.2 demonstrated anti-tumor activity. When tested in the HL60 model (see FIG. 18), the efficacy of each mAb was dependent on the dose tested and the Fc effector function of each mAb. The effector function competent IgG1 and effector function silent IgG2 sigma versions of all mAbs demonstrated dose dependent activity. IgG1 robustly suppressed tumor cell outgrowth at 10 mg/kg and delayed tumor cell outgrowth at 0.2 mg/kg. IgG2sigma delayed tumor cell growth at 10 mg/kg, while at 0.2 mg/kg the anti-tumor effects were less pronounced. Similar to the HL60 model, when tested within the MV4-11 models (FIG. 19), the mAbs effectively suppress tumor cell growth as IgG1 at 0.2 and 10 mg/kg. Tumor cell outgrowth suppression was less when the mAbs were tested in the IgG2 sigma backbone. While effector function provided an enhancement in efficacy in the HL60 and MV4-11 models, IgG1 and IgG2sigma C47B157, C47B161, C47B222, and B6H12.2 demonstrate robust anti-tumor activity when tested in the IgG1 or IgG2sigma backbone at both 0.2 and 10 mg/kg (FIG. 20).

Example 8

Proposed Mode of Antibody Neutralization

Figure 21A:
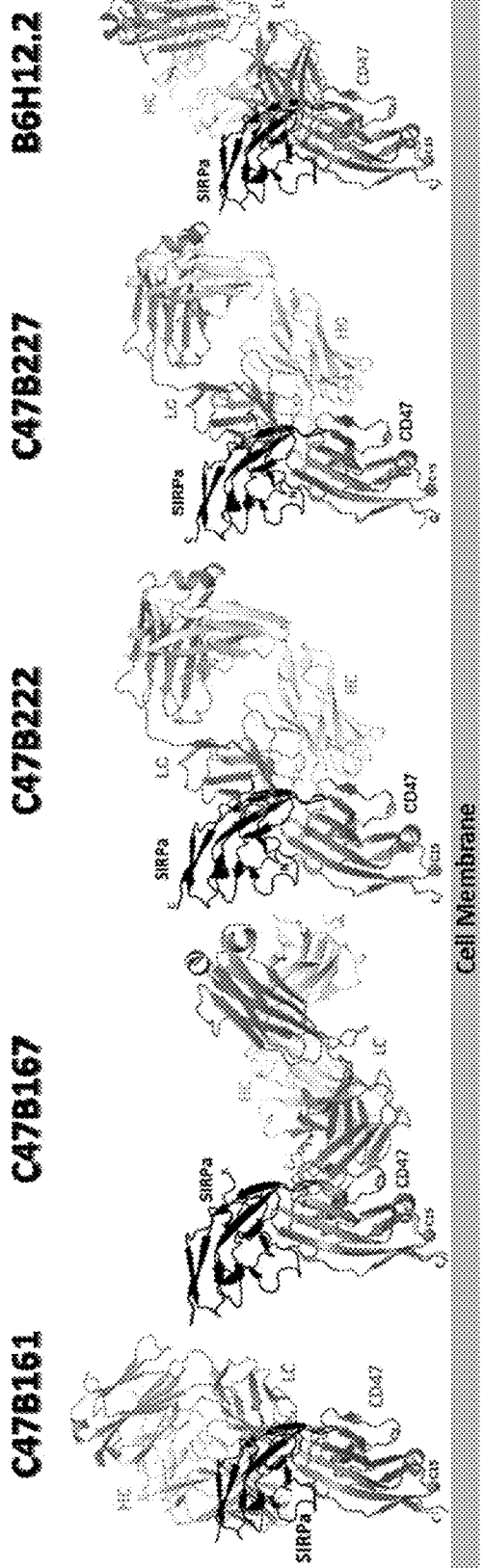
FIGS. 21A and 21B. Mode of antibody neutralization. Structural overlay of CD47/Fab complexes onto the CD47/SIRPa complex showing regions of clash between Fab and SIRP alpha. The overlay was achieved by superposition of equivalent CD47 Ca atoms in both complexes (FIG. 21A). Overlap regions between each epitope and the SIRP alpha binding site (FIG. 21B). The structure of CD47 from the C47B222 complex was used in FIG. 21B.
Figure 21B:
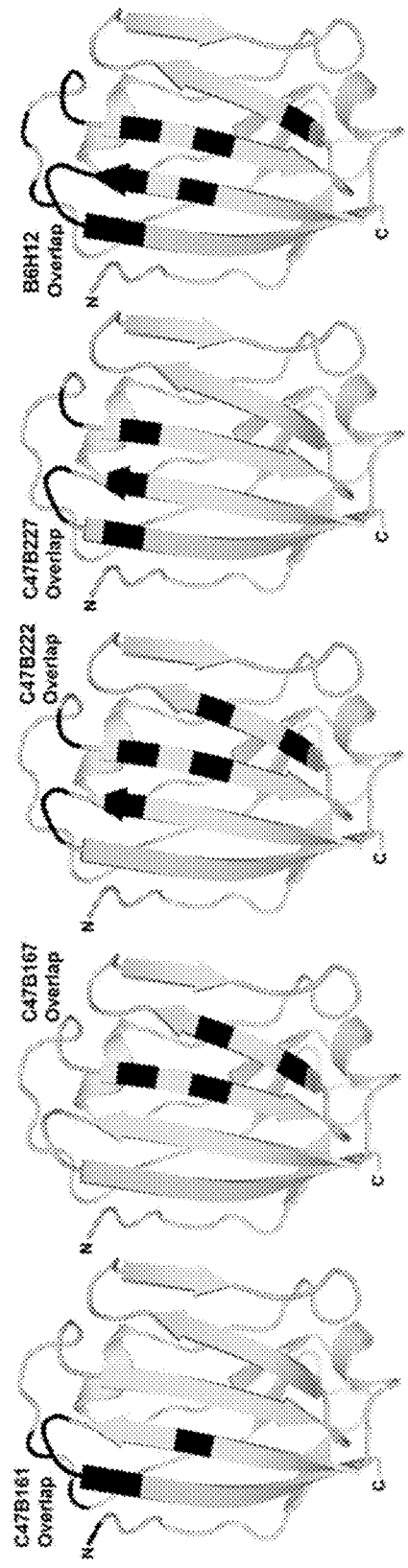

As noted in the previous examples, antibodies have been generated that can promote cell phagocytosis likely by blocking the binding of CD47 in the target cell to the SIRP alpha receptor in macrophages and, consequently, disrupting the "eat-me-not" signal that otherwise the target cell would send to the macrophage. The overlay of CD47/Fab structures with the CD47/SIRP alpha structure in FIG. 21 shows regions of clash between all Fv domains and SIRP alpha D1 domain, making impossible for both antibody and SIRP alpha to bind simultaneously to CD47.

BRIEF DESCRIPTION OF THE SEQUENCE LISTING

| SEQ ID NO: | Type | Species | Description | Sequence |
|---|---|---|---|---|
| 1 | PRT | human | IgG1-Fc Wild-type | ASTKGPSVFPLAPSSKSTSGGTAAL GCLVKDYFPEPVTVSWNSGALTSGV HTFPAVLQSSGLYSLSSVVTVPSSS LGTQTYICNVNHKPSNTKVDKKVEP KSCDKTHTCPPCPAPELLGGPSVFL FPPKPKDTLMISRTPEVTCVVVDVS HEDPEVKFNWYVDGVEVHNAKTKPR EEQYNSTYRVVSVLTVLHQDWLNGK EYKCKVSNKALPAPIEKTISKAKGQ PREPQVYTLPPSRDELTKNQVSLTC LVKGFYPSDIAVEWESNGQPENNYK TTPPVLDSDGSFFLYSKLTVDKSRW QQGNVFSCSVMHEALHNHYTQKSLS LSPGK |
| 2 | PRT | human | IgG2-Fc-Wild-type | ASTKGPSVFPLAPCSRSTSESTAAL GCLVKDYFPEPVTVSWNSGALTSGV HTFPAVLQSSGLYSLSSVVTVPSSN FGTQTYTCNVDHKPSNTKVDKTVER KCCVECPPCPAPPVAGPSVFLFPPK PKDTLMISRTPEVTCVVVDVSHEDP EVQFNWYVDGVEVHNAKTKPREEQF NSTFRVVSVLTVVHQDWLNGKEYKC KVSNKGLPAPIEKTISKTKGQPREP QVYTLPPSREEMTKNQVSLTCLVKG FYPSDIAVEWESNGQPENNYKTTPP MLDSDGSFFLYSKLTVDKSRWQQGN VFSCSVMHEALHNHYTQKSLSLSPG K |
| 3 | PRT | human | IgG2 sigma-Fc | ASTKGPSVFPLAPCSRSTSESTAAL GCLVKDYFPEPVTVSWNSGALTSGV HTFPAVLQSSGLYSLSSVVTVTSSN FGTQTYTCNVDHKPSNTKVDKTVER KCCVECPPCPAPPAAASSVFLFPPK PKDTLMISRTPEVTCVVVDVSAEDP |

| SEQ ID NO: | Type | Species | Description | Sequence |
|---|---|---|---|---|
| | | | | EVQFNWYVDGVEVHNAKTKPREEQF NSTFRVVSVLTVLHQDWLNGKEYKC KVSNKGLPSSIEKTISKTKGQPREP QVYTLPPSREEMTKNQVSLTCLVKG FYPSDIAVEWESNGQPENNYKTTPP MLDSDGSFFLYSKLTVDKSRWQQGN VFSCSVMHEALHNHYTQKSLSLSPG K |
| 4 | PRT | artificial | C47B157-VH | QVQLVQSGAEVKKPGASVKVSCKAS GYTFTDYNMHWVRQAPGQGLEWMGD IYPYNGGTYNQKFKGRVTMTRDTS TSTVYMELSSLRSEDTAVYYCARGG WHAMDSWGQGTLVTVSS |
| 5 | PRT | artificial | C47B161-VH | QVQLVQSGAEVKKPGASVKVSCKAS GYTFTDYNMHWVRQAPGQRLEWMGD IYPYNGGTYNQKFKGRVTITRDTS ASTAYMELSSLRSEDTAVYYCARGG WHAMDSWGQGTLVTVSS |
| 6 | PRT | artificial | C47B222-VH | EVQLVQSGAEVKKPGESLKISCKGS GYSFTDYWIGWVRQMPGKGLEWMGI TYPGDSDTRYSPSFQGQVTISADKS ISTAYLQWSSLKASDTAVYYCARVG RFASHQLDYWGQGTLVTVSS |
| 7 | PRT | artificial | C47B157 and C47B161-VL | DIVMTQSPLSLPVTPGEPASISCRS RQSIVHTNRYTYLAWYLQKPGQSPQ LLIYKVSNRFSGVPDRFSGSGSGTD FTLKISRVEAEDVGVYYCFQGSHVP YTFGGGTKLEIK |
| 8 | PRT | artificial | C47B222-VL | EIVLTQSPATLSLSPGERATLSCRA SQSVNNRLAWYQQKPGQAPRLLIHW ASTRAIGIPARFSGSGSGTDFTLTI SSLEPEDFAVYYCQQGASWPFTFGQ GTKVEIK |
| 9 | PRT | mouse | C47B157 and C47B161-HCDR1 | DYNMH |
| 10 | PRT | mouse | C47B222-HCDR1 | DYWIG |
| 11 | PRT | mouse | C47B157 and C47B161-HCDR2 | DIYPYNGGTYNQKFKG |
| 12 | PRT | mouse | C47B222-HCDR2 | IIYPGDSDTRYSPSFQG |
| 13 | PRT | mouse | C47B157 and C47B161-HCDR3 | GGWHAMDS |
| 14 | PRT | mouse | C47B222-HCDR3 | VGRFASHQLDY |
| 15 | PRT | mouse | C47B157 and C47B161-LCDR1 | RSRQSIVHTNRYTYLA |
| 16 | PRT | mouse | C47B222-LCDR1 | RASQSVNNRLA |
| 17 | PRT | mouse | C47B157 and C47B161-LCDR2 | KVSNRFS |

| SEQ ID NO: | Type | Species | Description | Sequence |
|---|---|---|---|---|
| 18 | PRT | mouse | C47B222-LCDR2 | WASTRAI |
| 19 | PRT | mouse | C47B157 and C47B161-LCDR3 | FQGSHVPYT |
| 20 | PRT | mouse | C47B222-LCDR3 | QQGASWPFT |
| 21 | PRT | human | CD47 | MWPLVAALLLGSACCGSAQLLFNKT KSVEFTFCNDTVVIPCFVTNMEAQN TTEVYVKWKFKGRDIYTFDGALNKS TVPTDFSSAKIEVSQLLKGDASLKM DKSDAVSHTGNYTCEVTELTREGET IIELKYRVVSWFSPNENILIVIFPI FAILLFWGQFGIKTLKYRSGGMDEK TIALLVAGLVITVIVIVGAILFVPG EYSLKNATGLGLIVTSTGILILLHY YVFSTAIGLTSFVIAILVIQVIAYI LAVVGLSLCIAACIPMHGPLLISGL SILALAQLLGLVYMKFVASNQKTIQ PPRKAVEEPLNAFKESKGMMNDE |
| 22 | PRT | human | CD47-ECD | QLLFNKTKSVEFTFCNDTVVIPCFV TNMEAQNTTEVYVKWKFKGRDIYTF DGALNKSTVPTDFSSAKIEVSQLLK GDASLKMDKSDAVSHTGNYTCEVTE LTREGETIIELKYRVVSWFSPNE |
| 23 | DNA | artificial | HuG1_DN VH_F169 | CAAAGTATACAGGCCCAGGTGCAGC TGGTGCAGAG |
| 24 | DNA | artificial | HuG1_DN VH_F323 | CAAAGTATACAGGCCGAAGTGCAGC TGCTGGAAAG |
| 25 | DNA | artificial | HuG1_DN VH_F551 | CAAAGTATACAGGCCGAAGTGCAGC TGGTGCAGAGC |
| 26 | DNA | artificial | HuG1_DN VH_R | GCCCTTGGTGGAGGCGCTGCTCACG GTCACCAG |
| 27 | DNA | artificial | HuK_DNVL_ FA27L6muSP | CAAAGTATCCAAGCAGAAATTGTGC TGACCCAGAG |
| 28 | DNA | artificial | HuK_DNVL_ FO12muSP | CAAAGTATCCAAGCAGATATTGAGA TGACCCAGAGC |
| 29 | DNA | artificial | HuK_DNVL_R | TGCAGCCACCGTACGTTTAATTTCC ACTTTGGTGCC |
| 30 | PRT | mouse | C47B116-VH | EVQLQQSGPELVKPGASVKISCKAS GYTFTDYNMHWVKQSHGKSLEWIGD IYPYNGGTYNQKFKSKATLTVDNS SSTAYMELRSLTSEDSAVYYCARGG WHAMDSWGQGTSVTVSS |
| 31 | PRT | artificial | C47B151, C47B152, and C47B153-VH | QVQLVQSGAEVKKPGSSVKVSCKAS GYTFTDYNMHWVRQAPGQGLEWMGD IYPYNGGTYNQKFKGRVTITADES TSTAYMELSSLRSEDTAVYYCARGG WHAMDSWGQGTLVTVSS |
| 32 | PRT | artificial | C47B147, C47B148 and C47B149-VH | EVQLVQSGAEVKKPGESLKISCKGS GYTFTDYNMHWVRQMPGKGLEWMGD IYPYNGGTYNQKFKGQVTISADKS ISTAYLQWSSLKASDTAMYYCARGG WHAMDSWGQGTLVTVSS |
| 33 | PRT | artificial | C47B159, C47B155, C47B151, C47B147-VL | DIVMTQSPDSLAVSLGERATINCRS RQSIVHTNRYTYLAWYQQKPGQPPK LLIYKVSNRFSGVPDRFSGSGSGTD FTLTISSLQAEDVAVYYCFQGSHVP YTFGGGTKLEIK |

| SEQ ID NO: | Type | Species | Description | Sequence |
|---|---|---|---|---|
| 34 | PRT | artificial | C47B160, C47B156, C47B152, C47B148- VL | EIVLTQSPATLSLSPGERATLSCRS RQSIVHTNRYTYLAWYQQKPGQAPR LLIYKVSNRFSGIPARFSGSGSGTD FTLTISSLEPEDFAVYYCFQGSHVP YTFGGGTKLEIK |
| 35 | PRT | artificial | C47B237, C47B238, C47B239, C47B240, C47B91 VH | EVQLVQSGAEVKKPGESLKISCKGS GYSFTSYWIGWVRQMPGKGLEWMGI IYPGDSDTRYSPSFQGQVTISADKS ISTAYLQWSSLKASDTAMYYCARVG RFASHQLDYWGQGTLVTVSS |
| 36 | PRT | artificial | C47B91, C47B213, C47B217, C47B221, C47B229, C47B230, C47B225, C47B231, C47B234, C47B235, C47B236 VL | EIVLTQSPATLSLSPGERATLSCRA SQSVNKALAWYQQKPGQAPRLLIYG ASNRATGIPARFSGSGSGTDFTLTI SSLEPEDFAVYYCQQGKGWPFTFGQ GTKVEIK |
| 37 | PRT | artificial | C47B213, C47B214, C47B215, C47B216, C47B241 VH | EVQLVQSGAEVKKPGESLKISCKGS GYSFDDSWIGWVRQMPGKGLEWMGI IYPGDSDTRYSPSFQGQVTISADKS ISTAYLQWSSLKASDTAVYYCARVG RFASHQLDYWGQGTLVTVSS |
| 38 | PRT | artificial | C47B217, C47B218, C47B219, C47B220, C47B242 VH | EVQLVQSGAEVKKPGESLKISCKGS GYSFTDSWIGWVRQMPGKGLEWMGI IYPGDSDTRYSPSFQGQVTISADKS ISTAYLQWSSLKASDTAVYYCARVG RFASHQLDYWGQGTLVTVSS |
| 39 | PRT | artificial | C47B229 VH | EVQLVQSGAEVKKPGESLKISCKGS GYSFDDAWIGWVRQMPGKGLEWMGI TYPGDSDTRYSPSFQGQVTISADKS ISTAYLQWSSLKASDTAVYYCARVG RFASHQLDYWGQGTLVTVSS |
| 40 | PRT | artificial | C47B230 VH | EVQLVQSGAEVKKPGESLKISCKGS GYSFTDDWIGWVRQMPGKGLEWMGI TYPGDSDTRYSPSFQGQVTISADKS ISTAYLQWSSLKASDTAVYYCARVG RFASHQLDYWGQGTLVTVSS |
| 41 | PRT | artificial | C47B225, C47B226, C47B227, C47B228, C47B244 VH | EVQLVQSGAEVKKPGESLKISCKGS GYSFDDYWIGWVRQMPGKGLEWMGI TYPGDSDTRYSPSFQGQVTISADKS ISTAYLQWSSLKASDTAVYYCARVG RFASHQLDYWGQGTLVTVSS |
| 42 | PRT | artificial | C47B231, C47B232, C47B233 VH | EVQLVQSGAEVKKPGESLKISCKGS GYSFTNYWIGWVRQMPGKGLEWMGI TYPGDSDTRYSPSFQGQVTISADKS ISTAYLQWSSLKASDTAVYYCARVG RFASHQLDYWGQGTLVTVSS |
| 43 | PRT | artificial | C47B234 VH | EVQLVQSGAEVKKPGESLKISCKGS GYSFDNYWIGWVRQMPGKGLEWMGI TYPGDSDTRYSPSFQGQVTISADKS ISTAYLQWSSLKASDTAVYYCARVG RFASHQLDYWGQGTLVTVSS |
| 44 | PRT | artificial | C47B235 VH | EVQLVQSGAEVKKPGESLKISCKGS GYSFDDYWISWVRQMPGKGLEWMGI IYPGDSDTRYSPSFQGQVTISADKS ISTAYLQWSSLKASDTAVYYCARVG RFASHQLDYWGQGTLVTVSS |

| SEQ ID NO: | Type | Species | Description | Sequence |
|---|---|---|---|---|
| 45 | PRT | artificial | C47B236 VH | EVQLVQSGAEVKKPGESLKISCKGS GYSFKDDWIGWVRQMPGKGLEWMGI TYPGDSDTRYSPSFQGQVTISADKS ISTAYLQWSSLKASDTAVYYCARVG RFASHQLDYWGQGTLVTVSS |
| 46 | PRT | artificial | C47B238, C47B215, C47B219, C47B223, C47B227, C47B233 VL | EIVLTQSPATLSLSPGERATLSCRA SQSVGSRLAWYQQKPGQAPRLLIYW ASTRATGIPARFSGSGSGTDFTLTI SSLEPEDFAVYYCQQGAYWPFTFGQ GTKVEIK |
| 47 | PRT | artificial | C47B239, C47B241, C47B242, C47B243, C47B244 VL | EIVLTQSPATLSLSPGERATLSCRA SQSVSNRLAWYQQKPGQAPRLLIYG ASNRATGIPARFSGSGSGTDFTLTI SSLEPEDFAVYYCQQGRSWPFTFGQ GTKVEIK |
| 48 | PRT | artificial | C47B240, C47B216, C47B220, C47B224, C47B228 VL | EIVLTQSPATLSLSPGERATLSCRA SQSVSNRQAWYQQKPGQAPRLLIHS ASNRATGIPARFSGSGSGTDFTLTI SSLEPEDFAVYYCQQGRSWPFTFGQ GTKVEIK |
| 49 | PRT | human | CD47-ECD-C15G | QLLFNKTKSVEFTFGNDTVVIPCFV TNMEAQNTTEVYVKWKFKGRDIYTF DGALNKSTVPTDFSSAKIEVSQLLK GDASLKMDKSDAVSHTGNYTCEVTE LTREGETIIELKYRVVSWFSPNE |
| 50 | PRT | artificial | C47B167-VH | EVQLVQSGAEVKKPGESLKISCKGS GYTFTSYWMQWVRQMPGKGLEWMGE INPSNGRTDYNEKFRGQVTISADKS ISTAYLQWSSLKASDTAMYYCARQG GSGYGNSYGFFDVWGQGTTVTVSS |
| 51 | PRT | artificial | C47B167-VL | EIVLTQSPATLSLSPGERATLSCRA SSSVSYMHWYQQKPGQAPRLLIYDT SRLASGIPARFSGSGSGTDFTLTIS SLEPEDFAVYYCQQWRSNPYTFGGG TKVEIK |
| 52 | PRT | mouse | B6H12.2-VH | EVKLVESGGDLVKPGGSLKLSCAAS GFTFSGYGMSWVRQTPDKRLEWVAT ITSGGTYTYYPDSVKGRFTISRDNA KNTLYLQIDSLKSEDTAIYFCARSL AGNAMDYWGQGTSVTVSS |
| 53 | PRT | mouse | B6H12.2-VL | DIVMTQSPATLSVTPGDRVSLSCRA SQTISDYLHWYQQKSHESPRLLIKF ASQSISGIPSRFSGSGSGSDFTLSI NSVEPEDVGVYYCQNGHGFPRTFGG GTKLEIK |
| 54 | PRT | mouse | C47B116 VL | DVVMTQTPLSLPVSLGDQASISCRS RQSIVHTNRYTYLAWYLQKPGQSPK LLIYKVSNRFSGVPDRFSGSGSGTD FTLKISRVEAEDLGVYYCFQGSHVP YTFGGGTKLEIK |

What is claimed is:

1. An isolated antibody or antigen binding fragment thereof comprising the following properties:
   a. the antibody or antigen binding fragment specifically binds to CD47 by interacting with CD47 (SEQ ID NO: 21 excluding the signal sequence) amino acid residues:
      i. Q1, L3, N27, E29, E97, L101, T102, R103, and E104;
      ii. Y37, K39, R45, D46, T49, A53, L54, N55, K56, S57, T58, V59, P60, T61, T564, A66, and K67;
      iii. E35, K39, Y37, D46, 49, D51, A53, L54, K56, T58, V59, T99, L101, and T102; or
      iv. E29, Q31, N32, E35, V36, Y37, K39, N41, D46, D51, A53, E97, T99, E100, L101, T102, R103, and E104;

b. the antibody or antigen binding fragment thereof prevents CD47 from interacting with signal-regulatory protein alpha (SIRP alpha);

c. the antibody or antigen binding fragment thereof does not have significant platelet aggregation activity and wherein the antibody or antigen binding fragment thereof comprises a VH complementarity determining region 1 (CDR1) sequence set forth in SEQ ID NO: 9 or SEQ ID NO: 10, a VH CDR2 sequence set forth in SEQ ID NO: 11 or SEQ ID NO: 12, a VH CDR3 sequence set forth in SEQ ID NO: 13 or SEQ ID NO: 14, a VL CDR1 sequence set forth in SEQ ID NO: 15 or SEQ ID NO: 16, a VL CDR2 sequence set forth in SEQ ID NO: 17 or SEQ ID NO: 18 and a VL CDR3 sequence set forth in SEQ ID NO: 19 or SEQ ID NO: 20.

2. The antibody of claim 1 wherein the antibody or antigen binding fragment specifically binds to human or cyno CD47, and comprises a variable heavy (VH) chain region selected from the group consisting of SEQ ID NOs: 4-6.

3. The antibody of claim 2, wherein the antibody or antigen binding fragment thereof comprises a variable light (VL) chain region selected from the group consisting of SEQ ID NOs: 7 and 8.

4. The antibody of claim 2, wherein the antibody or antigen binding fragment thereof comprises a VH region selected from the group consisting of SEQ ID NOs: 4-6 and a VL region selected from the group consisting of SEQ ID NOs: 7 and 8.

5. The antibody of claim 4, wherein the VH chain region comprises SEQ ID NO: 4 or SEQ ID NO: 5 paired with a VL chain region comprising SEQ ID NO: 7.

6. The antibody of claim 4, wherein the VH chain region comprises SEQ ID NO: 6 paired with a VL chain region comprising SEQ ID NO: 8.

7. The antibody of claim 1, wherein the antibody or antigen binding fragment thereof comprises a VH CDR1 sequence set forth in SEQ ID NO: 9, a VH CDR2 sequence set forth in SEQ ID NO: 11, a VH CDR3 sequence set forth in SEQ ID NO: 13, a VL CDR1 sequence set forth in SEQ ID NO: 15, a VL CDR2 sequence set forth in SEQ ID NO: 17, and a VL CDR3 sequence set forth in SEQ ID NO: 19.

8. The antibody of claim 1, wherein the antibody or antigen binding fragment thereof comprises a VH CDR1 sequence set forth in SEQ ID NO: 10, a VH CDR2 sequence set forth in SEQ ID NO: 12, a VH CDR3 sequence set forth in SEQ ID NO: 14, a VL CDR1 set forth in SEQ ID NO: 16, a VL CDR2 sequence set forth in SEQ ID NO: 18, and a VL CDR3 sequence set forth in SEQ ID NO: 20.

9. The antibody of claim 2, wherein the VH chain of the antibody has more extensive contacts with CD47 than the VL chain of the antibody.

10. The antibody of claim 2, wherein the epitope bound by the VH chain of the antibody is positioned near the membrane of a CD47 expressing cell, and wherein the VL chain of the antibody occludes a SIRP alpha binding site on CD47.

11. The antibody of claim 2, wherein the antibody does not have significant hemagglutination activity.

12. The antibody of claim 2, wherein the platelet-aggregation activity of the antibody is no more than 10% greater than the degree of platelet-aggregation observed in the absence of the antibody.

13. The antibody of claim 2, wherein the antibody is chimeric, humanized, or fully human.

14. The antibody of claim 2, wherein the CD47 is human CD47 or cyno CD47.

15. The antibody of claim 2, wherein the antibody or antigen binding fragment thereof promotes macrophage-mediated phagocytosis of a CD47-expressing cell.

16. The antibody of claim 2, wherein the antibody or antigen binding fragment thereof comprises an IgG isotype selected from the group consisting of IgG1 isotype and IgG2 isotype.

17. A pharmaceutical composition comprising the antibody of claim 2 and a pharmaceutical acceptable carrier.

* * * * *